United States Patent [19]

Cody et al.

[11] Patent Number: 5,550,110

[45] Date of Patent: Aug. 27, 1996

[54] ENDOTHELIN ANTAGONISTS II

[75] Inventors: Wayne L. Cody, Saline; Annette M. Doherty; John G. Topliss, both of Ann Arbor, all of Mich.

[73] Assignee: Warner-Lambert Company, Morris Plains, N.J.

[21] Appl. No.: 269,257

[22] Filed: Jun. 30, 1994

Related U.S. Application Data

[63] Continuation-in-part of Ser. No. 33,515, Mar. 31, 1993, abandoned, which is a continuation-in-part of Ser. No. 872,225, Apr. 22, 1992, abandoned.

[51] Int. Cl.$^6$ .................... A61K 38/04; A61K 38/08; C07K 5/04; C07K 7/06

[52] U.S. Cl. .................... 514/17; 514/18; 514/19; 514/20; 514/297; 514/437; 514/454; 514/561; 514/564; 514/567; 530/329; 530/330; 530/331; 546/104; 549/26; 549/390; 562/445; 562/450

[58] Field of Search .................... 546/104; 549/26, 549/390; 562/445, 450; 530/329, 330, 331; 514/17, 18, 19, 20, 297, 437, 454, 561, 564, 567

[56] References Cited

U.S. PATENT DOCUMENTS

| | | | |
|---|---|---|---|
| 5,264,577 | 11/1993 | Beylin et al. | 549/26 |
| 5,382,569 | 1/1995 | Cody et al. | 514/17 |
| 5,430,022 | 7/1995 | Hemmi et al. | 530/331 |

FOREIGN PATENT DOCUMENTS

| | | |
|---|---|---|
| 9220706 | 11/1992 | WIPO. |
| 9321219 | 10/1993 | WIPO. |

OTHER PUBLICATIONS

Copending U.S. Ser. No. 07/995,480 Filed: Dec. 21, 1992 U.S. Pat. No. (5,382,569).
International Search Report, PCT/US 95/04171 (completed 10 Jul. 1995).
208th ACS National Meeting, Aug. 1994, MEDI 218, He et al.
208th ACS National Meeting, Aug. 1994, MEDI 150, Cody et al.
Chemical Abstracts 72: 100435a (1970).
Eur. J. Pharm., vol. 252, No. 3, issued 1994, Battistini et al, "Comparison of PD 145065 and Ro 46–2005 as Antagonists . . . ", pp. 341–345.
Med. Chem. Res., vol. 3, issued 1993, Cody et al, "The Rational Design of a Highly Potent Combined $ET_A$ and $ET_B$ . . . ", pp. 154–162.
Copending U.S. Ser. No. 07/701,274 Filed: May 16, 1991.
Copending U.S. Ser. No. 07/809,746 Filed Dec. 18, 1991.
International Search Report—Corresponding PCT Application PCT/93/03658.
Tamiaki, H., et al vol. 1, 1991 pp. 817–822 J. Chem. Soc. Perkin Trans.—(See Attached Communication Explaining Relevance Of Reference).
J. Cardiovasc. Pharm. vol. 17, No. 7, 1991 pp. S59–S61, Doherty, A. M., et al. (Previously Cited).
J. Med. Chem., vol. 35, 1992, pp. 3301–3303 Cody, W. L, et al. (Published After Priority Date).

*Primary Examiner*—Jeffrey E. Russel
*Attorney, Agent, or Firm*—Francis J. Tinney

[57] ABSTRACT

Novel antagonists of endothelin are described, as well as methods for the preparation and pharmaceutical compositions of the same, which are useful in treating elevated levels of endothelin, acute and chronic renal failure, hypertension, myocardial infarction, metabolic, endocrinological, neurological disorders especially cerebral vasospasm, stroke, and head injury, congestive heart failure, endotoxic shock, subarachnoid hemorrhage, arrhythmias, asthma, preeclampsia, atherosclerotic disorders including Raynaud's disease, restenosis, angina, cancer, pulmonary hypertension, ischemic disease, gastric mucosal damage, hemorrhagic shock, ischemic bowel disease, and diabetes.

27 Claims, No Drawings

SEQUENCE LISTING ( 1 ) GENERAL INFORMATION:

( i i i ) NUMBER OF SEQUENCES: 64

( 2 ) INFORMATION FOR SEQ ID NO:1:

( i ) SEQUENCE CHARACTERISTICS:
        ( A ) LENGTH: 6 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:1:

Xaa Xaa Xaa Xaa Xaa Xaa
        1                       5

( 2 ) INFORMATION FOR SEQ ID NO:2:

( i ) SEQUENCE CHARACTERISTICS:
        ( A ) LENGTH: 6 amino acids
        ( B .) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:2:

Xaa Leu Asp Ile Ile Trp
        1                       5

( 2 ) INFORMATION FOR SEQ ID NO:3:

( i ) SEQUENCE CHARACTERISTICS:
        ( A ) LENGTH: 6 amino acids
        ( B ) TYPE: amino acid
        ( C ) STRANDEDNESS: single (D) TOPOLOGY: linear (ii) MOLECULE TYPE: peptide (xi) SEQUENCE DESCRIPTION: SEQ ID NO:3:

```
Xaa Xaa Asp Ile Ile Trp
1               5
```

(2) INFORMATION FOR SEQ ID NO:4:

(i) SEQUENCE CHARACTERISTICS:
(A) LENGTH: 6 amino acids
(B) TYPE: amino acid
(C) STRANDEDNESS: single
(D) TOPOLOGY: linear (ii) MOLECULE TYPE: peptide (xi) SEQUENCE DESCRIPTION: SEQ ID NO:4:

```
Xaa Lys Asp Ile Ile Trp
1               5
```

(2) INFORMATION FOR SEQ ID NO:5:

(i) SEQUENCE CHARACTERISTICS:
(A) LENGTH: 6 amino acids
(B) TYPE: amino acid
(C) STRANDEDNESS: single
(D) TOPOLOGY: linear (ii) MOLECULE TYPE: peptide (xi) SEQUENCE DESCRIPTION: SEQ ID NO:5:

```
Xaa Asp Asp Ile Ile Trp
1               5
```

(2) INFORMATION FOR SEQ ID NO:6:

(i) SEQUENCE CHARACTERISTICS:
(A) LENGTH: 6 amino acids
(B) TYPE: amino acid
(C) STRANDEDNESS: single
(D) TOPOLOGY: linear (ii) MOLECULE TYPE: peptide (xi) SEQUENCE DESCRIPTION: SEQ ID NO:6:

```
Xaa Glu Asp Ile Ile Trp
1               5
```

(2) INFORMATION FOR SEQ ID NO:7:

(i) SEQUENCE CHARACTERISTICS:
(A) LENGTH: 6 amino acids
(B) TYPE: amino acid
(C) STRANDEDNESS: single
(D) TOPOLOGY: linear (ii) MOLECULE TYPE: peptide (xi) SEQUENCE DESCRIPTION: SEQ ID NO:7:

```
Xaa Phe Asp Ile Ile Trp
1               5
```

(2) INFORMATION FOR SEQ ID NO:8:

(i) SEQUENCE CHARACTERISTICS:
(A) LENGTH: 6 amino acids
(B) TYPE: amino acid
(C) STRANDEDNESS: single (D) TOPOLOGY: linear (ii) MOLECULE TYPE: peptide (xi) SEQUENCE DESCRIPTION: SEQ ID NO:8:

```
Xaa  Arg  Asp  Ile  Ile  Trp
1                   5
```

(2) INFORMATION FOR SEQ ID NO:9:

(i) SEQUENCE CHARACTERISTICS:
(A) LENGTH: 5 amino acids
(B) TYPE: amino acid
(C) STRANDEDNESS: single
(D) TOPOLOGY: linear (ii) MOLECULE TYPE: peptide (xi) SEQUENCE DESCRIPTION: SEQ ID NO:9:

```
Xaa  Asp  Ile  Ile  Trp
1                   5
```

(2) INFORMATION FOR SEQ ID NO:10:

(i) SEQUENCE CHARACTERISTICS:
(A) LENGTH: 6 amino acids
(B) TYPE: amino acid
(C) STRANDEDNESS: single
(D) TOPOLOGY: linear (ii) MOLECULE TYPE: peptide (xi) SEQUENCE DESCRIPTION: SEQ ID NO:10:

```
Xaa  Leu  Phe  Ile  Ile  Trp
1                   5
```

(2) INFORMATION FOR SEQ ID NO:11:

(i) SEQUENCE CHARACTERISTICS:
(A) LENGTH: 6 amino acids
(B) TYPE: amino acid
(C) STRANDEDNESS: single
(D) TOPOLOGY: linear (ii) MOLECULE TYPE: peptide (xi) SEQUENCE DESCRIPTION: SEQ ID NO:11:

```
Xaa  Leu  Asn  Ile  Ile  Trp
1                   5
```

(2) INFORMATION FOR SEQ ID NO:12:

(i) SEQUENCE CHARACTERISTICS:
(A) LENGTH: 6 amino acids
(B) TYPE: amino acid
(C) STRANDEDNESS: single
(D) TOPOLOGY: linear (ii) MOLECULE TYPE: peptide (xi) SEQUENCE DESCRIPTION: SEQ ID NO:12:

```
Xaa  Leu  Glu  Ile  Ile  Trp
1                   5
```

(2) INFORMATION FOR SEQ ID NO:13:

(i) SEQUENCE CHARACTERISTICS:
(A) LENGTH: 6 amino acids
(B) TYPE: amino acid
(C) STRANDEDNESS: single ( D ) TOPOLOGY: linear ( i i ) MOLECULE TYPE: peptide ( x i ) SEQUENCE DESCRIPTION: SEQ ID NO:13:

```
Xaa  Leu  Gln  Ile  Ile  Trp
1                  5
```

( 2 ) INFORMATION FOR SEQ ID NO:14:

( i ) SEQUENCE CHARACTERISTICS:
        ( A ) LENGTH: 6 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:14:

```
Xaa  Leu  Tyr  Ile  Ile  Trp
1                  5
```

( 2 ) INFORMATION FOR SEQ ID NO:15:

( i ) SEQUENCE CHARACTERISTICS:
        ( A ) LENGTH: 6 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:15:

```
Xaa  Leu  Xaa  Ile  Ile  Trp
1                  5
```

( 2 ) INFORMATION FOR SEQ ID NO:16:

( i ) SEQUENCE CHARACTERISTICS:
        ( A ) LENGTH: 6 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:16:

```
Xaa  Leu  Trp  Ile  Ile  Trp
1                  5
```

( 2 ) INFORMATION FOR SEQ ID NO:17:

( i ) SEQUENCE CHARACTERISTICS:
        ( A ) LENGTH: 6 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:17:

```
Xaa  Leu  Asp  Val  Ile  Trp
1                  5
```

( 2 ) INFORMATION FOR SEQ ID NO:18:

( i ) SEQUENCE CHARACTERISTICS:
        ( A ) LENGTH: 6 amino acids
        ( B ) TYPE: amino acid
        ( C ) STRANDEDNESS: single (D) TOPOLOGY: linear (i i) MOLECULE TYPE: peptide (x i) SEQUENCE DESCRIPTION: SEQ ID NO:18:

```
Xaa  Leu  Asp  Ile  Val  Trp
1                   5
```

(2) INFORMATION FOR SEQ ID NO:19:

(i) SEQUENCE CHARACTERISTICS:
(A) LENGTH: 6 amino acids
(B) TYPE: amino acid
(C) STRANDEDNESS: single
(D) TOPOLOGY: linear (i i) MOLECULE TYPE: peptide (x i) SEQUENCE DESCRIPTION: SEQ ID NO:19:

```
Xaa  Leu  Asp  Xaa  Ile  Trp
1                   5
```

(2) INFORMATION FOR SEQ ID NO:20:

(i) SEQUENCE CHARACTERISTICS:
(A) LENGTH: 6 amino acids
(B) TYPE: amino acid
(C) STRANDEDNESS: single
(D) TOPOLOGY: linear (i i) MOLECULE TYPE: peptide (x i) SEQUENCE DESCRIPTION: SEQ ID NO:20:

```
Xaa  Leu  Asp  Ile  Xaa  Trp
1                   5
```

(2) INFORMATION FOR SEQ ID NO:21:

(i) SEQUENCE CHARACTERISTICS:
(A) LENGTH: 6 amino acids
(B) TYPE: amino acid
(C) STRANDEDNESS: single
(D) TOPOLOGY: linear (i i) MOLECULE TYPE: peptide (x i) SEQUENCE DESCRIPTION: SEQ ID NO:21:

```
Xaa  Arg  Asp  Ile  Xaa  Trp
1                   5
```

(2) INFORMATION FOR SEQ ID NO:22:

(i) SEQUENCE CHARACTERISTICS:
(A) LENGTH: 6 amino acids
(B) TYPE: amino acid
(C) STRANDEDNESS: single
(D) TOPOLOGY: linear (i i) MOLECULE TYPE: peptide (x i) SEQUENCE DESCRIPTION: SEQ ID NO:22:

```
Xaa  Lys  Asp  Ile  Xaa  Trp
1                   5
```

(2) INFORMATION FOR SEQ ID NO:23:

(i) SEQUENCE CHARACTERISTICS:
(A) LENGTH: 6 amino acids
(B) TYPE: amino acid
(C) STRANDEDNESS: single (D) TOPOLOGY: linear (ii) MOLECULE TYPE: peptide (xi) SEQUENCE DESCRIPTION: SEQ ID NO:23:

Xaa  Xaa  Asp  Ile  Xaa  Trp
    1                   5

(2) INFORMATION FOR SEQ ID NO:24:

(i) SEQUENCE CHARACTERISTICS:
      (A) LENGTH: 6 amino acids
      (B) TYPE: amino acid
      (C) STRANDEDNESS: single
      (D) TOPOLOGY: linear (ii) MOLECULE TYPE: peptide (xi) SEQUENCE DESCRIPTION: SEQ ID NO:24:

Xaa  Asp  Asp  Ile  Xaa  Trp
    1                   5

(2) INFORMATION FOR SEQ ID NO:25:

(i) SEQUENCE CHARACTERISTICS:
      (A) LENGTH: 6 amino acids
      (B) TYPE: amino acid
      (C) STRANDEDNESS: single
      (D) TOPOLOGY: linear (ii) MOLECULE TYPE: peptide (xi) SEQUENCE DESCRIPTION: SEQ ID NO:25:

Xaa  Glu  Asp  Ile  Xaa  Trp
    1                   5

(2) INFORMATION FOR SEQ ID NO:26:

(i) SEQUENCE CHARACTERISTICS:
      (A) LENGTH: 6 amino acids
      (B) TYPE: amino acid
      (C) STRANDEDNESS: single
      (D) TOPOLOGY: linear (ii) MOLECULE TYPE: peptide (xi) SEQUENCE DESCRIPTION: SEQ ID NO:26:

Xaa  Arg  Asp  Xaa  Ile  Trp
    1                   5

(2) INFORMATION FOR SEQ ID NO:27:

(i) SEQUENCE CHARACTERISTICS:
      (A) LENGTH: 6 amino acids
      (B) TYPE: amino acid
      (C) STRANDEDNESS: single
      (D) TOPOLOGY: linear (ii) MOLECULE TYPE: peptide (xi) SEQUENCE DESCRIPTION: SEQ ID NO:27:

Xaa  Lys  Asp  Xaa  Ile  Trp
    1                   5

(2) INFORMATION FOR SEQ ID NO:28:

(i) SEQUENCE CHARACTERISTICS:
      (A) LENGTH: 6 amino acids
      (B) TYPE: amino acid
      (C) STRANDEDNESS: single (D) TOPOLOGY: linear (ii) MOLECULE TYPE: peptide (xi) SEQUENCE DESCRIPTION: SEQ ID NO:28:

```
Xaa Xaa Asp Xaa Ile Trp
1               5
```

(2) INFORMATION FOR SEQ ID NO:29:

(i) SEQUENCE CHARACTERISTICS:
(A) LENGTH: 6 amino acids
(B) TYPE: amino acid
(C) STRANDEDNESS: single
(D) TOPOLOGY: linear (ii) MOLECULE TYPE: peptide (xi) SEQUENCE DESCRIPTION: SEQ ID NO:29:

```
Xaa Asp Asp Xaa Ile Trp
1               5
```

(2) INFORMATION FOR SEQ ID NO:30:

(i) SEQUENCE CHARACTERISTICS:
(A) LENGTH: 6 amino acids
(B) TYPE: amino acid
(C) STRANDEDNESS: single
(D) TOPOLOGY: linear (ii) MOLECULE TYPE: peptide (xi) SEQUENCE DESCRIPTION: SEQ ID NO:30:

```
Xaa Glu Asp Xaa Ile Trp
1               5
```

(2) INFORMATION FOR SEQ ID NO:31:

(i) SEQUENCE CHARACTERISTICS:
(A) LENGTH: 6 amino acids
(B) TYPE: amino acid
(C) STRANDEDNESS: single
(D) TOPOLOGY: linear (ii) MOLECULE TYPE: peptide (xi) SEQUENCE DESCRIPTION: SEQ ID NO:31:

```
Xaa Leu Asp Phe Ile Trp
1               5
```

(2) INFORMATION FOR SEQ ID NO:32:

(i) SEQUENCE CHARACTERISTICS:
(A) LENGTH: 6 amino acids
(B) TYPE: amino acid
(C) STRANDEDNESS: single
(D) TOPOLOGY: linear (ii) MOLECULE TYPE: peptide (xi) SEQUENCE DESCRIPTION: SEQ ID NO:32:

```
Xaa Xaa Asp Phe Ile Trp
1               5
```

(2) INFORMATION FOR SEQ ID NO:33:

(i) SEQUENCE CHARACTERISTICS:
(A) LENGTH: 6 amino acids
(B) TYPE: amino acid
(C) STRANDEDNESS: single (D) TOPOLOGY: linear (ii) MOLECULE TYPE: peptide (xi) SEQUENCE DESCRIPTION: SEQ ID NO:33:

```
Xaa  Lys  Asp  Phe  Ile  Trp
1                  5
```

(2) INFORMATION FOR SEQ ID NO:34:

(i) SEQUENCE CHARACTERISTICS:
        (A) LENGTH: 6 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:34:

```
Xaa  Asp  Asp  Phe  Ile  Trp
1                  5
```

(2) INFORMATION FOR SEQ ID NO:35:

(i) SEQUENCE CHARACTERISTICS:
        (A) LENGTH: 6 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:35:

```
Xaa  Glu  Asp  Phe  Ile  Trp
1                  5
```

(2) INFORMATION FOR SEQ ID NO:36:

(i) SEQUENCE CHARACTERISTICS:
        (A) LENGTH: 6 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:36:

```
Xaa  Phe  Asp  Phe  Ile  Trp
1                  5
```

(2) INFORMATION FOR SEQ ID NO:37:

(i) SEQUENCE CHARACTERISTICS:
        (A) LENGTH: 6 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:37:

```
Xaa  Arg  Asp  Phe  Ile  Trp
1                  5
```

(2) INFORMATION FOR SEQ ID NO:38:

(i) SEQUENCE CHARACTERISTICS:
        (A) LENGTH: 6 amino acids
        (B) TYPE: amino acid
        (C) STRANDEDNESS: single (D) TOPOLOGY: linear (ii) MOLECULE TYPE: peptide (xi) SEQUENCE DESCRIPTION: SEQ ID NO:38:

Xaa Xaa Asp Ile Xaa Xaa
1               5

(2) INFORMATION FOR SEQ ID NO:39:

(i) SEQUENCE CHARACTERISTICS:
 (A) LENGTH: 6 amino acids
 (B) TYPE: amino acid
 (C) STRANDEDNESS: single
 (D) TOPOLOGY: linear (ii) MOLECULE TYPE: peptide (xi) SEQUENCE DESCRIPTION: SEQ ID NO:39:

Xaa Phe Asp Ile Xaa Trp
1               5

(2) INFORMATION FOR SEQ ID NO:40:

(i) SEQUENCE CHARACTERISTICS:
 (A) LENGTH: 5 amino acids
 (B) TYPE: amino acid
 (C) STRANDEDNESS: single
 (D) TOPOLOGY: linear (ii) MOLECULE TYPE: peptide (xi) SEQUENCE DESCRIPTION: SEQ ID NO:40:

Xaa Asp Ile Xaa Trp
1               5

(2) INFORMATION FOR SEQ ID NO:41:

(i) SEQUENCE CHARACTERISTICS:
 (A) LENGTH: 6 amino acids
 (B) TYPE: amino acid
 (C) STRANDEDNESS: single
 (D) TOPOLOGY: linear (ii) MOLECULE TYPE: peptide (xi) SEQUENCE DESCRIPTION: SEQ ID NO:41:

Xaa Leu Phe Ile Xaa Trp
1               5

(2) INFORMATION FOR SEQ ID NO:42:

(i) SEQUENCE CHARACTERISTICS:
 (A) LENGTH: 6 amino acids
 (B) TYPE: amino acid
 (C) STRANDEDNESS: single
 (D) TOPOLOGY: linear (ii) MOLECULE TYPE: peptide (xi) SEQUENCE DESCRIPTION: SEQ ID NO:42:

Xaa Leu Glu Ile Xaa Trp
1               5

(2) INFORMATION FOR SEQ ID NO:43:

(i) SEQUENCE CHARACTERISTICS:
 (A) LENGTH: 6 amino acids
 (B) TYPE: amino acid
 (C) STRANDEDNESS: single (D) TOPOLOGY: linear (ii) MOLECULE TYPE: peptide (xi) SEQUENCE DESCRIPTION: SEQ ID NO:43:

Xaa    Leu    Gln    Ile    Xaa    Trp
            1                            5

(2) INFORMATION FOR SEQ ID NO:44:

(i) SEQUENCE CHARACTERISTICS:
            (A) LENGTH: 6 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO:44:

Xaa    Leu    Tyr    Ile    Xaa    Trp
            1                            5

(2) INFORMATION FOR SEQ ID NO:45:

(i) SEQUENCE CHARACTERISTICS:
            (A) LENGTH: 6 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO:45:

Xaa    Leu    Xaa    Ile    Xaa    Trp
            1                            5

(2) INFORMATION FOR SEQ ID NO:46:

(i) SEQUENCE CHARACTERISTICS:
            (A) LENGTH: 6 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO:46:

Xaa    Leu    Trp    Ile    Xaa    Trp
            1                            5

(2) INFORMATION FOR SEQ ID NO:47:

(i) SEQUENCE CHARACTERISTICS:
            (A) LENGTH: 6 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO:47:

Xaa    Leu    Asp    Val    Xaa    Trp
            1                            5

(2) INFORMATION FOR SEQ ID NO:48:

(i) SEQUENCE CHARACTERISTICS:
            (A) LENGTH: 6 amino acids
            (B) TYPE: amino acid
            (C) STRANDEDNESS: single ( D ) TOPOLOGY: linear ( i i ) MOLECULE TYPE: peptide ( x i ) SEQUENCE DESCRIPTION: SEQ ID NO:48:

```
Xaa  Leu  Asp  Xaa  Xaa  Trp
1                   5
```

( 2 ) INFORMATION FOR SEQ ID NO:49:

( i ) SEQUENCE CHARACTERISTICS:
        ( A ) LENGTH: 6 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:49:

```
Xaa  Leu  Asp  Xaa  Xaa  Trp
1                   5
```

( 2 ) INFORMATION FOR SEQ ID NO:50:

( i ) SEQUENCE CHARACTERISTICS:
        ( A ) LENGTH: 6 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:50:

```
Xaa  Arg  Asp  Xaa  Xaa  Trp
1                   5
```

( 2 ) INFORMATION FOR SEQ ID NO:51:

( i ) SEQUENCE CHARACTERISTICS:
        ( A ) LENGTH: 6 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:51:

```
Xaa  Lys  Asp  Xaa  Xaa  Trp
1                   5
```

( 2 ) INFORMATION FOR SEQ ID NO:52:

( i ) SEQUENCE CHARACTERISTICS:
        ( A ) LENGTH: 6 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:52:

```
Xaa  Xaa  Asp  Xaa  Xaa  Trp
1                   5
```

( 2 ) INFORMATION FOR SEQ ID NO:53:

( i ) SEQUENCE CHARACTERISTICS:
        ( A ) LENGTH: 6 amino acids
        ( B ) TYPE: amino acid
        ( C ) STRANDEDNESS: single ( D ) TOPOLOGY: linear ( i i ) MOLECULE TYPE: peptide ( x i ) SEQUENCE DESCRIPTION: SEQ ID NO:53:

Xaa Asp Asp Xaa Xaa Trp
1               5

( 2 ) INFORMATION FOR SEQ ID NO:54:

( i ) SEQUENCE CHARACTERISTICS:
( A ) LENGTH: 6 amino acids
( B ) TYPE: amino acid
( C ) STRANDEDNESS: single
( D ) TOPOLOGY: linear ( i i ) MOLECULE TYPE: peptide ( x i ) SEQUENCE DESCRIPTION: SEQ ID NO:54:

Xaa Glu Asp Xaa Xaa Trp
1               5

( 2 ) INFORMATION FOR SEQ ID NO:55:

( i ) SEQUENCE CHARACTERISTICS:
( A ) LENGTH: 6 amino acids
( B ) TYPE: amino acid
( C ) STRANDEDNESS: single
( D ) TOPOLOGY: linear ( i i ) MOLECULE TYPE: peptide ( x i ) SEQUENCE DESCRIPTION: SEQ ID NO:55:

Xaa Leu Asn Ile Xaa Trp
1               5

( 2 ) INFORMATION FOR SEQ ID NO:56:

( i ) SEQUENCE CHARACTERISTICS:
( A ) LENGTH: 6 amino acids
( B ) TYPE: amino acid
( C ) STRANDEDNESS: single
( D ) TOPOLOGY: linear ( i i ) MOLECULE TYPE: peptide ( x i ) SEQUENCE DESCRIPTION: SEQ ID NO:56:

Xaa Leu Asp Phe Xaa Trp
1               5

( 2 ) INFORMATION FOR SEQ ID NO:57:

( i ) SEQUENCE CHARACTERISTICS:
( A ) LENGTH: 6 amino acids
( B ) TYPE: amino acid
( C ) STRANDEDNESS: single
( D ) TOPOLOGY: linear ( i i ) MOLECULE TYPE: peptide ( x i ) SEQUENCE DESCRIPTION: SEQ ID NO:57:

Xaa Xaa Asp Phe Xaa Trp
1               5

( 2 ) INFORMATION FOR SEQ ID NO:58:

( i ) SEQUENCE CHARACTERISTICS:
( A ) LENGTH: 6 amino acids
( B ) TYPE: amino acid
( C ) STRANDEDNESS: single (D) TOPOLOGY: linear (i i) MOLECULE TYPE: peptide (x i) SEQUENCE DESCRIPTION: SEQ ID NO:58:

```
Xaa  Lys  Asp  Phe  Xaa  Trp
1                  5
```

(2) INFORMATION FOR SEQ ID NO:59:

(i) SEQUENCE CHARACTERISTICS:
 (A) LENGTH: 6 amino acids
 (B) TYPE: amino acid
 (C) STRANDEDNESS: single
 (D) TOPOLOGY: linear (i i) MOLECULE TYPE: peptide (x i) SEQUENCE DESCRIPTION: SEQ ID NO:59:

```
Xaa  Asp  Asp  Phe  Xaa  Trp
1                  5
```

(2) INFORMATION FOR SEQ ID NO:60:

(i) SEQUENCE CHARACTERISTICS:
 (A) LENGTH: 6 amino acids
 (B) TYPE: amino acid
 (C) STRANDEDNESS: single
 (D) TOPOLOGY: linear (i i) MOLECULE TYPE: peptide (x i) SEQUENCE DESCRIPTION: SEQ ID NO:60:

```
Xaa  Glu  Asp  Phe  Xaa  Trp
1                  5
```

(2) INFORMATION FOR SEQ ID NO:61:

(i) SEQUENCE CHARACTERISTICS:
 (A) LENGTH: 6 amino acids
 (B) TYPE: amino acid
 (C) STRANDEDNESS: single
 (D) TOPOLOGY: linear (i i) MOLECULE TYPE: peptide (x i) SEQUENCE DESCRIPTION: SEQ ID NO:61:

```
Xaa  Phe  Asp  Phe  Xaa  Trp
1                  5
```

(2) INFORMATION FOR SEQ ID NO:62:

(i) SEQUENCE CHARACTERISTICS:
 (A) LENGTH: 6 amino acids
 (B) TYPE: amino acid
 (C) STRANDEDNESS: single
 (D) TOPOLOGY: linear (i i) MOLECULE TYPE: peptide (x i) SEQUENCE DESCRIPTION: SEQ ID NO:62:

```
Xaa  Arg  Asp  Phe  Xaa  Trp
1                  5
```

(2) INFORMATION FOR SEQ ID NO:63:

(i) SEQUENCE CHARACTERISTICS:
 (A) LENGTH: 6 amino acids
 (B) TYPE: amino acid
 (C) STRANDEDNESS: single (D) TOPOLOGY: linear (ii) MOLECULE TYPE: peptide (xi) SEQUENCE DESCRIPTION: SEQ ID NO:63:

```
Xaa Leu Asp Phe Xaa Trp
1               5
```

(2) INFORMATION FOR SEQ ID NO:64:

(i) SEQUENCE CHARACTERISTICS:
(A) LENGTH: 6 amino acids
(B) TYPE: amino acid
(C) STRANDEDNESS: single
(D) TOPOLOGY: linear (ii) MOLECULE TYPE: peptide (xi) SEQUENCE DESCRIPTION: SEQ ID NO:64:

```
Xaa Arg Asp Ile Ile Xaa
1               5
```

ENDOTHELIN ANTAGONISTS II

This is a continuation-in-part application of U.S. application Ser. No. 08/033,515 filed Mar. 31, 1993, now abandoned, which is a continuation-in-part application of U.S. application Ser. No. 07/872,225 filed Apr. 22, 1992, now abandoned.

BACKGROUND OF THE INVENTION

The present invention relates to novel antagonists of endothelin useful as pharmaceutical agents, to methods for their production, to pharmaceutical compositions which include these compounds and a pharmaceutically acceptable carrier, and to pharmaceutical methods of treatment. More particularly, the novel compounds of the present invention are antagonists of endothelin useful in treating elevated levels of endothelin, acute and chronic renal failure, hypertension, myocardial infarction, metabolic, endocrinological and neurological disorders especially cerebral vasospasm, stroke, and head injury, congestive heart failure, endotoxic shock, subarachnoid hemorrhage, arrhythmias, asthma, preeclampsia, atherosclerotic disorders including Raynaud's disease, restenosis, angina, cancer, pulmonary hypertension, ischemic disease, gastric mucosal damage, hemorrhagic shock, ischemic bowel disease, and diabetes.

Endothelin-1 (ET-1), a potent vasoconstrictor, is a 21 amino acid bicyclic peptide that was first isolated from cultured porcine aortic endothelial cells. Endothelin-1, is one of a family of structurally similar bicyclic peptides which include; ET-2, ET-3, vasoactive intestinal contractor (VIC), and the sarafotoxins (SRTXs). The unique bicyclic structure and corresponding arrangement of the disulfide bridges of ET-1, which are the same for the endothelins, VIC, and the sarafotoxins, has led to significant speculation as to the importance of the resulting induced secondary structure to receptor binding and functional activity. ET-1 analogues with incorrect disulfide pairings exhibit at least 100-fold less vasoconstrictor activity. The flexible C-terminal hexapeptide of ET-1 has been shown to be important for binding to the ET receptor and functional activity in selected tissues. Additionally, the C-terminal amino acid (Trp-21) has a critical role in binding and vasoconstrictor activity, since ET[1–20] exhibits approximately 1000-fold less functional activity.

Endothelin is involved in many human disease states.

Several in vivo studies with ET antibodies have been reported in disease models. Left coronary artery ligation and reperfusion to induce myocardial infarction in the rat heart, caused a four- to seven-fold increase in endogenous endothelin levels. Administration of ET antibody was reported to reduce the size of the infarction in a dose-dependent manner (Watanabe T., et al., "Endothelin in Myocardial Infarction," *Nature* (Lond.), 344:114 (1990)). Thus, ET may be involved in the pathogenesis of congestive heart failure and myocardial ischemia (Margulies K. B., et al., "Increased Endothelin in Experimental Heart Failure," *Circulation*, 82:2226 (1990)).

Studies by Kon and colleagues using anti-ET antibodies in an ischemic kidney model, to deactivate endogenous ET, indicated the peptide's involvement in acute renal ischemic injury (Kon V., et al., "Glomerular Actions of Endothelin In Vivo," *J. Clin. Invest.*, 83:1762 (1989)). In isolated kidneys, preexposed to specific antiendothelin antibody and then challenged with cyclosporine, the renal perfusate flow and glomerular filtration rate increased, while renal resistance decreased as compared with isolated kidneys preexposed to a nonimmunized rabbit serum. The effectiveness and specificity of the anti-ET antibody were confirmed by its capacity to prevent renal deterioration caused by a single bolus dose (150 pmol) of synthetic ET, but not by infusion of angiotensin II, norepinephrine, or the thromboxane $A_2$ mimetic U-46619 in isolated kidneys (Perico N., et al., "Endothelin Mediates the Renal Vasoconstriction Induced by Cyclosporine in the Rat," *J. Am. Soc. Nephrol,*, 1:76 (1990)).

Others have reported inhibition of ET-1 or ET-2-induced vasoconstriction in rat isolated thoracic aorta using a monoclonal antibody to ET-1 (Koshi T., et al., "Inhibition of Endothelin (ET)-1 and ET-2-Induced Vasoconstriction by Anti-ET-1 Monoclonal Antibody," *Chem. Pharm. Bull.*, 39:1295 (1991)).

Combined administration of ET-1 and ET-1 antibody to rabbits showed significant inhibition of the blood pressure (BP) and renal blood flow responses (Miyamori I., et al., "Systemic and Regional Effects of Endothelin in Rabbits: Effects of Endothelin Antibody," *Clin. Exp. Pharmacol. Physiol.*, 17:691 (1990)).

Other investigators have reported that infusion of ET-specific antibodies into spontaneously hypertensive rats (SHR) decreased mean arterial pressure (MAP), and increased glomerular filtration rate and renal blood flow. In the control study with normotensive Wistar-Kyoto rats (WKY) there were no significant changes in these parameters (Ohno A., "Effects of Endothelin-Specific Antibodies and Endothelin in Spontaneously Hypertensive Rats," *J. Tokyo Women's Med. Coll.*, 61:951 (1991)).

In addition, elevated levels of endothelin have been reported in several disease states (see Table I below).

Burnett and co-workers recently demonstrated that exogenous infusion of ET (2.5 ng/kg/mL) to anesthetized dogs, producing a doubling of the circulating concentration, did have biological actions (Lerman A., et al., "Endothelin has Biological Actions at Pathophysiological Concentrations," *Circulation*, 83:1808 (1991)). Thus heart rate and cardiac output decreased in association with increased renal and systemic vascular resistances and antinatriuresis. These studies support a role for endothelin in the regulation of cardiovascular, renal, and endocrine function.

In the anesthetized dog with congestive heart failure, a significant two- to three-fold elevation of circulating ET levels has been reported (Cavero P. G., et al., "Endothelin in Experimental Congestive Heart Failure in the Anesthetized Dog," *Am. J. Physiol.*, 259:F312 (1990)), and studies in humans have shown similar increases (Rodeheffer R. J., et al., "Circulating Plasma Endothelin Correlates With the Severity of Congestive Heart Failure in Humans," *Am. J. Hypertension*, 4:9A (1991)). When ET was chronically infused into male rats, to determine whether a long-term increase in circulating ET levels would cause a sustained elevation in mean arterial blood pressure, significant, sustained, and dose-dependent increases in mean arterial BP were observed. Similar results were observed with ET-3 although larger doses were required (Mortenson L. H., et al., "Chronic Hypertension Produced by Infusion of Endothelin in Rats," *Hypertension*, 15:729 (1990)).

The distribution of the two cloned receptor subtypes, termed $ET_A$ and $ET_B$, have been studied extensively (Arai H., et al., *Nature*, 348:730 (1990), Sakurai T., et al., *Nature*, 348:732 (1990)). The $ET_A$, or vascular smooth muscle receptor, is widely distributed in cardiovascular tissues and in certain regions of the brain (Lin H. Y., et al., *Proc. Natl. Acad. Sci.*, 88:3185 (1991)). The $ET_B$ receptor, originally cloned from rat lung, has been found in rat cerebellum and in endothelial cells, although it is not known if the $ET_B$ receptors are the same from these sources. The human ET receptor subtypes have been cloned and expressed (Sakamoto A., et al., *Biochem. Biophys. Res. Chem.*, 178:656 (1991), Hosoda K., et al., *FEBS Lett.*, 287:23 (1991)). The $ET_A$ receptor clearly mediates vasoconstriction and there have been a few reports implicating the $ET_B$ receptor in the initial vasodilatory response to ET (Takayanagi R., et al., *FEBS Lett.*, 282:103 (1991)). However, recent data has shown that the $ET_B$ receptor can also mediate vasoconstriction in some tissue beds (Panek R. L., et al., *Biochem. Biophys. Res. Commun.*, 183(2):566 (1992)).

Comparison of the receptor affinities of the ETs and SRTXs in rats and atria ($ET_A$) or cerebellum and hippocampus ($ET_B$), indicate that SRTX-c is a selective $ET_B$ ligand (Williams D. L., et al., *Biochem. Biophys. Res. Commun.*, 175:556 (1991)). A recent study showed that selective $ET_B$ agonists caused only vasodilation in the rat aortic ring, possibly through the release of EDRF from the endothelium (ibid). Thus, reported selective $ET_B$ agonists, for example, the linear analog ET[1,3,11,15-Ala] and truncated analogs ET[6–21, 1,3,11,15-Ala] , ET[8–21,11,15-Ala] , and N-Acetyl-ET[10–21,11,15-Ala] caused vasorelaxation in isolated, endothelium-intact porcine pulmonary arteries (Saeki T., et al., *Biochem. Biophys. Res. Commun.*, 179:286 (1991)). However, some ET analogs are potent vasoconstrictors in the rabbit pulmonary artery, a tissue that appears to possess an $ET_B$ y, nonselective type of receptor (ibid).

Plasma endothelin-1 levels were dramatically increased in a patient with malignant hemangioendothelioma (Nakagawa K., et al., *Nippon Hifuka Gakkai Zasshi*, 100:1453–1456 (1990)).

The ET receptor antagonist BQ-123 has been shown to block ET-1 induced bronchoconstriction and tracheal smooth muscle contraction in allergic sheep providing evidence for expected efficacy in bronchopulmonary diseases such as asthma (Noguchi, et al., *Am. Rev. Respir. Dis.* 415(4 Part 2):A858 (1992)).

Circulating endothelin levels are elevated in women with preeclampsia and correlate closely with serum uric acid levels and measures of renal dysfunction. These observations indicate a role for ET in renal constriction in preeclampsia (Clark B. A., et al., *Am. J. Obstet. Gynecol.*, 166:962–968 (1992)).

Plasma immunoreactive endothelin-1 concentrations are elevated in patients with sepsis and correlate with the degree of illness and depression of cardiac output (Pittett J., et al., *Ann Surg.*, 213(3):262 (1991)).

In addition the ET-1 antagonist BQ-123 has been evaluated in a mouse model of endotoxic shock. This $ET_A$ antagonist significantly increased the survival rate in this model (Toshiaki M., et al., 20.12.90. EP 0 436 189 A1).

Endothelin is a potent agonist in the liver eliciting both sustained vasoconstriction of the hepatic vasculature and a significant increase in hepatic glucose output (Gandhi C. B., et al., *Journal of Biological Chemistry*, 265(29):17432 (1990)). In streptozotocin-diabetic rats there is an increased sensitivity to endothelin-1 (Tammesild P. J., et al., *Clin. Exp. Pharmacol. Physiol.*, 19(4):261 (1992)). In addition increased levels of plasma ET-1 have been observed in microalbuminuric insulin-dependent diabetes mellitus patients indicating a role for ET in endocrine disorders such as diabetes (Collier A., et al., *Diabetes Care*, 15(8):1038 (1992)).

$ET_A$ antagonist receptor blockade has been found to produce an antihypertensive effect in normal to low renin models of hypertension with a time course similar to the inhibition of ET-1 pressor responses (Basil M. K., et al., *J. Hypertension*, 10(Suppl. 4):S49 (1992)). The endothelins have been shown to be arrhythmogenic, and to have positive chronotropic and inotropic effects, thus ET receptor blockade would be expected to be useful in arrhythmia and other cardiovascular disorders (Hah S.-P., et al., *Life Sci.*, 46:767 (1990)).

The widespread localization of the endothelins and their receptors in the central nervous system and cerebrovascular circulation has been described (Nikolov R. K., et al., *Drugs of Today*, 28(5):303–310 (1992)). Intracerebroventricular administration of ET-1 in rats has been shown to evoke several behavioral effects. These factors strongly suggest a role for the ETs in neurological disorders. The potent vasoconstrictor action of ETs on isolated cerebral arterioles suggests the importance of these peptides in the regulation of cerebrovascular tone. Increased ET levels have been reported in some CNS disorders, i.e., in the CSF of patients with subarachnoid hemorrhage and in the plasma of women with preeclampsia. Stimulation with ET-3 under conditions of hypoglycemia have been shown to accelerate the development of striatal damage as a result of an influx of extracellular calcium. Circulating or locally produced ET has been suggested to contribute to regulation of brain fluid balance through effects on the choroid plexus and CSF production. ET-1 induced lesion development in a new model of local ischemia in the brain has been described.

Circulating and tissue endothelin immunoreactivity is increased more than twofold in patients with advanced atherosclerosis (Lerman A., et al., *New England J. Med.*, 325:997–1001 (1991)). Increased endothelin immunoreactivity has also been associated with Buerger's disease (Kanno K., et al., *J. Amer. Med. Assoc.*, 264:2868 (1990)) and Raynaud's phenomenon (Zamora M. R., et al., *Lancet*, 336:1144–1147 (1990)). Likewise, increased endothelin concentrations were observed in hypercholesterolemic rats (Horio T., et al., *Atherosclerosis*, 89:239–245 (1991)).

An increase of circulating endothelin levels was observed in patients that underwent percutaneous transluminal coronary angioplasty (PTCA) (Tahara A., et al., *Metab. Clin. Exp.*, 40:1235–1237 (1991) , Sanjay K., et al., *Circulation*, 84(Suppl. 4):726 (1991)).

Increased plasma levels of endothelin have been measured in rats (Stelzner T. J., et al., *Am. J. Physiol.*, 262:L614-L620 (1992)) and individuals (Miyauchi T., et al., *Jpn. J. Pharmacol.*, 58:279P (1992) and Stewart D. J., et al., *Ann. Internal Medicine*, 114:464–469 (1991)) with pulmonary hypertension.

Elevated levels of endothelin have also been measured in patients suffering from ischemic heart disease (Yasuda M., et al., *Amer. Heart J.*, 119:801–806 (1990), Ray S. G., et al., *Br. Heart J.*, 67:383–386 (1992)) and either stable or unstable angina (Stewart J. T., et al., *Br. Heart J.*, 66.:7–9 (1991)).

Infusion of an endothelin antibody 1 hour prior to and 1 hour after a 60 minute period of renal ischaemia resulted in changes in renal function versus control. In addition, an increase in glomerular platelet-activating factor was attributed to endothelin (Lopez-Farre A., et al., *J. Physiology*, 444:513–522 (1991)). In patients with chronic renal failure as well as in patients on regular hemodialysis treatment, mean plasma endothelin levels were significantly increased (Stockenhuber F., et al., *Clin. Sci. (Lond.)*, 82:255–258 (1992)). In addition, it has been suggested that the proliferative effect of endothelin on mesangial cells may be a contributing factor in chronic renal failure (Schultz P. J., *J. Lab. Clin. Med.*, 119:448–449 (1992,).

Local intra-arterial administration of endothelin has been shown to induce small intestinal mucosal damage in rats in a dose-dependent manner (Mirua S., et al., *Digestion*, 48:163–172 (1991)). Administration of endothelin-1 in the range of 50–500 pmol/kg into the left gastric artery increased the tissue type plasminogen activator release and platelet activating formation, and induced gastric mucosal hemorrhagic change in a dose dependent manner (Kurose I., et al., *Gut*, 33:868–871 (1992)). Furthermore, it has been shown that an anti-ET-1 antibody reduced ethanol-induced vasoconstriction in a concentration-dependent manner (Masuda E., et al., *Am. J. Physiol.*, 262:G785-G790 (1992)). Elevated endothelin levels have been observed in patients suffering from Crohn's disease and ulcerative colitis (Murch S. H., et al., *Lancet*, 339:381–384 (1992)).

The role of endothelins (ET-1, -2, -3) in various physiological and pathophysiological conditions has been studied extensively (Doherty A. D., Endothelin: A New Challenge, *J. Med. Chem,*, 35:1493 (1992); Simonson M. S., Endothelins: Multifunctional Renal Peptides, *Physiological Reviews* 79:375 (1993)). These peptides act via their receptors viz. $ET_A$ and $ET_B$, which have been cloned and expressed. $ET_A$ specific antagonists have been identified viz. BQ123 (Ishikawa K.; Fukami T., et al., Cyclic pentapeptide endothelin antagonists with high $ET_A$ selectivity, Potency- and solubility-enhancing modifications, *J. Med. Chem.*, 35:2139 (1992); Kiyofumi I., et al., Endothelin antagonistic cyclic pentapeptides. EPA 0436 189 A1 published Jul. 10, 1991), BMS182874 (Stein P. D., et al., Sulfonamide endothelin antagonists. EP 0558258 A1, published Sep. 1, 1993) and FR 139317 (Keiji H., et al., Peptides having endothelin antagonist activity, a process for the preparation thereof and pharmaceutical compositions comprising the same. EP 0457195 A2, published Nov. 21, 1991). Several non-selective $ET_A/ET_B$ antagonists have also been identified including PD 142893 (Cody W. L., et al., Design of a functional hexapeptide antagonist of endothelin, *J. Med. Chem.*, 35:3301 (1992); Doherty A. M., et al., Structure-activity relationships of C-terminal endothelin hexapeptide antagonists, *J. Med. Chem.*, 36:2585 (1993)), PD 145065 (Cody W. L., et al., The rational design of a highly potent combined $ET_A$ and $ET_B$ receptor antagonist (PD 145065) and related analogues, *Med. Chem. Res.*, 3:154 (1993); Doherty A. M., et al., In vitro and in vivo studies with a series of hexapeptide endothelin antagonists, *J. Cardiovasc. Pharmacol.* 1993, in press), Ro 46-2005 (Burri K., et al., Application of sulfonamides as therapeutics and new sulfonamides. EP 0510526 A1, published Oct. 28, 1992; Clozel M., et al., The discovery of Ro 46-2005, an orally available non-peptide antagonist of $ET_A$ and $ET_B$ receptors. 3rd International Endothelin Symposium, Houston, Tex., February 1993; Clozel M., et al., Pathophysiological role of endothelin revealed by the first orally active endothelin receptor antagonist, *Nature*, 365:759 (1993)), and Ro 47-0203 (Roux S. P., et al., Ro 47-0203, a new endothelin receptor antagonist reverses chronic vasospasm in experimental subarachnoid hemorrhage, *Circulation*, 4(Part 2, Supplement):I-170 (1993)). These antagonists have blocked the vasoconstrictive effects of ET peptides in several in vivo disease models.

For example, BQ123 has been effective in antagonizing the ET-1 induced pressor response in conscious rats (Ihara M., et al., In vitro biological profile of highly potent novel endothelin (ET) antagonist BQ-123 selective for the $ET_A$ receptor, *J. Cardiovasc. Pharmacol.*, 20(S12):S11 (1992); Ihara M., et al., Biological profiles of highly potent novel endothelin antagonists selective for the $ET_A$ receptor, *Life Sci.*, 50:247 (1992)). Intravenous infusion of BQ123 decreased blood pressure significantly in stroke prone spontaneous hypertensive rats and was effective in the prevention of acute hypoxia induced pulmonary hypertension (McMahon E. G., et al., Effect of phosphoramidon (endothelin converting enzyme inhibitor) and BQ-123 (Endothelin receptor subtype-A antagonist) on blood pressure in hypertensive rats, *Am. J. Hypertension*, 6:667 (1993)). ET-1 induced vasoconstriction in rabbit retinal arteries and the renal vascular resistance in rats was blocked by i.v. BQ123 (Takei K., et al., Analysis of vasocontractile response to endothelin-1 in rabbit retinal vessels using an $ET_A$ receptor antagonist and an $ET_B$ receptor agonist, *Life Sci.*, 53:PL111 (1993)). Cyclosporine A (CsA) induced ET-1 release in vivo (Fogo A., et al., Severe endothelial injury in a renal transplant patient receiving cyclosporine, *Transplantation*, 49:1190 (1990); Watschinger B., et al., Cyclosporine A toxicity is associated with reduced endothelin immunoreactivity in renal endothelium, *Transplant. Proc.*, 24:2618 (1992); Awazu M., et al., Cyclosporine promotes glomerular endothelin binding in vivo, *J. Am. Soc. Nephrol.*, 1:1253 (1991); Bloom I. T., et al., Acute cyclosporine-induced renal vasoconstriction is mediated by endothelin-1, *Surgery*, 114:480 (1993)), which caused renal vasoconstriction (Kon V. and Awazu M., Endothelin and cyclosporine nephrotoxicity, *Renal Fall.*, 14:345 (1992); Brooks D. P., et al., Effect of nifedipine on cyclosporine A-induced nephrotoxicity, urinary endothelin excretion and renal endothelin receptor number, *Eur. J. Pharmacol.*, 194:115 (1991,). This acute CsA toxicity was suppressed by BQ123 in a rat model (Fogo A., et al., Endothelin receptor antagonism is protective in in vivo acute cyclosporin toxicity, *Kidney Int.*, 42:770 (1992)). BQ123 (i.v.) prevents the mitochondrial $[Ca^{2+}]$ accumulation in the early phase of ischemic acute renal failure in rats and protects proximal tubular cells from post-ischemic degeneration suggesting possible involvement of endothelin in the pathogenesis of tubular cell injury in the acute ischemic renal failure model (Mino N., et al., Protective effect of a selective endothelin receptor antagonist, BQ-123, in ischemic acute renal failure in rats, *Eur. J. Pharmacol.*, 221:77 (1992)).

Intraperitoneal administration of FR 139317 in rats reduced abnormal permeability to proteins and limited glomerular injury and prevented renal function deterioration. Intracisternal administration of FR 139317 significantly reduced the vasoconstriction of the basilar artery in canine subarachnoid hemorrhage model (Nirei H., et al., An endothelin $ET_A$ receptor antagonist FR 139317 ameliorates cerebral vasospasm in dogs, *Life Sci.*, 52:1869 (1993)). ET-1 induced arrhythmia in rats (Sogabe K., et al., Pharmacological profile of FR 139317, a novel, potent endothelin $ET_A$ receptor antagonist, *J. Pharmacol. Exp. Ther.*, 264:1040 (1993)) was also suppressed by FR 139317.

Non-selective $ET_A/ET_B$ antagonists like PD 145065 and PD 142893 antagonized both pressor and depressor responses induced by ET-1 in a dose-dependent manner in anesthetized ganglionic blocked rats (Doherty A. M., et al., In vitro and in vivo studies with a series of hexapeptide endothelin antagonists, *J. Cardiovasc. Pharmacol.*, 1993, in press). ET-1 induced reductions in renal flow in anesthetized rats (Wellings R. P., et al., Vasoconstriction in the rat kidney induced by endothelin-1 is blocked by PD 145065, Third International Conference on Endothelin, Houston, Feb. 15–17, 1993, Abstract 139) was completely inhibited by prior administration of PD 145065. In anesthetized guinea pig PD 145065 blocked the increase in pulmonary insufflation pressure induced by ET-1 (Warner T. D., et al., Inhibition by a non-selective endothelin receptor antagonist of bronchoconstrictions induced by endothelin-1 or sarafotoxin 6c in the anesthetized guinea pig, *Br. J. Pharmacol.* in press). Ro 46-2005 demonstrated a protective effect for renal vasoconstriction after renal ischemia in anesthetized rats and also dramatically reduced cerebral vasoconstriction after subarachnoid hemorrhage in rats. Orally administered Ro 46-2005 showed marked antihypertensive effect with a reasonably long duration (Clozel M., et al., The discovery of Ro 46-2005, an orally available non-peptide antagonist of $ET_A$ and $ET_B$ receptors, Third International Endothelin Symposium, Houston, Tex., February 1993; Clozel M., et al., Pathophysiological role of endothelin revealed by the first orally active endothelin receptor antagonist, *Nature*, 365:759 (1993)). Ro 47-0203 was effective in a rabbit subarachnoid hemorrhage model in reversing vasoconstriction indicating that this compound crosses the blood brain barrier (Roux S. P., et al., Ro 47-0203, a new endothelin receptor antagonist reverses chronic vasospasm in experimental subarachnoid hemorrhage, *Circulation*, 4(Part 2, supplement):I-170 (1993)). Ro 47-203 is reported to be in early clinical trials for SAH and hypertension (Roux S. P., et al., Ro 47-0203, a new endothelin receptor antagonist reverses chronic vasospasm in experimental subarachnoid hemorrhage, *Circulation*, 4(Part 2, Supplement):I-170 (1993)).

TABLE I

Plasma Concentrations of ET-1 in Humans

| Condition | Normal Control | RT Plasma Levels Report (pg/ml) |
|---|---|---|
| Atherosclerosis | 1.4 | 3.2 pmol/L |
| Surgical operation | 1.5 | 7.3 |
| Buerger's disease | 1.6 | 4.8 |
| Takayaou's arteritis | 1.6 | 5.3 |
| Cardiogenic shock | 0.3 | 3.7 |
| Congestive heart failure (CHF) | 9.7 | 20.4 |
| Mild CHF | 7.1 | 11.1 |
| Severe CHP | 7.1 | 13.8 |
| Dilated cardiomyopathy | 1.6 | 7.1 |
| Preeclampsia | 10.4 pmol/L | 22.6 pmol/L |
| Pulmonary hypertension | 1.45 | 3.5 |
| Acute myocardial infarction | 1.5 | 3.3 |
| (several reports) | 6.0 | 11.0 |
| | 0.76 | 4.95 |
| | 0.50 | 3.8 |
| Subarachnoid hemorrhage | 0.4 | 2.2 |
| Crohn's Disease | 0–24 fmol/mg | 4–64 fmol/mg |
| Ulcerative colitis | 0–24 fmol/mg | 20–50 fmol/mg |
| Cold premoor test | 1.2 | 8.4 |
| Raynaud's phenomenon | 1.7 | 5.3 |
| Raynaud's/hand cooling | 2.8 | 5.0 |
| Hemodialysis | <7 | 10.9 |
| (several reports) | 1.88 | 4.59 |
| Chronic renal failure | 1.88 | 10.1 |
| Acute renal failure | 1.5 | 10.4 |
| Uremia before hemodialysis | 0.96 | 1.49 |
| Uremia after hemodialysis | 0.96 | 2.19 |
| Essential hypertension | 18.5 | 33.9 |
| Sepois syndrome | 6.1 | 19.9 |
| Postoperative cardiac | 6.1 | 11.9 |
| Inflammatory arthritides | 1.5 | 4.2 |
| Malignant hemangioendothelioma | 4.3 (after removal) | 16.2 |

Rovero P., et al., *British Journal of Pharmacology*, 101:232–236 (1990) disclosed various analogs of the C-terminal hexapeptide of ET-1, none of which were reported to be antagonists of ET-1.

Doherty A. M., et al., Abstract, Second International Conference on Endothelin, Tsukuba, Japan, Dec. 9, 1990, and the published manuscript (*J. Cardiovasc. Pharm.*, 17(Suppl. 7):559–561 (1991), disclosed various analogs of the C-terminal hexapeptide of ET-1, none of which exhibited any functional activity.

Copending U.S. patent application Ser. No. 07/995,480 now U.S. Pat. No. 5,382,569 discloses a series of novel antagonists of endothelin.

However, we have surprisingly and unexpectedly found that a series of C-terminal hexapeptide and related analogs of ET-1 are receptor antagonists of endothelin. Additional data for the activity of this series of peptides is found in the following references (Cody W. L., et al., *J. Med. Chem.*, 35:3301–3303 (1992), LaDouceur D. M., et al., FASEB (1992)).

SUMMARY OF THE INVENTION

Accordingly, the present invention is a compound of Formula I

   Seq. ID No:1 wherein $AA^1$ is

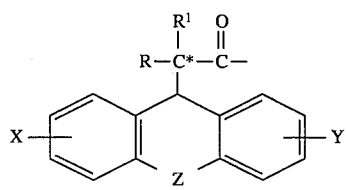

wherein R is hydrogen,
alkyl,
alkenyl,
alkynyl,
cycloalkyl,
cycloalkylalkyl,
aryl,
heteroaryl,
fluorenylmethyl,

wherein $R^2$ and $R^2$ are each the same or different and each is
hydrogen,
alkyl,
alkenyl,
alkynyl,
cycloalkyl,
cycloalkylalkyl,
aryl,
arylalkyl,
heteroaryl, or
fluorenylmethyl, $$-\overset{O}{\underset{\|}{C}}-OR^2,$$

wherein $R^2$ is as defined above,

—OR², wherein R² is as defined above,

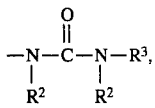

wherein R² and R³ are as defined above,

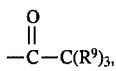

wherein R⁹ is F, Cl, Br, or I,
—CH₂—OR², wherein R² is as defined above,

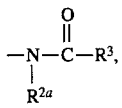

wherein $R^{2a}$ is hydrogen or alkyl and R³ is as defined above,

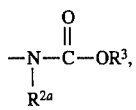

wherein $R^{2a}$ and R³ are as defined, above excluding R³ is hydrogen or

wherein R² is as defined above,
R¹ is hydrogen or alkyl,
Z is —O—,
—S(O)ₘ—, wherein m is zero or an integer of 1 or 2,

wherein R² is as defined above,
—(CH₂)ₙ—, wherein n is zero or an integer of 1, 2, 3, or 4,
—(CH₂)ₙ—CH=CH—(CH₂)ₙ'—, wherein n and n' are each independently the same or different and each is as defined above for n,

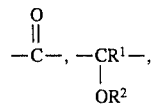

wherein R¹ and R² are as defined above, or

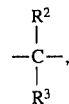

wherein R² and R³ are each the same or different and each is as defined above,

X and Y are the same and substituted at the same position on the aromatic ring and each may be 1, 2, 3, or 4 substituents selected from the group consisting of
hydrogen,
halogen,
alkyl,
—CO₂R², wherein R² is as defined above,

wherein R² and R³ are as defined above,

wherein R² and R³ are as defined above, or
nitro or

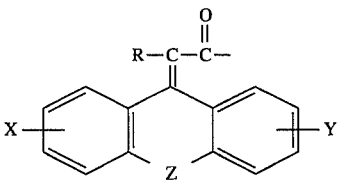

wherein R, Z, X, and Y are as defined above;
AA² is

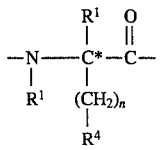

wherein R⁴ is
hydrogen,
alkyl,
alkenyl,
alkynyl,
cycloalkyl,
aryl,
heteroaryl,

wherein $R^{2b}$ and $R^{3b}$ are each the same or different and each is
hydrogen,
alkyl,
cycloalkyl,
aryl, or
heteroaryl,
—$OR^{2b}$, wherein $R^{2b}$ is as defined above,

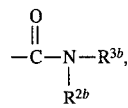

wherein $R^{2b}$ and $R^{3b}$ are each the same or different and each is as defined above for $R^{2b}$ and $R^{3b}$,

wherein $R^{2b}$ is as defined above,

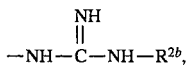

wherein $R^{2b}$ is as defined above, or

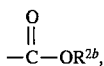

wherein $R^{2b}$ is as defined above, and $R^1$ and n are as defined above, or $AA^2$ is absent; $AA^3$ is

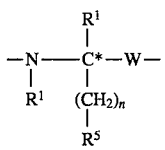

wherein W is

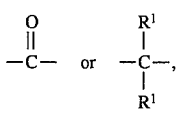

$R^5$ is
hydrogen,
alkyl,
aryl,
heteroaryl,

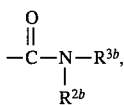

wherein $R^{2b}$ and $R^{3b}$ are each the same or different and each is as defined above,

wherein $R^{2b}$ is as defined above, or

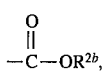

wherein $R^{2b}$ is as defined above, and $R^1$ and n are as defined above, or $AA^3$ is absent; $AA^4$ and $AA^5$ are each independently absent or each is independently

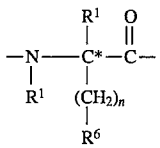

wherein $R^6$ is hydrogen,
alkyl,
alkenyl,
alkynyl,
cycloalkyl,
aryl, or
heteroaryl, and
$R^1$ and n are as defined above;
$AA^6$ is

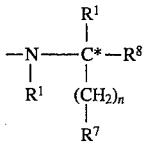

wherein $R^7$ is
aryl or
heteroaryl,
$R^8$ is

wherein $R^1$ is as defined above,
—$OR^1$, wherein $R^1$ is as defined above,

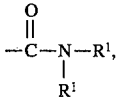

wherein $R^1$ is as defined above, or
—$CH_2$—$OR^1$, wherein $R^1$ is as defined above, and
$R^1$ and n are as defined above;
stereochemistry at C* in $AA^1$, $AA^2$, $AA^3$, $AA^4$, or $AA^5$ is D, L, or DL and stereochemistry at C* in $AA^6$ is L; or a pharmaceutically acceptable salt thereof.

Elevated levels of endothelin have been postulated to be involved in a number of pathophysiological states including diseases associated with the cardiovascular system as well as various metabolic and endocrinological disorders. As antagonists of endothelin, the compounds of Formula I are useful in the treatment of hypertension, myocardial infarction, metabolic, endocrinological and neurological disorders especially cerebral vasospasm, stroke, and head injury, congestive heart failure, endotoxic shock, subarachnoid hemorrhage, arrhythmias, asthma, and chronic and acute renal failure, preeclampsia, atherosclerotic disorders including Raynaud's disease, restenosis, angina, cancer, pulmonary hypertension, ischemic disease, gastric mucosal damage, hemorrhagic shock, ischemic bowel disease, and diabetes.

A still further embodiment of the present invention is a pharmaceutical composition for administering an effective amount of a compound of Formula I in unit dosage form in the treatment methods mentioned above.

Finally, the present invention is directed to methods for production of a compound of Formula I.

DETAILED DESCRIPTION OF THE INVENTION

In the compounds of Formula I, the term "alkyl" means a straight or branched hydrocarbon radical having from 1 to 12 carbon atoms and includes, for example, methyl, ethyl, n-propyl, isopropyl, n-butyl, sec-butyl, isobutyl, tert-butyl, n-pentyl, n-hexyl, n-heptyl, n-octyl, n-nonyl, n-decyl, undecyl, dodecyl, and the like.

The term "alkenyl" means a straight or branched unsaturated hydrocarbon radical having from 2 to 12 carbon atoms and includes, for example, ethenyl, 2-propenyl, 1-butenyl, 2-butenyl, 1-pentenyl, 2-pentenyl, 3-methyl-3-butenyl, 1-hexenyl, 2-hexenyl, 3-hexenyl, 3-heptenyl, 1-octenyl, 1-nonenyl, 1-decenyl, 1-undecenyl, 1-dodecenyl, and the like.

The term "alkynyl" means a straight or branched triple bonded unsaturated hydrocarbon radical having from 2 to 12 carbon atoms and includes, for example, ethynyl, 2-propynyl, 1-butynyl, 2-butynyl, 3-butynyl, 1-pentynyl, 3opentynyl, 1-hexynyl, 2-hexynyl, 3-hexynyl, 3-heptenyl, 1-octynyl, 2-octynyl, 1-nonynyl, 2-nonynyl, 3-nonynyl, 4-nonynyl, 1-decynyl, 2-decynyl, 2-undecynyl, 3-undecynyl, 3-dodecynyl, and the like.

The term "cycloalkyl" means a saturated hydrocarbon ring which contains from 3 to 12 carbon atoms, for example, cyclopropyl, cyclobutyl, cyclopentyl, cyclohexyl, adamantyl, and the like.

The term "cycloalkylalkyl" means a saturated hydrocarbon ring attached to an alkyl group wherein alkyl is as defined above. The saturated hydrocarbon ring contains from 3 to 12 carbon atoms. Examples of such are cyclopropylmethyl, cyclopentylmethyl, cyclohexylmethyl, adamantylmethyl and the like.

The terms "alkoxy" and "thioalkoxy" are O-alkyl or S-alkyl as defined above for alkyl.

The term "aryl" means an aromatic radical which is a phenyl group, a benzyl group, a naphthyl group, a biphenyl group, a pyrenyl group, an anthracenyl group, 3,3-diphenylalanyl, 10,11-dihydro-5H-dibenzo[a,d]-(cyclohepten-5-yl)glycyl, or a fluorenyl group and the like, unsubstituted or substituted by 1 to 4 substituents selected from alkyl as defined above, alkoxy as defined above, thioalkoxy as defined above, hydroxy, thiol, nitro, halogen, amino,

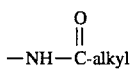

wherein alkyl is as defined above,

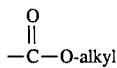

wherein alkyl is as defined above,

wherein alkyl is as defined above, or aryl.

The term "arylalkyl" means an aromatic radical attached to an alkyl radical wherein aryl and alkyl are as defined above for example benzyl, fluorenylmethyl and the like.

The term "heteroaryl" means a heteroaromatic radical which is 2-or 3-thienyl, 2- or 3-furanyl, 2- or 3-pyrrolyl, 2-, 4-, or 5-imidazolyl, 3-, 4-, or 5-pyrazolyl, 2-, 4-, or 5-thiazolyl, 3-, 4-, or 5-isothiazolyl, 2-, 4-, or 5-oxazolyl, 3-, 4-, or 5-isoxazolyl, 3- or 5-1,2,4-triazolyl, 4- or 5-1,2,3-triazolyl, tetrazolyl, 2-, 3-, or 4-pyridinyl, 3-, 4-, or 5-pyridazinyl, 2-pyrazinyl, 2-, 4-, or 5- pyrimidinyl, 2-, 3-, 4-, 5-, 6-, 7-, or 8-quinolinyl, 1-, 3-, 4-, 5-, 6-, 7-, or 8-isoquinolinyl, 2-, 3-, 4-, 5-, 6-, or 7-indolyl, 2-, 3-, 4-, 5-, 6-, or 7-benzo[b]thienyl, or 2-, 4-, 5-, 6-, or 7-benzoxazolyl, 2-, 4-, 5-, 6-, or 7-benzimidazolyl, 2-, 4-, 5-, 6-, or 7-benzothiazolyl, unsubstituted or substituted by 1 to 2 substituents selected from alkyl as defined above, aryl as defined above, alkoxy as defined above, thioalkoxy as defined above, hydroxy, thiol, nitro, halogen, formyl, amino,

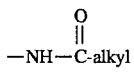

wherein alkyl is as defined above,

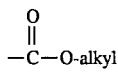

wherein alkyl is as defined above,

wherein alkyl is as defined above or phenyl.

The term "heterocycloalkyl" means 2- or 3-tetrahydrothieno, 2- or 3-tetrahydrofurano, 2- or 3-pyrrolidino, 2-, 4-, or 5-thiazolidino, 2-, 4-, or 5-oxazolidino, 2-, 3-, or 4-piperidino, N-morpholinyl or N-thiamorpholinyl.

"Halogen" is fluorine, chlorine, bromine or iodine.

The following table provides a list of abbreviations and definitions thereof used in the present invention.

| Abbreviation* | Amino Acid |
|---|---|
| Ala | Alanine |
| Arg | Arginine |
| Asn | Asparagine |
| Asp | Aspartic acid |
| Cys | Cysteine |
| Glu | Glutamic acid |
| Gln | Glutamine |
| Gly | Glycine |
| His | Histidine |
| Ile | Isoleucine |
| Leu | Leucine |
| Lys | Lysine |
| Met | Methionine |
| Phe | Phenylalanine |
| Pro | Proline |
| Ser | Serine |
| Thr | Threonine |
| Trp | Tryptophan |
| Tyr | Tyrosine |
| Val | Valine |

| Abbreviation* | Modified and Unusual Amino Acid |
|---|---|
| Bhg | 10,11-Dihydro-5H-dibenzo[a,d]-(cyclohepten-S-yl)glycine or α-Amino-10,11-dihydro-5H-dibenzo-[a,d]cycloheptene-5-acetic acid |
| Bip | (Para-phenyl)phenylalanine |
| Dip | 3,3-Diphenylalanine |
| 3Hyp | 3-Hydroxyproline |
| 4Hyp | 4-Hydroxyproline |
| N-MePhe | N-Methylphenylalanine |
| N-MeAsp | N-Methylaspartic acid |
| N-MeIle | N-Methylisoleucine |
| N-MeVal | N-Methylvaline |
| Nva | Norvaline |

| | |
|---|---|
| Nle | Norleucine |
| Orn | Ornithine |
| Abu | 2-Aminobutyric acid |
| Alg | 2-Amino-4-pentenoic acid (Allylglycine) |
| Arg(NO$_2$) | N$^G$-nitroarginine |
| Atm | 2-Amino-3-(2-amino-5-thiazole)propanoic acid |
| Cpn | 2-Amino-3-cyclopropanepropanoic acid (Cyclopropylalanine) |
| Chx | Cyclohexylalanine (Hexahydrophenylalanine) |
| N-MeChx | N-Methylcyclohexylalanine (N-Methylhexahydrophenylalanine) |
| Emg | 2-Amino-4,5(RS)-epoxy-4-pentenoic acid |
| His(Dnp) | N$^{im}$-2,4-Dinitrophenylhistidine |
| HomoGlu | 2-Aminoadipic acid |
| HomoPhe | 2-Amino-5-phenylpentanoic acid (Homophenylalanine) |
| Met(O) | Methionine sulfoxide |
| Met(O$_2$) | Methionine sulfone |
| 1-Nal | 3-(1'-Naphthyl)alanine |
| 2-Nal | 3-(2'-Naphthyl)alanine |
| Nia | 2-Amino-3-cyanopropanoic acid (Cyanoalanine) |
| Pgl | Phenylglycine |
| Pgy | 2-Aminopentanoic acid (Propylglycine) |
| Pha | 2-Amino-6-(1-pyrrolo)-hexanoic acid |
| Pyr | 2-Amino-3-(3-pyridyl)-propanoic acid (3-Pyridylalanine) |
| Tic | 1,2,3,4-Tetrahydro-3-isoquinolinecarboxylic acid |
| Tza | 2-Amino-3-(4-thiazolyl)-propanoic acid |
| Tyr(Ot-Bu) | O-tertiary butyl-tyrosine |
| Tyr(OMe) | O-Methyl-tyrosine |
| Tyr(OEt) | O-Ethyl-tyrosine |
| Trp(For) | N$^{in}$-Formyl-tryptophan |
| Bheg | 8H-Dibenzo[a,d]cycloheptene glycine |
| Txg | 9H-Thioxanthene glycine |
| Oxn | 9H-Xanthene glycine |

| Abbreviation | Protecting Group |
|---|---|
| Ac | Acetyl |
| Ada | 1-Adamantyl acetic acid |
| Adoc | Adamantyloxycarbonyl |
| Bzl | Benzyl |
| MeBzl | 4-Methylbenzyl |
| Z | Benzyloxycarbonyl |
| 2-Br-Z | ortho-Bromobenzyloxycarbonyl |
| 2-Cl-Z | ortho-Chlorobenzyloxycarbonyl |
| Bom | Benzyloxymethyl |
| Boc | teriary Butyloxycarbonyl |
| TBS | tertiary Butyldimethysilyl |
| Dnp | 2,4-Dinitrophenyl |
| For | Formyl |
| Fmoc | 9-Fluorenylmethyloxycarbonyl |
| NO$_2$ | Nitrol |
| Tos | 4-Toluenesulfonyl (tosyl) |
| Trt | Triphenylmethyl (trityl) |
| Ada | 1-Adamantyl acetic acid |
| Bz | Benzylcarbonyl |
| tBu | t-Butylcarbonyl |
| CF$_3$CO | Trifluoroacetyl |
| Cxl | Cyclohexylacetyl |
| Cxl (U) | Cyclohexylurea |
| Et | Propionyl |
| Pya | 3-Pyridylacetyl |
| Me (U) | Methylurea |

| Abbreviation | Solvents and Reagents |
|---|---|
| HOAc | Acetic acid |
| CH$_3$CN and ACN | Acetonitrile |
| DCM | Dichloromethane |
| DCC | N,N'-Dicyclohexylcarbodiimide |
| DIEA | N,N-Diisopropylethylamine |
| DMF | Dimethylformamide |
| HCl | Hydrochloric acid |
| HF | Hydrofluoric acid |
| HOBt | 1-Hydroxybenzotriazole |
| KOH | Potassium hydroxide |
| TFA | Trifluoroacetic acid |
| MBHA Resin | Methylbenzhydrylamine resin |
| PAM Resin | 4-(Oxymethyl)-phenylacetamidomethyl resin |

*If the optical activity of the amino acid is other than L(S), the amino acid or abbreviation is preceded by the appropriate configuration D(R), or DL(RS).

The compounds of Formula I are capable of further forming both pharmaceutically acceptable acid addition and/or base salts. All of these forms are within the scope of the present invention.

Pharmaceutically acceptable acid addition salts of the compounds of Formula I include salts derived from nontoxic inorganic acids such as hydrochloric, nitric, phosphoric, sulfuric, hydrobromic, hydriodic, hydrofluoric, phosphorous, and the like, as well as the salts derived from nontoxic organic acids, such as aliphatic mono- and dicarboxylic acids, phenyl-substituted alkanoic acids, hydroxy alkanoic acids, alkanedioic acids, aromatic acids, aliphatic and aromatic sulfonic acids, etc. Such salts thus include sulfate, pyrosulfate, bisulfate, sulfite, bisulfite, nitrate, phosphate, monohydrogenphosphate, dihydrogenphosphate, metaphosphate, pyrophosphate, chloride, bromide, iodide, acetate, trifluoroacetate, propionate, caprylate, isobutyrate, oxalate, malonate, succinate, suberate, sebacate, fumarate, maleate, mandelate, benzoate, chlorobenzoate, methylbenzoate, dinitrobenzoate, phthalate, benzenesulfonate, toluenesulfonate, phenylacetate, citrate, lactate, maleate, tartrate, methanesulfonate, and the like. Also contemplated are salts of amino acids such as arginate and the like and gluconate, galacturonate (see, for example, Berge S. M., et al., "Pharmaceutical Salts," *Journal of Pharmaceutical Science*, 66:1–19 (1977)).

The acid addition salts of said basic compounds are prepared by contacting the free base form with a sufficient amount of the desired acid to produce the salt in the conventional manner. Preferably a peptide of Formula I can be converted to an acidic salt by treating with an aqueous solution of the desired acid, such that the resulting pH is less than 4. The solution can be passed through a C18 cartridge to absorb the peptide, washed with copious amounts of water, the peptide eluted with a polar organic solvent such as, for example, methanol, acetonitrile, aqueous mixtures thereof, and the like, and isolated by concentrating under reduced pressure followed by lyophilization. The free base form may be regenerated by contacting the salt form with a base and isolating the free base in the conventional manner. The free base forms differ from their respective salt forms somewhat in certain physical properties such as solubility in polar solvents, but otherwise the salts are equivalent to their respective free base for purposes of the present invention.

Pharmaceutically acceptable base addition salts are formed with metals or amines, such as alkali and alkaline earth metals or organic amines. Examples of metals used as cations are sodium, potassium, magnesium, calcium, and the like. Examples of suitable amines are N,N'-dibenzylethylenediamine, chloroprocaine, choline, diethanolamine, dicyclohexylamine, ethylenediamine, N-methylglucamine, and procaine (see, for example, Berge S. M., et al., "Pharmaceutical Salts," *Journal of Pharmaceutical Science*, 66:1–19 (1977)).

The base addition salts of said acidic compounds are prepared by contacting the free acid form with a sufficient amount of the desired base to produce the salt in the conventional manner. Preferably, a peptide of Formula I can be converted to a base salt by treating with an aqueous solution of the desired base, such that the resulting pH is greater than 9. The solution can be passed through a C18 cartridge to absorb the peptide, washed with copious amounts of water, the peptide eluted with a polar organic solvent such as, for example, methanol, acetonitrile, aqueous mixtures thereof, and the like, and isolated by concentrating under reduced pressure followed by lyophilization. The free acid form may be regenerated by contacting the salt form with an acid and isolating the free acid in the conventional manner. The free acid forms differ from their respective salt forms somewhat in certain physical properties such as solubility in polar solvents, but otherwise the salts are equivalent to their respective free acid for purposes of the present invention.

Certain of the compounds of the present invention can exist in unsolvated forms as well as solvated forms, including hydrated forms. In general, the solvated forms, including hydrated forms, are equivalent to unsolvated forms and are intended to be encompassed within the scope of the present invention.

Certain of the compounds of the present invention possess one or more chiral centers and each center may exist in the R(D) or S(L) configuration. The present invention includes all enantiomeric and epimeric forms as well as the appropriate mixtures thereof.

A preferred compound of Formula I is one wherein $AA^1$ is

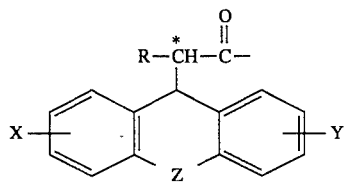

wherein R is

wherein $R^2$ and $R^3$ are each the same or different and each is hydrogen,
alkyl,
alkenyl,
alkynyl,
cycloalkyl,
cycloalkylalkyl,
aryl,
arylalkyl,
heteroaryl, or
fluorenylmethyl,

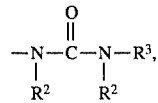

wherein $R^2$ and $R^3$ are as defined above,

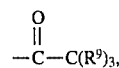

wherein $R^9$ is F, Cl, Br, or I,

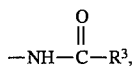

wherein $R^3$ is as defined above, or

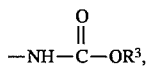

wherein $R^3$ is as defined above excluding $R^3$ is hydrogen;

Z is —O—,
—S(O)$_m$—, wherein m is zero or an integer of 1 or 2,

wherein $R^2$ is as defined above,
—(CH$_2$)$_n$—, wherein n is zero or an integer of 1, 2, 3, or 4,
—(CH$_2$)$_n$—CH=CH—(CH$_2$)$_{n'}$—, wherein n and n' are each independently the same or different and each is as defined above for n,

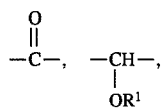

wherein $R^1$ is hydrogen or alkyl,

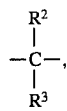

wherein $R^2$ and $R^3$ are each the same or different and each is as defined above, and X and Y are the same and substituted at the same position on the aromatic ring and each substituent is selected from the group consisting of
hydrogen,
halogen, or
alkyl;

$AA^2$ is

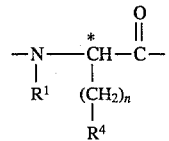

wherein $R^4$ is hydrogen,
alkyl,
alkenyl,
alkynyl,
cycloalkyl,
aryl,
heteroaryl,

wherein $R^{2b}$ and $R^{3b}$ are each the same or different and each is hydrogen,
alkyl,
cycloalkyl,
aryl, or
heteroaryl,
—$OR^{2b}$, wherein $R^{2b}$ is as defined above,

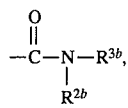

wherein $R^{2b}$ and $R^{3b}$ are each the same or different and each is as defined above for $R^{2b}$ and $R^{3b}$,

wherein $R^{2b}$ is as defined above,

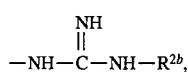

wherein $R^{2b}$ is as defined above, or

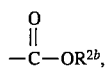

wherein $R^{2b}$ is as defined above, and
$R^1$ and n are as defined above, or $AA^2$ is absent;
$AA^3$ is

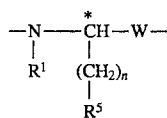

wherein W is

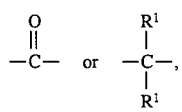

$R^5$ is aryl,
heteroaryl,

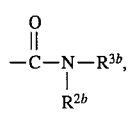

wherein $R^{2b}$ and $R^{3b}$ are each the same or different and each is as defined above,

wherein $R^{2b}$ is as defined above, or

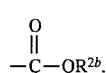

wherein $R^{2b}$ is as defined above, and
$R^1$ and n are as defined above, or $AA^3$ is absent;

$AA^4$ and $AA^5$ are each independently absent or each is independently

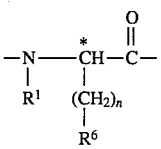

wherein $R^6$ is hydrogen
alkyl,
alkenyl,
alkynyl,
cycloalkyl,
aryl, or
heteroaryl, and
$R^1$ and n are as defined above;
$AA^6$ is

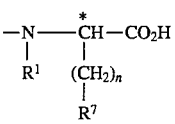

wherein $R^7$ is aryl or heteroaryl, and
$R^1$ and n are as defined above, or

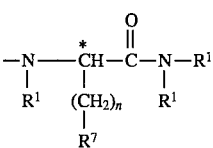

wherein $R^7$, $R^1$, and n are as defined above;
stereochemistry at C*H in $AA^1$, $AA^2$, $AA^3$, $AA^4$, or $AA^5$ is D,L, or DL, and stereochemistry at C*H in $AA^6$ is L; , or a pharmaceutically acceptable salt thereof.

A more preferred compound of Formula I is one wherein $AA^1$ is

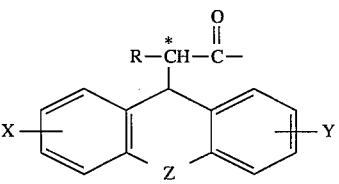

wherein R is

wherein $R^2$ and $R^3$ are each the same or different and each is
hydrogen,
alkyl,
aryl, or
fluorenylmethyl,

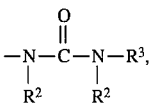

wherein R² and R³ are as defined above,

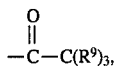

wherein R⁹ is F, Cl, Br, or I,

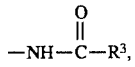

wherein R³ is as defined above, or

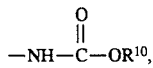

wherein R¹⁰ is hydrogen, alkyl, aryl, arylalkyl, or fluorenylmethyl, excluding R¹⁰ is hydrogen, Z is
—O—,
—S—,
—NH—,
—(CH₂)$_n$—, wherein n is zero or an integer of 1, 2, 3, or 4, or
—(CH₂)$_{n^a}$—CH=CH—(CH₂)$_{n^{a-1}}$—, wherein $n^a$ and $n^{a-1}$ are each independently the same or different and each is zero or an integer of 1 or 2 and X and Y are each the same and substituted at the same position on the aromatic ring and each substituent is selected from the group consisting of
hydrogen,
halogen, or
alkyl;

AA² is

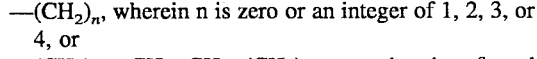

wherein R¹' is hydrogen or methyl,
R⁴ is hydrogen,
alkyl,
aryl,
heteroaryl,

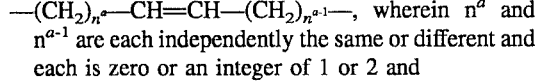

wherein R²ᵇ and R³ᵇ are each the same or different and each is hydrogen or alkyl,

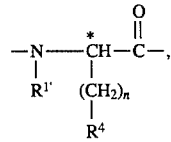

wherein R²ᵇ and R³ᵇ are each the same or different and each is hydrogen or alkyl,

wherein R²ᵇ is as defined above, or

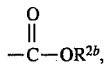

wherein R²ᵇ is as defined above, and
n is zero or an integer of 1, 2, 3, or 4 or AA² is absent;

AA³ is

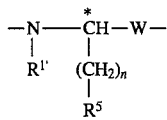

wherein W is

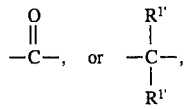

R⁵ is
aryl,
heteroaryl,

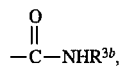

wherein R³ᵇ is hydrogen or alkyl,

wherein R²ᵇ is hydrogen or alkyl, or

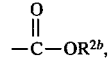

wherein R²ᵇ is hydrogen or alkyl, and
R¹' and n are as defined above;

AA⁴ and AA⁵ are each independently

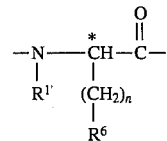

wherein R⁶ is hydrogen,
alkyl,
cycloalkyl, or
aryl, and
R¹' and n are as defined above;

AA⁶ is

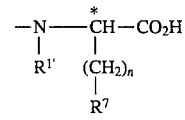

wherein R⁷ is aryl or heteroaryl, and R¹' and n are as defined above, or

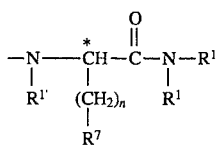

wherein $R^7$, $R^1$, $R^{1'}$, and n are as defined above; stereochemistry at C*H in $AA^1$, $AA^2$, $AA^3$, $AA^4$, or $AA^5$ is D, L, or DL and stereochemistry at C*H in $AA^6$ is L; or a pharmaceutically acceptable salt thereof.

Particularly valuable are:

L-Bhg-Leu-Asp-Ile-Ile-Trp; Seq ID No: 2
D-Bhg-Leu-Asp-Ile-Ile-Trp; Seq ID No: 2
Ac-L-Bhg-Leu-Asp-Ile-Ile-Trp; Seq ID No: 2
Ac-D-Bhg-Leu-Asp-Ile-Ile-Trp; Seq ID No: 2
Ac-D-Bhg-Orn-Asp-Ile-Ile-Trp; Seq ID No: 3
Ac-D-Bhg-Lys-Asp-Ile-Ile-Trp; Seq ID No: 4
Ac-D-Bhg-Asp-Asp-Ile-Ile-Trp; Seq ID No: 5
Ac-D-Bhg-Glu-Asp-Ile-Ile-Trp; Seq ID No: 6
Ac-D-Bhg-Phe-Asp-Ile-Ile-Trp; Seq ID No: 7
Ac-D-Bhg-Arg-Asp-Ile-Ile-Trp; Seq ID No: 8
Ac-D-Bhg-Asp-Ile-Ile-Trp; Seq ID No: 9
Fmoc-D-Bhg-Leu-Asp-Ile-Ile-Trp; Seq ID No: 2
Fmoc-D-Bhg-Orn-Asp-Ile-Ile-Trp; Seq ID No: 3
Fmoc-D-Bhg-Lys-Asp-Ile-Ile-Trp; Seq ID No: 4
Fmoc-D-Bhg-Asp-Asp-Ile-Ile-Trp; Seq ID No: 5
Fmoc-D-Bhg-Glu-Asp-Ile-Ile-Trp; Seq ID No: 6
Fmoc-D-Bhg-Phe-Asp-Ile-Ile-Trp; Seq ID No: 7
Fmoc-D-Bhg-Arg-Asp-Ile-Ile-Trp; Seq ID No: 8
Fmoc-D-Bhg-Asp-Ile-Ile-Trp; Seq ID No: 9
Ac-D-Bhg-Leu-Phe-Ile-Ile-Trp; Seq ID No: 10
Ac-D-Bhg-Leu-Asn-Ile-Ile-Trp; Seq ID No: 11
Ac-D-Bhg-Leu-Glu-Ile-Ile-Trp; Seq ID No: 12
Ac-D-Bhg-Leu-Gln-Ile-Ile-Trp; Seq ID No: 13
Ac-D-Bhg-Leu-Tyr-Ile-Ile-Trp; Seq ID No: 14
Ac-D-Bhg-Leu-1-Nal-Ile-Ile-Trp; Seq ID No: 15
Ac-D-Bhg-Leu-2-Nal-Ile-Ile-Trp; Seq ID No: 15
Ac-D-Bhg-Leu-Trp-Ile-Ile-Trp; Seq ID No: 16
Ac-D-Bhg-Leu-Asp-Val-Ile-Trp; Seq ID No: 17
Ac-D-Bhg-Leu-Asp-Ile-Val-Trp; Seq ID No: 18
Ac-D-Bhg-Leu-Asp-Chx-Ile-Trp; Seq ID No: 19
Ac-D-Bhg-Leu-Asp-Ile-Chx-Trp; Seq ID No: 20
Ac-D-Bhg-Arg-Asp-Ile-Chx-Trp; Seq ID No: 21
Ac-D-Bhg-Lys-Asp-Ile-Chx-Trp; Seq ID No: 22
Ac-D-Bhg-Orn-Asp-Ile-Chx-Trp; Seq ID No: 23
Ac-D-Bhg-Asp-Asp-Ile-Chx-Trp; Seq ID No: 24
Ac-D-Bhg-Glu-Asp-Ile-Chx-Trp; Seq ID No: 25
Fmoc-D-Bhg-Leu-Phe-Ile-Ile-Trp; Seq ID No: 10
Fmoc-D-Bhg-Leu-Asn-Ile-Ile-Trp; Seq ID No: 11
Fmoc-D-Bhg-Leu-Glu-Ile-Ile-Trp; Seq ID No: 12
Fmoc-D-Bhg-Leu-Gln-Ile-Ile-Trp; Seq ID No: 13
Fmoc-D-Bhg-Leu-Tyr-Ile-Ile-Trp; Seq ID No: 14
Fmoc-D-Bhg-Leu-Asp-Val-Ile-Trp; Seq ID No: 17
Fmoc-D-Bhg-Leu-Asp-Ile-Val-Trp; Seq ID No: 18
Fmoc-D-Bhg-Leu-Asp-Chx-Ile-Trp; Seq ID No: 19
Fmoc-D-Bhg-Arg -Asp-Chx-Ile-Trp; Seq ID No: 26
Fmoc-D-Bhg-Lys-Asp-Chx-Ile-Trp; Seq ID No: 27
Fmoc-D-Bhg-Orn-Asp-Chx-Ile-Trp; Seq ID No: 28
Fmoc-D-Bhg-Asp-Asp-Chx-Ile-Trp; Seq ID No: 29
Fmoc-D-Bhg-Glu-Asp-Chx-Ile-Trp; Seq ID No: 30
Fmoc-D-Bhg-Leu-Asp-Ile-Chx-Trp; Seq ID No: 20
Fmoc-D-Bhg-Arg-Asp-Ile-Chx-Trp; Seq ID No: 21
Fmoc-D-Bhg-Lys-Asp-Ile-Chx-Trp; Seq ID No: 22
Fmoc-D-Bhg-Orn-Asp-Ile-Chx-Trp; Seq ID No: 23
Fmoc-D-Bhg-Asp-Asp-Ile-Chx-Trp; Seq ID No: 24
Fmoc-D-Bhg-Glu-Asp-Ile-Chx-Trp; Seq ID No: 25
Ac-D-Bheg-Leu-Asp-Ile-Ile-Trp; Seq ID No: 2
Ac-D-Bheg-Orn-Asp-Ile-Ile-Trp; Seq ID No: 3
Ac-D-Bheg-Lys-Asp-Ile-Ile-Trp; Seq ID No: 4
Ac-D-Bheg-Asp-Asp-Ile-Ile-Trp; Seq ID No: 5
Ac-D-Bheg-Glu-Asp-Ile-Ile-Trp; Seq ID No: 6
Ac-D-Bheg-Phe-Asp-Ile-Ile-Trp; Seq ID No: 7
Ac-D-Bheg-Arg-Asp-Ile-Ile-Trp; Seq ID No: 8
Ac-D-Bheg-Asp-Ile-Ile-Trp; Seq ID No: 9
Fmoc-D-Bheg-Leu-Asp-Ile-Ile-Trp; Seq ID No: 2
Fmoc-D-Bheg-Orn-Asp-Ile-Ile-Trp; Seq ID No: 3
Fmoc-D-Bheg-Lys-Asp-Ile-Ile-Trp; Seq ID No: 4
Fmoc-D-Bheg-Asp-Asp-Ile-Ile-Trp; Seq ID No: 5
Fmoc-D-Bheg-Glu-Asp-Ile-Ile-Trp; Seq ID No: 6
Fmoc-D-Bheg-Phe-Asp-Ile-Ile-Trp; Seq ID No: 7
Fmoc-D-Bheg-Arg-Asp-Ile-Ile-Trp; Seq ID No: 8
Fmoc-D-Bheg-Asp-Ile-Ile-Trp; Seq ID No: 9
Ac-D-Bheg-Leu-Phe-Ile-Ile-Trp; Seq ID No: 10
Ac-D-Bheg-Leu-Asn-Ile-Ile-Trp; Seq ID No: 11
Ac-D-Bheg-Leu-Glu-Ile-Ile-Trp; Seq ID No: 12
Ac-D-Bheg-Leu-Gln-Ile-Ile-Trp; Seq ID No: 13
Ac-D-Bheg-Leu-Tyr-Ile-Ile-Trp; Seq ID No: 14
Ac-D-Bheg-Leu-1-Nal-Ile-Ile-Trp; Seq ID No: 15
Ac-D-Bheg-Leu-2-Nal-Ile-Ile-Trp; Seq ID No: 15
Ac-D-Bheg-Leu-Trp-Ile-Ile-Trp; Seq ID No: 16
Ac-D-Bheg-Leu-Asp-Val-Ile-Trp; Seq ID No: 17
Ac-D-Bheg-Leu-Asp-Ile-Val-Trp; Seq ID No: 18
Ac-D-Bheg-Leu-Asp-Chx-Ile-Trp; Seq ID No: 19
Ac-D-Bheg-Leu-Asp-Ile-Chx-Trp; Seq ID No: 20
Ac-D-Bheg-Arg-Asp-Ile-Chx-Trp; Seq ID No: 21
Ac-D-Bheg-Lys-Asp-Ile-Chx-Trp; Seq ID No: 22
Ac-D-Bheg-Orn-Asp-Ile-Chx-Trp; Seq ID No: 23
Ac-D-Bheg-Asp-Asp-Ile-Chx-Trp; Seq ID No: 24
Ac-D-Bheg-Glu-Asp-Ile-Chx-Trp; Seq ID No: 25
Fmoc-D-Bheg-Leu-Phe-Ile-Ile-Trp; Seq ID No: 10
Fmoc-D-Bheg-Leu-Asn-Ile-Ile-Trp; Seq ID No: 11
Fmoc-D-Bheg-Leu-Glu-Ile-Ile-Trp; Seq ID No: 12
Fmoc-D-Bheg-Leu-Gln-Ile-Ile-Trp; Seq ID No: 13
Fmoc-D-Bheg-Leu-Tyr-Ile-Ile-Trp; Seq ID No: 14
Fmoc-D-Bheg-Leu-Asp-Val-Ile-Trp; Seq ID No: 17
Fmoc-D-Bheg-Leu-Asp-Ile-Val-Trp; Seq ID No: 18
Fmoc-D-Bheg-Leu-Asp-Chx-Ile-Trp; Seq ID No: 19
Fmoc-D-Bheg-Arg-Asp-Chx-Ile-Trp; Seq ID No: 26
Fmoc-D-Bheg-Lys-Asp-Chx-Ile-Trp; Seq ID No: 27
Fmoc-D-Bheg-Orn-Asp-Chx-Ile-Trp; Seq ID No: 28
Fmoc-D-Bheg-Asp-Asp-Chx-Ile-Trp; Seq ID No: 29
Fmoc-D-Bheg-Glu-Asp-Chx-Ile-Trp; Seq ID No: 30
Fmoc-D-Bheg-Leu-Asp-Ile-Chx-Trp; Seq ID No: 20
Fmoc-D-Bheg-Arg-Asp-Ile-Chx-Trp; Seq ID No: 21
Fmoc-D-Bheg-Lys-Asp-Ile-Chx-Trp; Seq ID No: 22
Fmoc-D-Bheg-Orn-Asp-Ile-Chx-Trp; Seq ID No: 23
Fmoc-D-Bheg-Asp-Asp-Ile-Chx-Trp; Seq ID No: 24
Fmoc-D-Bheg-Glu-Asp-Ile-Chx-Trp; Seq ID No: 25
Ac-D-Txg-Leu-Asp-Ile-Ile-Trp; Seq ID No: 2
Ac-D-Txg-Orn-Asp-Ile-Ile-Trp; Seq ID No: 3
Ac-D-Txg-Lys-Asp-Ile-Ile-Trp; Seq ID No: 4
Ac-D-Txg-Asp-Asp-Ile-Ile-Trp; Seq ID No: 5
Ac-D-Txg-Glu-Asp-Ile-Ile-Trp; Seq ID No: 6
Ac-D-Txg-Phe-Asp-Ile-Ile-Trp; Seq ID No: 7
Ac-D-Txg-Arg-Asp-Ile-Ile-Trp; Seq ID No: 8
Ac-D-Txg-Asp-Ile-Ile-Trp; Seq ID No: 9
Fmoc-D-Txg-Leu-Asp-Ile-Ile-Trp; Seq ID No: 2
Fmoc-D-Txg-Orn-Asp-Ile-Ile-Trp; Seq ID No: 3
Fmoc-D-Txg-Lys-Asp-Ile-Ile-Trp; Seq ID No: 4
Fmoc-D-Txg-Asp-Asp-Ile-Ile-Trp; Seq ID No: 5
Fmoc-D-Txg-Glu-Asp-Ile-Ile-Trp; Seq ID No: 6
Fmoc-D-Txg-Phe-Asp-Ile-Ile-Trp; Seq ID No: 7
Fmoc-D-Txg-Arg-Asp-Ile-Ile-Trp; Seq ID No: 8

Fmoc-D-Txg-Asp-Ile-Ile-Trp; Seq ID No: 9
Ac-D-Txg-Leu-Phe-Ile-Ile-Trp; Seq ID No: 10
Ac-D-Txg-Leu-Asn-Ile-Ile-Trp; Seq ID No: 11
Ac-D-Txg-Leu-Glu-Ile-Ile-Trp; Seq ID No: 12
Ac-D-Txg-Leu-Gln-Ile-Ile-Trp; Seq ID No: 13
Ac-D-Txg-Leu-Tyr-Ile-Ile-Trp; Seq ID No: 14
Ac-D-Txg-Leu-1-Nal-Ile-Ile-Trp; Seq ID No: 15
Ac-D-Txg-Leu-2-Nal-Ile-Ile-Trp; Seq ID No: 15
Ac-D-Txg-Leu-Trp-Ile-Ile-Trp; Seq ID No: 16
Ac-D-Txg-Leu-Asp-Val-Ile-Trp; Seq ID No: 17
Ac-D-Txg-Leu-Asp-Ile-Val-Trp; Seq ID No: 18
Ac-D-Txg-Leu-Asp-Chx-Ile-Trp; Seq ID No: 19
Ac-D-Txg-Leu-Asp-Ile-Chx-Trp; Seq ID No: 20
Ac-D-Txg-Arg-Asp-Ile-Chx-Trp; Seq ID No: 21
Ac-D-Txg-Lys-Asp-Ile-Chx-Trp; Seq ID No: 22
Ac-D-Txg-Orn-Asp-Ile-Chx-Trp; Seq ID No: 23
Ac-D-Txg-Asp-Asp-Ile-Chx-Trp; Seq ID No: 24
Ac-D-Txg-Glu-Asp-Ile-Chx-Trp; Seq ID No: 25
Fmoc-D-Txg-Leu-Phe-Ile-Ile-Trp; Seq ID No: 10
Fmoc-D-Txg-Leu-Asn-Ile-Ile-Trp; Seq ID No: 11
Fmoc-D-Txg-Leu-Glu-Ile-Ile-Trp; Seq ID No: 12
Fmoc-D-Txg-Leu-Gln-Ile-Ile-Trp; Seq ID No: 13
Fmoc-D-Txg-Leu-Tyr-Ile-Ile-Trp; Seq ID No: 14
Fmoc-D-Txg-Leu-Asp-Val-Ile-Trp; Seq ID No: 17
Fmoc-D-Txg-Leu-Asp-Ile-Val-Trp; Seq ID No: 18
Fmoc-D-Txg-Leu-Asp-Chx-Ile-Trp; Seq ID No: 19
Fmoc-D-Txg-Arg-Asp-Chx-Ile-Trp; Seq ID No: 26
Fmoc-D-Txg-Lys-Asp-Chx-Ile-Trp; Seq ID No: 27
Fmoc-D-Txg-Orn-Asp-Chx-Ile-Trp; Seq ID No: 28
Fmoc-D-Txg-Asp-Asp-Chx-Ile-Trp; Seq ID No: 29
Fmoc-D-Txg-Glu-Asp-Chx-Ile-Trp; Seq ID No: 30
Fmoc-D-Txg-Leu-Asp-Ile-Chx-Trp; Seq ID No: 20
Fmoc-D-Txg-Arg-Asp-Ile-Chx-Trp; Seq ID No: 21
Fmoc-D-Txg-Lys-Asp-Ile-Chx-Trp; Seq ID No: 22
Fmoc-D-Txg-Orn-Asp-Ile-Chx-Trp; Seq ID No: 23
Fmoc-D-Txg-Asp-Asp-Ile-Chx-Trp; Seq ID No: 24
Fmoc-D-Txg-Glu-Asp-Ile-Chx-Trp; Seq ID No: 25
Et-D-Bhg-Leu-Asp-Ile-Ile-Trp; Seq ID No: 2
Bz-D-Bhg-Leu-Asp-Ile-Ile-Trp; Seq ID No: 2
Pya-D-Bhg-Leu-Asp-Ile-Ile-Trp; Seq ID No: 2
Cxl-D-Bhg-Leu-Asp-Ile-Ile-Trp; Seq ID No: 2
Ada-D-Bhg-Leu-Asp-Ile-Ile-Trp; Seq ID No: 2
Cxl(U)-D-Bhg-Leu-Asp-Ile-Ile-Trp; Seq ID No: 2
Me(U)-D-Bhg-Leu-Asp-Ile-Ile-Trp; Seq ID No: 2
tBu-D-Bhg-Leu-Asp-Ile-Ile-Trp; Seq ID No: 2
CF$_3$CO-D-Bhg-Leu-Asp-Ile-Ile-Trp; Seq ID No: 2
Et-D-Bheg-Leu-Asp-Ile-Ile-Trp; Seq ID No: 2
Bz-D-Bheg-Leu-Asp-Ile-Ile-Trp; Seq ID No: 2
Pya-D-Bheg-Leu-Asp-Ile-Ile-Trp; Seq ID No: 2
Cxl-D-Bheg-Leu-Asp-Ile-Ile-Trp; Seq ID No: 2
Ada-D-Bheg-Leu-Asp-Ile-Ile-Trp; Seq ID No: 2
Cxl(U)-D-Bheg-Leu-Asp-Ile-Ile-Trp; Seq ID No: 2
Me(U)-D-Bheg-Leu-Asp-Ile-Ile-Trp; Seq ID No: 2
tBu-D-Bheg-Leu-Asp-Ile-Ile-Trp; Seq ID No: 2
CF$_3$CO-D-Bheg-Leu-Asp-Ile-Ile-Trp; Seq ID No: 2
Ac-D-Bhg-Leu-Asp-Phe-Ile-Trp; Seq ID No: 31
Ac-D-Bhg-Orn-Asp-Phe-Ile-Trp; Seq ID No: 32
Ac-D-Bhg-Lys-Asp-Phe-Ile-Trp; Seq ID No: 33
Ac-D-Bhg-Asp-Asp-Phe-Ile-Trp; Seq ID No: 34
Ac-D-Bhg-Glu-Asp-Phe-Ile-Trp; Seq ID No: 35
Ac-D-Bhg-Phe-Asp-Phe-Ile-Trp; Seq ID No: 36
Ac-D-Bhg-Arg-Asp-Phe-Ile-Trp; Seq ID No: 37
Ac-D-Bheg-Leu-Asp-Phe-Ile-Trp; Seq ID No: 31
Ac-D-Bheg-Orn-Asp-Phe-Ile-Trp; Seq ID No: 32
Ac-D-Bheg-Lys-Asp-Phe-Ile-Trp; Seq ID No: 33
Ac-D-Bheg-Asp-Asp-Phe-Ile-Trp; Seq ID No: 34
Ac-D-Bheg-Glu-Asp-Phe-Ile-Trp; Seq ID No: 35
Ac-D-Bheg-Phe-Asp-Phe-Ile-Trp; Seq ID No: 36
Ac-D-Bheg-Arg-Asp-Phe-Ile-Trp; Seq ID No: 37
L-Bhg-Leu-Asp-Ile-N-MeIle-Trp; Seq ID No: 20
D-Bhg-Leu-Asp-Ile-N-MeIle-Trp; Seq ID No: 20
Ac-L-Bhg-Leu-Asp-Ile-N-MeIle-Trp; Seq ID No: 20
Ac-D-Bhg-Leu-Asp-Ile-N-MeIle-Trp; Seq ID No: 20
Ac-D-Bhg-Orn-Asp-Ile-N-MeIle-Trp; Seq ID No: 38
Ac-D-Bhg-Lys-Asp-Ile-N-MeIle-Trp; Seq ID No: 22
Ac-D-Bhg-Asp-Asp-Ile-N-MeIle-Trp; Seq ID No: 24
Ac-D-Bhg-Glu-Asp-Ile-N-MeIle-Trp; Seq ID No: 25
Ac-D-Bhg-Phe-Asp-Ile-N-MeIle-Trp; Seq ID No: 39
Ac-D-Bhg-Arg-Asp-Ile-N-MeIle-Trp; Seq ID No: 21
Ac-D-Bhg-Asp-Ile-N-MeIle-Trp; Seq ID No: 40
Fmoc-D-Bhg-Leu-Asp-Ile-N-MeIle-Trp; Seq ID No: 20
Fmoc-D-Bhg-Orn-Asp-Ile-N-MeIle-Trp; Seq ID No: 38
Fmoc-D-Bhg-Lys-Asp-Ile-N-MeIle-Trp; Seq ID No: 22
Fmoc-D-Bhg-Asp-Asp-Ile-N-MeIle-Trp; Seq ID No: 24
Fmoc-D-Bhg-Glu-Asp-Ile-N-MeIle-Trp; Seq ID No: 25
Fmoc-D-Bhg-Phe-Asp-Ile-N-MeIle-Trp; Seq ID No: 39
Fmoc-D-Bhg-Arg-Asp-Ile-N-MeIle-Trp; Seq ID No: 21
Fmoc-D-Bhg-Asp-Ile-N-MeIle-Trp; Seq ID No: 40
Ac-D-Bhg-Leu-Phe-Ile-N-MeIle-Trp; Seq ID No: 41
Ac-D-Bhg-Leu-Asn-Ile-N-MeIle-Trp; Seq ID No: 20
Ac-D-Bhg-Leu-Glu-Ile-N-MeIle-Trp; Seq ID No: 42
Ac-D-Bhg-Leu-Gln-Ile-N-MeIle-Trp; Seq ID No: 43
Ac-D-Bhg-Leu-Tyr-Ile-N-MeIle-Trp; Seq ID No: 44
Ac-D-Bhg-Leu-1-Nal-Ile-N-MeIle-Trp; Seq ID No: 45
Ac-D-Bhg-Leu-2-Nal-Ile-N-MeIle-Trp; Seq ID No: 45
Ac-D-Bhg-Leu-Trp-Ile-N-MeIle-Trp; Seq ID No: 46
Ac-D-Bhg-Leu-Asp-Val-N-MeIle-Trp; Seq ID No: 47
Ac-D-Bhg-Leu-Asp-Ile-N-MeVal-Trp; Seq ID No: 20
Ac-D-Bhg-Leu-Asp-Chx-N-MeIle-Trp; Seq ID No: 48
Ac-D-Bhg-Leu-Asp-Ile-N-MeChx-Trp; Seq ID No: 20
Ac-D-Bhg-Arg-Asp-Ile-N-MeChx-Trp; Seq ID No: 21
Ac-D-Bhg-Lys-Asp-Ile-N-MeChx-Trp; Seq ID No: 22
Ac-D-Bhg-Orn-Asp-Ile-N-MeChx-Trp; Seq ID No: 38
Ac-D-Bhg-Asp-Asp-Ile-N-MeChx-Trp; Seq ID No: 24
Ac-D-Bhg-Glu-Asp-Ile-N-MeChx-Trp; Seq ID No: 25
Fmoc-D-Bhg-Leu-Phe-Ile-N-MeIle-Trp; Seq ID No: 41
Fmoc-D-Bhg-Leu-Asn-Ile-N-MeIle-Trp; Seq ID No: 20
Fmoc-D-Bhg-Leu-Glu-Ile-N-MeIle-Trp; Seq ID No: 42
Fmoc-D-Bhg-Leu-Gln-Ile-N-MeIle-Trp; Seq ID No: 43
Fmoc-D-Bhg-Leu-Tyr-Ile-N-MeIle-Trp; Seq ID No: 44
Fmoc-D-Bhg-Leu-Asp-Val-N-MeIle-Trp; Seq ID No: 47
Fmoc-D-Bhg-Leu-Asp-Ile-N-MeVal-Trp; Seq ID No: 20
Fmoc-D-Bhg-Leu-Asp-Chx-N-MeIle-Trp; Seq ID No: 49
Fmoc-D-Bhg-Arg-Asp-Chx-N-MeIle-Trp; Seq ID No: 50
Fmoc-D-Bhg-Lys-Asp-Chx-N-MeIle-Trp; Seq ID No: 51
Fmoc-D-Bhg-Orn-Asp-Chx-N-MeIle-Trp; Seq ID No: 52
Fmoc-D-Bhg-Asp-Asp-Chx-N-MeIle-Trp; Seq ID No: 53
Fmoc-D-Bhg-Glu-Asp-Chx-N-MeIle-Trp; Seq ID No: 54
Fmoc-D-Bhg-Leu-Asp-Ile-N-MeChx-Trp; Seq ID No: 20
Fmoc-D-Bhg-Arg-Asp-Ile-N-MeChx-Trp; Seq ID No: 21
Fmoc-D-Bhg-Lys-Asp-Ile-N-MeChx-Trp; Seq ID No: 22
Fmoc-D-Bhg-Orn-Asp-Ile-N-MeChx-Trp; Seq ID No: 38
Fmoc-D-Bhg-Asp-Asp-Ile-N-MeChx-Trp; Seq ID No: 24
Fmoc-D-Bhg-Glu-Asp-Ile-N-MeChx-Trp; Seq ID No: 25
Ac-D-Bheg-Leu-Asp-Ile-N-MeIle-Trp; Seq ID No: 20
Ac-D-Bheg-Orn-Asp-Ile-N-MeIle-Trp; Seq ID No: 38
Ac-D-Bheg-Lys-Asp-Ile-N-MeIle-Trp; Seq ID No: 22
Ac-D-Bheg-Asp-Asp-Ile-N-MeIle-Trp; Seq ID No: 24
Ac-D-Bheg-Glu-Asp-Ile-N-MeIle-Trp; Seq ID No: 25
Ac-D-Bheg-Phe-Asp-Ile-N-MeIle-Trp; Seq ID No: 39
Ac-D-Bheg-Arg-Asp-Ile-N-MeIle-Trp; Seq ID No: 21
Fmoc-D-Bheg-Leu-D-Asp-Ile-N-MeIle-Trp; Seq ID No: 40
Fmoc-D-Bheg-Leu-Asp-Ile-N-MeIle-Trp; Seq ID No: 20
Fmoc-D-Bheg-Orn-Asp-Ile-N-MeIle-Trp; Seq ID No: 38

Fmoc-D-Bheg-Lys-Asp-Ile-N-MeIle-Trp; Seq ID No: 22
Fmoc-D-Bheg-Asp-Asp-Ile-N-MeIle-Trp; Seq ID No: 24
Fmoc-D-Bheg-Glu-Asp-Ile-N-MeIle-Trp; Seq ID No: 25
Fmoc-D-Bheg-Phe-Asp-Ile-N-MeIle-Trp; Seq ID No: 39
Fmoc-D-Bheg-Arg-Asp-Ile-N-MeIle-Trp; Seq ID No: 21
Fmoc-D-Bheg-Asp-Ile-N-MeIle-Trp; Seq ID No: 40
Ac-D-Bheg-Leu-Phe-Ile-N-MeIle-Trp; Seq ID No: 41
Ac-D-Bheg-Leu-Asn-Ile-N-MeIle-Trp; Seq ID No: 55
Ac-D-Bheg-Leu-Glu-Ile-N-MeIle-Trp; Seq ID No: 42
Ac-D-Bheg-Leu-Gln-Ile-N-MeIle-Trp; Seq ID No: 43
Ac-D-Bheg-Leu-Tyr-Ile-N-MeIle-Trp; Seq ID No: 44
Ac-D-Bheg-Leu-1-Nal-Ile-N-MeIle-Trp; Seq ID No: 45
Ac-D-Bheg-Leu-2-Nal-Ile-N-MeIle-Trp; Seq ID No: 45
Ac-D-Bheg-Leu-Trp-Ile-N-MeIle-Trp; Seq ID No: 46
Ac-D-Bheg-Leu-Asp-Val-N-MeIle-Trp; Seq ID No: 47
Ac-D-Bheg-Leu-Asp-Ile-N-MeVal-Trp; Seq ID No: 20
Ac-D-Bheg-Leu-Asp-Chx-N-MeIle-Trp; Seq ID No: 49
Ac-D-Bheg-Leu-Asp-Ile-N-MeChx-Trp; Seq ID No: 20
Ac-D-Bheg-Arg-Asp-Ile-N-MeChx-Trp; Seq ID No: 21
Ac-D-Bheg-Lys-Asp-Ile-N-MeChx-Trp; Seq ID No: 22
Ac-D-Bheg-Orn-Asp-Ile-N-MeChx-Trp; Seq ID No: 38
Ac-D-Bheg-Asp-Asp-Ile-N-MeChx-Trp; Seq ID No: 24
Ac-D-Bheg-Glu-Asp-Ile-N-MeChx-Trp; Seq ID No: 25
Fmoc-D-Bheg-Leu-Phe-Ile-N-MeIle-Trp; Seq ID No: 41
Fmoc-D-Bheg-Leu-Asn-Ile-N-MeIle-Trp; Seq ID No: 55
Fmoc-D-Bheg-Leu-Glu-Ile-N-MeIle-Trp; Seq ID No: 42
Fmoc-D-Bheg-Leu-Gln-Ile-N-MeIle-Trp; Seq ID No: 43
Fmoc-D-Bheg-Leu-Tyr-Ile-N-MeIle-Trp; Seq ID No: 44
Fmoc-D-Bheg-Leu-Asp-Val-N-MeIle-Trp; Seq ID No: 47
Fmoc-D-Bheg-Leu-Asp-Ile-N-MeVal-Trp; Seq ID No: 20
Fmoc-D-Bheg-Leu-Asp-Chx-N-MeIle-Trp; Seq ID No: 49
Fmoc-D-Bheg-Arg -Asp-Chx-N-MeIle-Trp; Seq ID No: 50
Fmoc-D-Bheg-Lys-Asp-Chx-N-MeIle-Trp; Seq ID No: 51
Fmoc-D-Bheg-Orn-Asp-Chx-N-MeIle-Trp; Seq ID No: 52
Fmoc-D-Bheg-Asp-Asp-Chx-N-MeIle-Trp; Seq ID No: 53
Fmoc-D-Bheg-Glu-Asp-Chx-N-MeIle-Trp; Seq ID No: 54
Fmoc-D-Bheg-Leu-Asp-Ile-N-MeChx-Trp; Seq ID No: 20
Fmoc-D-Bheg-Arg-Asp-Ile-N-MeChx-Trp; Seq ID No: 21
Fmoc-D-Bheg-Lys-Asp-Ile-N-MeChx-Trp; Seq ID No: 22
Fmoc-D-Bheg-Orn-Asp-Ile-N-MeChx-Trp; Seq ID No: 38
Fmoc-D-Bheg-Asp-Asp-Ile-N-MeChx-Trp; Seq ID No: 24
Fmoc-D-Bheg-Glu-Asp-Ile-N-MeChx-Trp; Seq ID No: 25
Fmoc-D-Bheg-Leu-D-Asp-Ile-Ile-Trp; Seq ID No: 2
Fmoc-D-Bheg-Leu-D-Asp-Ile-N-MeIle-Trp; Seq ID No: 20
Fmoc-D-Bhg-Leu-D-Asp-Ile-Ile-Trp; Seq ID No: 2
Fmoc-D-Bhg-Leu-D-Asp-Ile-N-MeIle-Trp; Seq ID No: 20
Ac-D-Txg-Leu-Asp-Ile-N-MeIle-Trp; Seq ID No: 20
Ac-D-Txg-Orn-Asp-Ile-N-MeIle-Trp; Seq ID No: 38
Ac-D-Txg-Lys-Asp-Ile-N-MeIle-Trp; Seq ID No: 22
Ac-D-Txg-Asp-Asp-Ile-N-MeIle-Trp; Seq ID No: 24
Ac-D-Txg-Glu-Asp-Ile-N-MeIle-Trp; Seq ID No: 25
Ac-D-Txg-Phe-Asp-Ile-N-MeIle-Trp; Seq ID No: 39
Ac-D-Txg-Arg-Asp-Ile-N-MeIle-Trp; Seq ID No: 21
Ac-D-Txg-Asp-Ile-N-MeIle-Trp; Seq ID No: 40
Fmoc-D-Txg-Leu-Asp-Ile-N-MeIle-Trp; Seq ID No: 20
Fmoc-D-Txg-Orn-Asp-Ile-N-MeIle-Trp; Seq ID No: 38
Fmoc-D-Txg-Lys-Asp-Ile-N-MeIle-Trp; Seq ID No: 22
Fmoc-D-Txg-Asp-Asp-Ile-N-MeIle-Trp; Seq ID No: 24
Fmoc-D-Txg-Glu-Asp-Ile-N-MeIle-Trp; Seq ID No: 25
Fmoc-D-Txg-Phe-Asp-Ile-N-MeIle-Trp; Seq ID No: 39
Fmoc-D-Txg-Arg-Asp-Ile-N-MeIle-Trp; Seq ID No: 21
Fmoc-D-Txg-Asp-Ile-N-MeIle-Trp; Seq ID No: 56
Ac-D-Txg-Leu-Phe-Ile-N-MeIle-Trp; Seq ID No: 41
Ac-D-Txg-Leu-Asn-Ile-N-MeIle-Trp; Seq ID No: 55
Ac-D-Txg-Leu-Glu-Ile-N-MeIle-Trp; Seq ID No: 42
Ac-D-Txg-Leu-Gln-Ile-N-MeIle-Trp; Seq ID No: 43
Ac-D-Txg-Leu-Tyr-Ile-N-MeIle-Trp; Seq ID No: 44
Ac-D-Txg-Leu-1-Nal-Ile-N-MeIle-Trp; Seq ID No: 45
Ac-D-Txg-Leu-2-Nal-Ile-N-MeIle-Trp; Seq ID No: 45
Ac-D-Txg-Leu-Trp-Ile-N-MeIle-Trp; Seq ID No: 46
Ac-D-Txg-Leu-Asp-Val-N-MeIle-Trp; Seq ID No: 47
Ac-D-Txg-Leu-Asp-Ile-N-MeVal-Trp; Seq ID No: 20
Ac-D-Txg-Leu-Asp-Chx-N-MeIle-Trp; Seq ID No: 49
Ac-D-Txg-Leu-Asp-Ile-N-MeChx-Trp; Seq ID No: 20
Ac-D-Txg-Arg-Asp-Ile-N-MeChx-Trp; Seq ID No: 21
Ac-D-Txg-Lys-Asp-Ile-N-MeChx-Trp; Seq ID No: 22
Ac-D-Txg-Orn-Asp-Ile-N-MeChx-Trp; Seq ID No: 38
Ac-D-Txg-Asp-Asp-Ile-N-MeChx-Trp; Seq ID No: 24
Ac-D-Txg-Glu-Asp-Ile-N-MeChx-Trp; Seq ID No: 25
Fmoc-D-Txg-Leu-Phe-Ile-N-MeIle-Trp; Seq ID No: 41
Fmoc-D-Txg-Leu-Asn-Ile-N-MeIle-Trp; Seq ID No: 55
Fmoc-D-Txg-Leu-Glu-Ile-N-MeIle-Trp; Seq ID No: 42
Fmoc-D-Txg-Leu-Gln-Ile-N-MeIle-Trp; Seq ID No: 43
Fmoc-D-Txg-Leu-Tyr-Ile-N-MeIle-Trp; Seq ID No: 44
Fmoc-D-Txg-Leu-Asp-Val-N-MeIle-Trp; Seq ID No: 47
Fmoc-D-Txg-Leu-Asp-Ile-N-MeVal-Trp; Seq ID No: 20
Fmoc-D-Txg-Leu-Asp-Chx-N-MeIle-Trp; Seq ID No: 49
Fmoc-D-Txg-Arg-Asp-Chx-N-MeIle-Trp; Seq ID No: 50
Fmoc-D-Txg-Lys-Asp-Chx-N-MeIle-Trp; Seq ID No: 51
Fmoc-D-Txg-Orn-Asp-Chx-N-MeIle-Trp; Seq ID No: 52
Fmoc-D-Txg-Asp-Asp-Chx-N-MeIle-Trp; Seq ID No: 53
Fmoc-D-Txg-Glu-Asp-Chx-N-MeIle-Trp; Seq ID No: 54
Fmoc-D-Txg-Leu-Asp-Ile-N-MeChx-Trp; Seq ID No: 20
Fmoc-D-Txg-Arg-Asp-Ile-N-MeChx-Trp; Seq ID No: 21
Fmoc-D-Txg-Lys-Asp-Ile-N-MeChx-Trp; Seq ID No: 22
Fmoc-D-Txg-Orn-Asp-Ile-N-MeChx-Trp; Seq ID No: 38
Fmoc-D-Txg-Asp-Asp-Ile-N-MeChx-Trp; Seq ID No: 24
Fmoc-D-Txg-Glu-Asp-Ile-N-MeChx-Trp; Seq ID No: 25
Et-D-Bhg-Leu-Asp-Ile-N-MeIle-Trp; Seq ID No: 20
Bz-D-Bhg-Leu-Asp-Ile-N-MeIle-Trp; Seq ID No: 20
Pya-D-Bhg-Leu-Asp-Ile-N-MeIle-Trp; Seq ID No: 20
Cxl-D-Bhg-Leu-Asp-Ile-N-MeIle-Trp; Seq ID No: 20
Ada-D-Bhg-Leu-Asp-Ile-N-MeIle-Trp; Seq ID No: 20
Cxl(U)-D-Bhg-Leu-Asp-Ile-N-MeIle-Trp; Seq ID No: 20
Me(U)-D-Bhg-Leu-Asp-Ile-N-MeIle-Trp; Seq ID No: 20
tBu-D-Bhg-Leu-Asp-Ile-N-MeIle-Trp; Seq ID No: 20
$CF_3CO$-D-Bhg-Leu-Asp-Ile-N-MeIle-Trp; Seq ID No: 20
Et-D-Bheg-Leu-Asp-Ile-N-MeIle-Trp; Seq ID No: 20
Bz-D-Bheg-Leu-Asp-Ile-N-MeIle-Trp; Seq ID No: 20
Pya-D-Bheg-Leu-Asp-Ile-N-MeIle-Trp; Seq ID No: 20
Cxl-D-Bheg-Leu-Asp-Ile-N-MeIle-Trp; Seq ID No: 20
Ada-D-Bheg-Leu-Asp-Ile-N-MeIle-Trp; Seq ID No: 20
Cxl(U)-D-Bheg-Leu-Asp-Ile-N-MeIle-Trp; Seq ID No: 20
Me(U)-D-Bheg-Leu-Asp-Ile-N-MeIle-Trp; Seq ID No: 20
tBu-D-Bheg-Leu-Asp-Ile-N-MeIle-Trp; Seq ID No: 20
$CF_3CO$-D-Bheg-Leu-Asp-Ile-N-MeIle-Trp; Seq ID No: 20
Ac-D-Bheg-Leu-D-Asp-Ile-Ile-Trp; Seq ID No: 20
Ac-D-Bheg-Leu-D-Asp-Ile-N-MeIle-Trp; Seq ID No: 20
Ac-D-Bhg-Leu-D-Asp-Ile-Ile-Trp; Seq ID No: 2
Ac-D-Bhg-Leu-D-Asp-Ile-N-MeIle-Trp; Seq ID No: 20
Ac-D-Bhg-Leu-Asp-Phe-N-MeIle-Trp; Seq ID No: 56
Ac-D-Bhg-Orn-Asp-Phe-N-MeIle-Trp; Seq ID No: 57
Ac-D-Bhg-Lys-Asp-Phe-N-MeIle-Trp; Seq ID No: 58
Ac-D-Bhg-Asp-Asp-Phe-N-MeIle-Trp; Seq ID No: 59
Ac-D-Bhg-Glu-Asp-Phe-N-MeIle-Trp; Seq ID No: 60
Ac-D-Bhg-Phe-Asp-Phe-N-MeIle-Trp; Seq ID No: 61
Ac-D-Bhg-Arg-Asp-Phe-N-MeIle-Trp; Seq ID No: 62
Ac-D-Bheg-Leu-Asp-Phe-N-MeIle-Trp; Seq ID No: 63
Ac-D-Bheg-Orn-Asp-Phe-N-MeIle-Trp; Seq ID No: 57
Ac-D-Bheg-Lys-Asp-Phe-N-MeIle-Trp; Seq ID No: 58
Ac-D-Bheg-Asp-Asp-Phe-N-MeIle-Trp; Seq ID No: 59
Ac-D-Bheg-Glu-Asp-Phe-N-MeIle-Trp; Seq ID No: 60
Ac-D-Bheg-Phe-Asp-Phe-N-MeIle-Trp; Seq ID No: 61
Ac-D-Bheg-Arg-Asp-Phe-N-MeIle-Trp; Seq ID No: 62

Ac-D-Bhg-Leu-N-MeAsp-Ile-Ile-Trp; and Seq ID No: 15
Ac-D-Bhg-Arg-Asp-Ile-Ile-Tyr(CHO); Seq ID No: 64
or a pharmaceutically acceptable acid or base addition salt thereof.

The compounds of Formula I are valuable antagonists of endothelin. The tests employed indicate that compounds of Formula I possess endothelin antagonist activity. Thus, the compounds of Formula I were tested for their ability to inhibit [$^{125}$I]-ET-1([$^{125}$I]-Endothelin-1) binding in a receptor assay according to the following procedures:

Endothelin Receptor Binding Assay-A (ERBA-A)
Intact Cell Binding of [$^{125}$I]-ET-1

Materials and Terms Used:
Cells

The cells used were rabbit renal artery vascular smooth muscle cells grown in a 48-well dish (1 cm$^2$) (confluent cells).

Growth Media

The growth media was Dulbecco's Modified Eagles/Ham's F12 which contained 10% fetal bovine serum and antibiotics (penicillin/streptomycin/fungizone).

Assay Buffer

The assay buffer was a medium 199 containing Hanks salts and 25 mM Hepes buffer (Gibco 380-2350AJ), supplemented with penicillin/streptomycin/fungizone (0.5%) and bovine serum albumin (1 mg/mL).

[$^{125}$I]-ET-1

Amersham radioiodinated endothelin-1 [$^{125}$I]-ET-1 was used at final concentration of 20,000 cpm/0.25 mL (25 pM).

Protocol

First, add 0.5 mL warm assay buffer (described above) to the aspirated growth media and preincubate for 2 to 3 hours in a 37° C. water bath (do not put back in the 5% carbon dioxide). Second, remove the assay buffers, place the dish on ice, and add 150 µL of cold assay buffer described above to each well. Third, add 50 mL each of cold [$^{125}$I]-ET-1 and competing ligand to the solution (at the same time if possible). Next, place dish in a 37° C. water bath for about 2 hours and gently agitate the dish every 15 minutes. Discard the radioactive incubation mixture in the sink and wash wells 3 times with 1 mL of cold phosphate buffered saline. Last, add 250 mL of 0.25 molar sodium hydroxide, agitate for 1 hour on a rotator, and then transfer the sodium hydroxide extract to gamma counting tubes and count the radioactivity.

Endothelin Receptor Binding Assay-B (ERBA-B)
[$^{125}$I]-ET-1 Binding in Rat Cerebellar Membranes Materials and Terms Used:
Tissue Buffer The tissue is made up of 20 mM tris(hydroxymethyl)aminomethane hydrochloride (Trizma) buffer, 2 mM ethylenediaminetetra acetate, 100 µM phenylmethylsulfonyl fluoride.

Tissue Preparation

First, thaw one aliquot of frozen rat cerebellar membranes (2 mg protein in 0.5 mL). Next, add 0.5 mL membrane aliquot to 4.5 mL cold tissue buffer, polytron at 7,500 revolutions per minute for 10 seconds. Finally, dilute tissue suspension 1/100 (0.1 mL suspension+ 9.9 mL tissue buffer), polytron again, and place ice.

Dilution Buffer

Medium 199 with Hank's salts plus 25 mM Hepes+1 mg/mL bovine serum albumin.

[$^{125}$I]-ET-1

Amersham [$^{125}$I]-ET-1 (aliquots of 2×10$^6$ cpm per 100 mL aliquot of [$^{125}$I]-ET-1 with 5.2 mL dilution buffer, place on ice until use (final concentration will be 20,000 cpm per tube, or 25 pM).

Protocol

Add 50 µL each of cold [$^{125}$]-ET-1 and competing ligand to tubes on ice. Mix in 150 µL of tissue to each tube, vortex briefly, then tap to force all liquids to bottom (total assay volume=250 µL). Then place the tubes in a 37° C. water bath for 2 hours.

Add 2.5 mL cold wash buffer (50 mM Trizma buffer) to each tube, filter, and then wash tube with additional 2.5 mL wash buffer and add to filter. Finally, wash filters with an additional 2.5 mL of cold wash buffer.

Count filters for radioactivity in gamma counter.

Human Endothelin Receptor Biding Assay-B
(hERBA-B) [$^{125}$I]-ET-1 Binding to Human Cloned Receptor Isolation of Human ETB Receptor cDNA A human placenta cDNA library was constructed in bacteriophage lambda gt11 and approximately 10$^6$ plaques were screened with a $^{32}$P-labelled 1.3 kilobase HindIII/XbaI restriction fragment of rat ETBR cDNA as a probe. Plaque hybridization was carried out for 16 hours at 42° C. in a solution containing 100 µg/mL calf thymus DNA, 1×Denhardt's solution, 5×sodium saline citrate (SSC), 50 mM sodium phosphate, and 0.1% sodium lauryl sulfate (SDS). The membranes were then washed twice for 30 minutes each in 2×SSC and 0.1% SDS at 42° C. A final wash was carried out in 0.5×SSC with 0.1% SDS at 55° C. The positive clones were purified and subcloned into a pUC19 plasmid. DNA sequencing was performed by the dideoxynucleotide chain termination method and human ETBR (h ETBR) was identified by reading both DNA strands.

Transfection Into CHO-K1 Cells

The 1.35 kb HindIII/XbaI restriction fragment of clone 12 of the hETBR was inserted into the eukaryotic expression vector pRcCMV (pRcCMV-hETBR). CHO-K1 cells were transfected with 20 µg of pRcCMV-hETBR by electroporation at 300 V, 800 µF, low ohms for 1 second. Cell populations expressing human ETBR were selected with G418 (0.5 mg/mL) and clonal cell lines were isolated from these selected cell populations by single cell cloning. Expression levels of human ETBR were determined by the receptor binding assay described below using [$^{125}$I]-ET-3 as the radioligand. CHO-K1 cells were grown in Ham's Nutrient Mixture F12 and Dulbecco's Eagle Medium (1:1) DME/F12 (1:1) supplemented with 10% fetal bovine serum and G418 (0.5 mg/mL).

Radioligand Binding Assays

Membranes were prepared from confluent transfected CHO-K1 cells by lysing cells in cold lysis buffer (5 mM N-[2-hydroxyethyl]piperazine-N'-[2-ethanesulfonic acid] (HEPES), 2 mM EDTA, pH 7.4), homogenizing with a Dounce "A" homogenizer, and centrifuging the homogenate at 30,000×g for 20 minutes at 4° C. Cell pellets were resuspended in cold buffer (50 mM Tris, 2 mM EDTA, 200 µM Pefabloc, 10 µM phosphoramidon, 10 µM leupeptin, 1 µM pepstatin, pH 7.4) and frozen at −80° C. until use. Membranes were thawed and homogenized with a Brinkmann Polytron (Westbury, N.Y.), then diluted in binding buffer (20 mM Tris, 2 mM EDTA, 100 µM Pefabloc, 100 µM bacitracin, pH 7.4). Radioligand and competing ligands were prepared in binding buffer containing 0.1% bovine serum albumin (BSA). Competition binding assays were initiated by combining membranes (0.7 μg human ETBR, 3 μg rat ETBR), [$^{125}$I]-ET-3 (30,000 cpm), and competing ligand in a final volume of 250 μL and incubating 2 hours at 37° C. The assay was terminated by filtration over Whatman GF/B filters which were presoaked with 50 mM Tris, pH 7.4, containing 0.2% BSA and 100 μM bacitracin. Nonspecific binding was defined as binding in the presence of 100 nM unlabelled ET-3, and specific binding was defined as total binding minus nonspecific binding. Specific binding was analyzed by nonlinear least squares curve fitting (InPlot, GraphPad Software, San Diego, Calif.).

In Vitro Inhibition of ET-1 Stimulated Arachidonic Acid Release in Cultured Rabbit Vascular Smooth Muscle Cells (AAR-A) or CHO Cells Expressing Rat Recombinant $ET_B$ Receptor (AAR-B) by Compounds of Formula I Antagonist activity is measured by the ability of added compounds to reduce endothelin-stimulated arachidonic acid release in cultured vascular smooth muscle cells as arachidonic acid release (AAR). [$^3$H] Arachidonic Acid Loading Media (LM) is DME/F12+0.5% fetal calf serum (FCS)×0.25 mCi/mL [$^3$H] arachidonic acid (Amersham). Confluent monolayers of cultured rabbit renal artery vascular smooth muscle cells (AAR-A) or CHO cells expressing rat recombinant $ET_B$ receptor (AAR-B) were incubated in 0.5 mL of the LM over 18 hours, at 37° C., in 5% $CO_2$. The LM was aspirated and the cells were washed once with the assay buffer (Hank's balanced salt solution [BSS]+10 mM HEPES+fatty acid-free BSA (1 mg/mL)), and incubated for 5 minutes with 1 mL of the prewarmed assay buffer. This solution was aspirated, followed by an additional 1 mL of prewarmed assay buffer, and further incubated for another 5 minutes. A final 5-minute incubation was carried out in a similar manner. The same procedure was repeated with the inclusion of 10 μL of the test compound (1 nM to 1 μM) and 10 μL ET-1 (0.3 nM) and the incubation was extended for 30 minutes. This solution was then collected, 10 μL of scintillation cocktail was added, and the amount of [$^3$H] arachidonic acid was determined in a liquid scintillation counter.

In Vitro Antagonism of ET-1 Stimulated Vasoconstriction in the Rabbit Femoral Artery ($ET_A$) and Sarafotoxin 6c Stimulated Vasoconstriction in the Rabbit Pulmonary Artery ($ET_B$)

Male New Zealand rabbits were killed by cervical dislocation and exsanguination. Femoral and pulmonary arteries were isolated, cleaned of connective tissue, and cut into 4-mm rings. The endothelium was denuded by placing the rings over hypodermic tubing (32 guage for femoral rings and 28 guage for pulmonary rings, Small Parts, Inc, Miami, Fla.) and gently rolling them. Denuded rings were mounted in 20 mL organ baths containing Krebs-bicarbonate buffer (composition in mM: NaCl, 118.2; $NaHCO_3$, 24.8; KCl, 4.6; $MgSO_4$ $7.H_2O$, 1.2; $KH_2PO_4$, 1.2; $CaCl_2.2H_2O$; Ca—$Na_2$ EDTA, 0.026; dextrose, 10.0), that was maintained at 37° C. and gassed continuously with 5% $CO_2$ in oxygen (pH 7.4). Resting tension was adjusted to 3.0 g for femoral and 4.0 g pulmonary arteries; the rings were left for 90 minutes to equilibrate. Vascular rings were tested for lack of functional endothelium (i.e., lack of an endothelium-dependent relaxation response to carbachol (1.0 μM) in norepinephrine (0.03 μM) contracted rings. Agonist peptides, ET-1 (femoral), and S6c (pulmonary), were cumulatively added at 10-minute intervals. The ET antagonists were added 30 minutes prior to adding the agonist and pA 2 values were calculated (Table II).

CaCO-2 Cell Transport and Stability in Rat Intestinal Perfusate of Endothelin Antagonists CaCO-2 Cell Transport Experiments CaCO-2 cells (human colon adenocarcinoma cell line) were grown in Corning T-75 tissue culture flasks and passed when 50% to 80% confluent to new flasks (25 mL medium per flask) using 1 mL of trypsin-EDTA and diluting with 10 mL media to stop trypsin activity. For experiments, the cells were counted, then diluted to $2.5 \times 10^5$ cells/mL for planting (400 μL per well) onto Snapwell culture membranes with 2.5 mL media in the lower chamber. Media in the Snapwells was changed every 2 to 3 days. Cells used for this series of experiments were between passage 38 and 91. 2-[N-Morpholino]ethanesulfonic acid (MES)+25 mM glucose was used as incubation buffer for all the experiments and all incubation solutions were prepared to an osmotic pressure of 280 to 300 milliosmoles. The concentration of the endothelin antagonist being studied (for all experiments) was 100 μM and another endothelin antagonist with similar HPLC characteristics (retention time 2–3 minutes from the ET antagonist being studied, and similar chemical characteristics) was used at a concentration of 25 μM as an internal standard to compensate for any injection error. Prior to the start of the experiment, the transepithelial electrical resistance (TEER) was measured for each Snapwell (in media) at three points of the membrane. Any membrane with large variations in the three values was not used as this suggested compromises to the cell monolayer. The membranes were washed by swirling in 0.9% normal saline and mounted in the pretreated diffusion chambers [0.1 mg/mL human serum albumin for 1 to 2 hours at 37° C. with $O_2$ bubbling followed by air drying at 37° C. overnight, then with 4.5 to 5.0 mL dosing solution (MES+glucose+$^{14}$C-PEG-4000 (5000 dpm/ 50 μL)+drug) for 5 minutes and 4.5 to 5.0 mL MES+glucose rinse just before the experiment.] The apical (donor) side was filled with 4.5 to 5.0 mL dosing solution, the basolateral (receiver) side with MES+glucose. Samples were removed from the donor and receiver compartments over the course of the experiment and analyzed for $^{14}$C-PEG 4000 (cell membrane integrity) and endothelin content. The amount of drug transferred as a function of time was used to calculate the apparent permeability, $$P_{app}=(V/(A*C_o))(dC/dt)$$

where V is the volume of the receiver chamber (4.5 or 5.0 mL), A is the exposed surface of the cell monolayer (1.13 $cm^2$), $C_o$ is the donor drug concentration, and dC/dt is the change in receiver drug concentration over time. The starting concentration of each diffusion chamber was used for its individual $C_o$ value. The values in Table II suggest that Examples 1, 16, and 19 may have 5–10% absorption in the gut.

Stability in Rat Intestinal Perfusate

For the stability experiments, male Wistar rats (250–350 g) were fasted overnight, then anesthetized with a cocktail of Ketamine/Xylasine (prepared just before injection) in the thigh muscle followed by pentobarbital injection in the alternate thigh muscle. After deep anesthesia, verified by loss of reflex reaction, a midline abdominal incision was made to open the peritoneal cavity. The ligament of Treitz was located and the jejunum was cannulated approximately 5 cm distal as well as 15 cm further distal to isolate that segment of intestine for perfusion. The segment was perfused for 90 minutes with MES buffer at a flow rate of 30 mL/minute using a Harvard Apparatus perfusion pump in the infuse/refill mode. The perfusate was kept at 37° C. for each experiment. An oscillating 37° C. water bath set to 90 cycles/minute was used for all samples. The experimental time course for the compounds studied was 0, 1, 3, 5, 7, 10, 15, 20, 30, 60, 90, 120, and 180 minutes (with some variations for individual compounds). The reactions were run as follows: 90 μL of perfusate plus 10 μL of endothelin antagonist (250 μM stock in MES buffer for most compounds) followed by brief vortexing and incubation for indicated time. The time zero was prepared by adding 100 μL ACN and 90 μL perfusate, vortexing, then adding 10 μL stock drug, vortexing. All samples were centrifuged for 10 minutes at 14,000 rpm in an Eppendorf centrifuge to pellet precipitated proteins. For HPLC analysis 50 μL of the final supernatant was injected and loss of parent and appearance of metabolites was examined. Half-life determinations were calculated based on loss of parent peak height using the calculation:

$$t^{1/2} = LN(2)/k$$

where k=slope of the initial linear range of the experiment.

The enzyme activity of leucine amino peptidase in the perfusate was determined as a convenient marker. The values in Table I show the enhanced stability of Example 19.

Liquid Scintillation Counting

Fifty microliter samples were collected from all time points and from each chamber, placed in 20-mL scintillation vials, 10 mL of Ready-Gel scintillant was added. All samples were allowed to stabilize for at least 1 hour prior to counting. The samples were counted in the Packard TriCarb 4000 for 5 minutes each in the dpm mode for 3 cycles to assure that no chemiluminescence was present. Typically the second and third counts were used in calculations. When membranes were analyzed for radiolabel uptake they were solubilized with 0.5 mL of Soluene-350 for at least 30 minutes then neutralized with 0.1 mL of a saturated solution of sodium pyruvate in methanol, glacial acetic acid, and methanol in the ratio of 4:3:1 by volume (PGM) followed by addition of scintillant (10 mL) and counting as indicated above.

HPLC (High Pressure Liquid Chromatography) Analysis

For CaCO-2 experiments 20 to 50 μL were removed from donor compartments, 150 to 200 μL from receiver compartments at each time point. Internal standard (solubilized in 95–99% ACN/H$_2$O) was measured to 1.5 mL Eppendorf tubes in an equal volume to the receiver volume collected (MES+glucose added to donor compartment tubes to equal receiver final volume) within 30 minutes of sampling time point. The time point aliquots were added to the Eppendorf tubes, mixed, then 125 μL was injected into the HPLC. When membranes were analyzed for endothelin uptake the cells were lysed by adding 250 μL 0.1X Triton vortexing briefly, sonicating 15 minutes, and rinsing the tube with an equal volume of ACN/Internal standard. A gradient HPLC method was used for all samples (CaCO-2 cell experiments and stability experiments): Mobile phase A=90% H$_2$O, 10% ACN, 0.1% TFA, pH 3.5; mobile phase B=24% H$_2$O, 76% ACN, 0.1% TFA, pH 3.5; 100% A to 100% B over 20 minutes, 100% B to 100% A from 20 to 22.5 minutes, and 100% A from 2.5 to 27 minutes. The pH of both mobile phases was adjusted after addition of all components with NaOH.

Leucine Amino Peptidase Analysis

To 0.9 mL MES buffer (blank) and 0.9 mL perfusate 0.1 mL L-Leucine-p-nitroanilide hydrochloride (LpNA) solution (1.44 mg/mL) was added. The solutions were mixed quickly and a 5-minute kinetics program was run on the Beckman DU-70 spectrophotometer (380 nM wavelength, 10-second time interval) to monitor the formation of p-nitroaniline.

Conscious Rat Duration of Action Study

Nonfasted rats (350–500 g) were used and anesthetized with Metofane (methoxyflurane) by inhalation. The rats were jugular cannulated (PE50) for IV administration of mecamylamine-HCl (MEC), ET-1 and Ac-D-Bhg-Leu-Asp-Ile-N-MeIle-Trp (Example 19) Seq ID No: 20, and carotid cannulated (PE50) for arterial blood pressure measurements. Rats were attached to a swivel for freedom of movement, and food and water were available ad lib. Prior to the experiment, the animals were allowed to recover from anesthesia for 60 minutes. The rats were ganglionically blocked with MEC 1.25 mg/kg IV 20 minutes prior to the ET-1 challenge. Ac-D-Bhg-Leu-Asp-Ile-N-MeIle-TrP (Example 19) Seq ID No: 20 was administered at a dose of 10 mg/kg IV. This compound inhibited ET-1 pressor activity by 81% and 58% at 5 and 30 minutes postdose, respectively (n=4 at each time point). This illustrates the prolonged activity of Ac-D-Bhg-Leu-Asp-Ile-N-MeIle-TrP (Example 19) Seq ID No: 20 in vivo.

Ischemia-Induced Acute Renal Failure Study

Male Sprague-Dawley rats (300–400 g) were housed in metabolic cages for 2 days before and 7 days after renal injury; urine output and plasma creatinine levels were monitored daily. On the day of renal injury, rats were anesthetized with sodium pentobarbital (50 mg/kg, IP) heparinized (50 units, IV), and instrumented with a tail vein canulae for drug or vehicle infusion. Both kidneys were exposed via a flank incision and the right kidney was removed. The left renal artery was clamped for 60 minutes and released. Example 1 was infused for 60 minutes prior to and following the ischemic period. Renal injury was evident 1 and 2 days following ischemia from a ten-fold increase in plasma creatine levels and significant decrease in urine output. Mortality occurred primarily between the second and third days post-injury. However, mortality was significantly less (52%, N=23) in rats treated with Example 1 compared to vehicle rats (83%, N=23). In addition, urine output on the second day following renal injury was significantly greater in Example 1 treated animals. Creatine levels were not significantly different between treatment groups on either the first or second days post-injury (Haleen S., et al., *FASEB J.*, April 1994). Therefore, these data show that Example 1 and related analogues in Table I are effective in a model of ischemia-induced acute renal failure.

The data in Table II below show the endothelin receptor binding, antagonist activity, CaCO-2 cell transport, metabolic stability, and effectiveness in a model of ischemia-induced acute renal failure of representative compounds of Formula I.

TABLE II

Biological Activity of Compounds of Formula I

| Example | Compound | ERBA-A IC$_{50}$ (μM) | ERRA-B IC$_{50}$ (μM) | hERBA-B IC$_{50}$ (μM) | AAR-A IC$_{50}$ (μM) | AAR-B IC$_{50}$ (μM) | pA$_2$ Femoral | pA$_2$ Pulmonary | Stability Rat Intestinal Perfusate (minutes) | CaCO-2 (cm/minute) | |
|---|---|---|---|---|---|---|---|---|---|---|---|
| 1 | Ac—D-Bhg—Leu—Asp—Ile—Ile—Trp | 0.0026 | 0.019 | 0.21 | 0.0049 | 0.02 | 6.8 | 7.1 | 10.6 ± 2.2 | 4.73 ± 0.86 | Seq ID No: 2 |
| 2 | D-Bhg—Leu—Asp—Ile—Ile—Trp | 0.45 | 2.1 | | 0.10 | 9.6 | 5.7 | | | | Seq ID No: 2 |
| 3 | L-Bhg—Leu—Asp—Ile—Ile—Trp | 2.5 | 3.0 | | 2.36 | | | | | | Seq ID No: 2 |
| 4 | Ac—L-Bhg—Leu—Asp—Ile—Ile—Trp | 0.56 | 0.71 | | 0.56 | | | | | | Seq ID No: 2 |
| 5 | Ac—D-Txg—Leu—Asp—Ile—Ile—Trp | 0.018 | 0.18 | | 0.05 | 0.062 | | | | | Seq ID No: 2 |
| 6 | Ac—D-Bheg—Leu—Asp—Ile—Ile—Trp | 0.005 | 0.019 | | 0.003 | 0.017 | 6.8 | 7.4 | | | Seq ID No: 2 |
| 7 | Ac—D-Bhg—Orn—Asp—Ile—Ile—Trp | 0.022 | 1.5 | | 0.037 | | 6.5 | | | | Seq ID No: 3 |
| 8 | Ac—D-Bhg—Glu—Asp—Ile—Ile—Trp | 0.0055 | 0.022 | | 0.007 | 0.027 | 6.5 | 7.0 | | | Seq ID No: 6 |
| 9 | Ac—L-Oxn—Lys—Asp—Ile—Ile—Trp | 0.05 | 0.93 | | | | | | | | Seq ID No: 4 |
| 10 | Ac—D-Oxn—Lys—Asp—Ile—Ile—Trp | 0.12 | 0.55 | | | | | | | | Seq ID No: 4 |
| 11 | L-Txg—Leu—Asp—Ile—Ile—Trp | 4.5 | 2.1 | | | | | | | | Seq ID No: 2 |
| 12 | Ac—L-Txg—Leu—Asp—Ile—Ile—Trp | 1.5 | 2.1 | | | | | | | | Seq ID No: 2 |
| 13 | D-Txg—Leu—Asp—Ile—Ile—Trp | 0.83 | 0.38 | | 0.32 | 2.4 | | | | | Seq ID No: 2 |
| 14 | Ac—D-Bhg—Arg—Asp—Ile—Ile—Trp | 0.0012 | 0.04 | | | | | | | | Seq ID No: 8 |
| 15 | Ac—D-Bhg—Leu—N-MeAsp—Ile—Ile—Trp | 0.44 | 1.9 | | | | | | | | Seq ID No: 15 |
| 16 | Ac—D-Bhg—Leu—D-Asp—Ile—Ile—Trp | 0.14 | 0.4 | | | | | | | 37.4 ± 6.4 | 0.95 ± 0.19 | Seq ID No: 2 |
| 17 | Ac—D-Bhg—Leu—Asp—Phe—Ile—Trp | 0.068 | 0.03 | | | | | | | | Seq ID No: 31 |
| 18 | Ac—D-Bhg—Arg—Asp—Ile—Ile—Trp (For) | 0.079 | 4.9 | | | | | | | | Seq ID No: 64 |
| 19 | Ac—D-Bhg—Leu—Asp—Ile—N-MeIle—Trp | 0.0005 | 0.04 | 0.025 | 0.0043 | | 7.3 | 6.6 | 538 ± 52 | 5.54 ± 2.24 | Seq ID No: 20 |

General Method for Preparing Compounds of Formula I

The compounds of Formula I may be prepared by solid phase peptide synthesis on a peptide synthesizer, for example, an Applied Biosystems 430A peptide synthesizer using activated esters or anhydrides of N-alpha-Boc protected amino acids, on PAM or MBHA resins. Additionally, the compounds of Formula I may also be prepared by conventional solution peptide synthesis. Amino acid side chains are protected as follows: Bzl (Asp, Glu, Ser), 2-Cl-Z(Lys), 2-Br-Z(Tyr), Bom(His), For(Trp), and MeBzl(Cys). Each peptide resin (1.0 g) is cleaved with 9 mL of HF and 1 mL of anisole or p-cresol as a scavenger (60 minutes, 0° C.). The peptide resin is washed with cyclohexane, extracted with 30% aqueous HOAc, followed by glacial HOAc, concentrated under reduced pressure, and lyophilized. (A peptide containing For(Trp) is dissolved in 0° C., the pH is adjusted to 12.5 with 1N KOH (2 minutes), neutralized with glacial HOAc, desalted on $C_{18}$ (as described below), and lyophilized. The crude peptide is purified by preparative reversed phase high performance liquid chromatography (RP-HPLC) on a $C_{18}$ column (2.2×25.0 cm, 15.0 mL/min) with a linear gradient of 0.1% TFA in water to 0.1% TFA in acetonitrile and lyophilized. The homogeneity and composition of the resulting peptide is verified by RP-HPLC, capillary electrophoresis, thin layer chromatography (TLC), proton nuclear magnetic resonance spectrometry (NMR), and fast atom bombardment mass spectrometry (FAB-MS).

The compounds of the present invention can be prepared and administered in a wide variety of oral and parenteral dosage forms. Thus, the compounds of the present invention can be administered by injection, that is, intravenously, intramuscularly, intracutaneously, subcutaneously, intraduodenally, or intraperitoneally. Also, the compounds of the present invention can be administered by inhalation, for example, intranasally. Additionally, the compounds of the present invention can be administered transdermally. It will be obvious to those skilled in the art that the following dosage forms may comprise as the active component, either a compound of Formula I or a corresponding pharmaceutically acceptable salt of a compound of Formula I.

For preparing pharmaceutical compositions from the compounds of the present invention, pharmaceutically acceptable carriers can be either solid or liquid. Solid form preparations include powders, tablets, pills, capsules, cachets, suppositories, and dispersible granules. A solid carrier can be one or more substances which may also act as diluents, flavoring agents, binders, preservatives, tablet disintegrating agents, or an encapsulating material.

In powders, the carrier is a finely divided solid which is in a mixture with the finely divided active component.

In tablets, the active component is mixed with the carrier having the necessary binding properties in suitable proportions and compacted in the shape and size desired.

The powders and tablets preferably contain from five or ten to about seventy percent of the active compound. Suitable carriers are magnesium carbonate, magnesium stearate, talc, sugar, lactose, pectin, dextrin, starch, gelatin, tragacanth, methylcellulose, sodium carboxymethylcellulose, a low melting wax, cocoa butter, and the like. The term "preparation" is intended to include the formulation of the active compound with encapsulating material as a carrier providing a capsule in which the active component with or without other carriers, is surrounded by a carrier, which is thus in association with it. Similarly, cachets and lozenges are included. Tablets, powders, capsules, pills, cachets, and lozenges can be used as solid dosage forms suitable for oral administration.

For preparing suppositories, a low melting wax, such as a mixture of fatty acid glycerides or cocoa butter, is first melted and the active component is dispersed homogeneously therein, as by stirring. The molten homogenous mixture is then poured into convenient sized molds, allowed to cool, and thereby to solidify.

Liquid form preparations include solutions, suspensions, and emulsions, for example, water or water propylene glycol solutions. For parenteral injection liquid preparations can be formulated in solution in aqueous polyethylene glycol solution.

Aqueous solutions suitable for oral use can be prepared by dissolving the active component in water and adding suitable colorants, flavors, stabilizing and thickening agents as desired.

Aqueous suspensions suitable for oral use can be made by dispersing the finely divided active component in water with viscous material, such as natural or synthetic gums, resins, methylcellulose, sodium carboxymethylcellulose, and other well-known suspending agents.

Also included are solid form preparations which are intended to be converted, shortly before use, to liquid form preparations for oral administration. Such liquid forms include solutions, suspensions, and emulsions. These preparations may contain, in addition to the active component, colorants, flavors, stabilizers, buffers, artificial and natural sweeteners, dispersants, thickeners, solubilizing agents, and the like.

The pharmaceutical preparation is preferably in unit dosage form. In such form the preparation is subdivided into unit doses containing appropriate quantities of the active component. The unit dosage form can be a packaged preparation, the package containing discrete quantities of preparation, such as packeted tablets, capsules, and powders in vials or ampoules. Also, the unit dosage form can be a capsules, tablet, cachet, or lozenge itself, or it can be the appropriate number of any of these in packaged form.

The quantity of active component in a unit dose preparation may be varied or adjusted from 0.1 mg to 100 mg preferably 0.5 mg to 100 mg according to the particular application and the potency of the active component. The composition can, if desired, also contain other compatible therapeutic agents.

In therapeutic use as antagonist of endothelin, the compounds utilized in the pharmaceutical method of this invention are administered at the initial dosage of about 0.01 mg to about 20 mg per kilogram daily. A daily dose range of about 0.01 mg to about 10 mg per kilogram is preferred. The dosages, however, may be varied depending upon the requirements of the patient, the severity of the condition being treated, and the compound being employed. Determination of the proper dosage for a particular situation is within the skill of the art. Generally, treatment is initiated with smaller dosages which are less than the optimum dose of the compound. Thereafter, the dosage is increased by small increments until the optimum effect under the circumstances is reached. For convenience, the total daily dosage may be divided and administered in portions during the day, if desired.

The following nonlimiting examples illustrate the inventors' preferred methods for preparing the compounds of the invention.

EXAMPLE 1

Ac-D-Bhg-Leu-Asp-Ile-Ile,Trp Seq ID No: 2

The linear hexapeptide is prepared by standard solid phase synthetic peptide methodology utilizing a Boc/benzyl strategy (Stewart J. M. and Young J. D., *Solid Phase Peptide Synthesis*, Pierce Chemical Co., Rockford, Ill., 1984). All protected amino acids and reagents are obtained from commercial sources with the exception of N-α-Boc-DL-Bhg and are not further purified. The protected peptide resin is prepared on an Applied Biosystems 430A Peptide Synthesizer, utilizing protocols supplied for a dicyclohexylcarbodiimide-mediated coupling scheme (Standard 1.0, Version 1.40). Starting with 0.710 g of N-α-Boc-Trp-PAM resin (0.70 meq/g, 0.497 meq of Boc-Trp(For) total) the protected peptide is prepared by the stepwise coupling of the following amino acids (in order of addition): N-α-Boc-Ile.0.5H$_2$O, N-α-Boc-Ile.0.5H$_2$O, N-α-Boc-Asp(Bzl), N-α-Boc-Leu·H$_2$O, and N-α-Boc-DL-Bhg. A typical cycle for the coupling of an individual amino acid residue is illustrated below (reproduced from the ABI manual):

All the single couple RV cycles conform to the following pattern:

1) 33% TFA in DCM for 80 seconds
2) 50% TFA in DCM for 18.5 minutes
3) Three DCM washes
4) 10% DIEA in DMF for 1 minute
5) 10% DIEA in DMF for 1 minute
6) Five DMF washes
7) Coupling period
8) Five DCM washes After the coupling of N-α-Boc-DL-Bhg, the Boc group is removed with the end-NH$_2$ cycle (1.012 g).

The peptide is liberated from the solid support, and the carboxylate of aspartic acid deprotected by treatment with anhydrous hydrogen fluoride (9.0 mL), anisole (0.5 mL), and dimethyl sulfide (0.5 mL) (60 minutes, 0° C.). After removing the hydrogen fluoride under a stream of nitrogen, the resin is washed with diethyl ether (3×30 mL) and extracted with 20% HOAc in water (3×30 mL) and glacial HOAc (2×30 mL). The aqueous extractions are combined, concentrated under reduced pressure, and lyophilized (360 mg). The crude peptide is dissolved in 4.0 mL of 50% TFA/H$_2$O, filtered through a 0.4 L syringe filter, and chromatographed on a Vydac 218TP 1022 column (2.2×25.0 cm, 15.0 mL/min, A: 0.1% TFA/H$_2$O, B: 0.1% TFA/CH$_3$CN, Gradient; 0% B for 10 minutes, 10% to 40% B over 120 minutes). Two individual fractions are collected and combined based upon analysis by analytical HPLC. The combined fractions are concentrated separately under reduced pressure (10 mL), diluted with H$_2$O (50 mL), and lyophilized (40.0 mg/ea). Separation into the two diastereomers (Isomers A and B) is effected under these conditions (t$_R$= Isomer A 15.63 min., Isomer B 16.79 min.). The late running peak fractions (Isomer B) are repurified under the same experimental conditions with a gradient of 30% to 50% B over 120 minutes at 15 mL/min to afford purified product. Acetylation is carried out with 20 mg of Isomer B in 90% acetic acid followed by addition of acetic anhydride (5 mL) and stirring overnight. After evaporation and drying the product Ac-D-Bhg-Leu-Asp-Ile-Ile-Trp Seq ID No: 2 is 99% pure by HPLC. [Vydac 218 TP 1022 column (2.2×25.0 cm, 15.0 mL/min. A: 0.1% TFA/CH$_3$CN, Gradient 20% to 86% B over 22 min.)] t$_R$=18.66 minutes. The homogeneity and structure of the resulting peptide is confirmed by analytical HPLC. Proton Nuclear Magnetic Resonance Spectroscopy (H$^1$-NMR) and Fast Atom Bombardment Mass Spectroscopy (FAB-MS), M+Na 972.0, M+2Na$^+$995.9.

In a process analogous to Example 1 using the appropriate amino acids, the corresponding compounds of Formula I are prepared as follows:

EXAMPLE 2

D-Bhg-Leu-Asp-Ile-Ile-Trp; FAB-MS, M+1 907.4. Seq ID No: 2

EXAMPLE 3

L-Bhg-Leu-Asp-Ile-Ile-Trp; FAB-MS, M+1 907.4. Seq ID No: 2

EXAMPLE 4

Ac-L-Bhg-Leu-Asp-Ile-Ile-Trp; FAB-MS, M+1 950.0. Seq ID No: 2

EXAMPLE 5

Ac-D-Txg-Leu-Asp-Ile-Ile-Trp; FAB-MS, M+Na 977.0. Seq ID No: 2

EXAMPLE 6

Ac-D-Bheg-Leu-Asp-Ile-Ile-Trp; FAB-MS, M+Na 970.3. Seq ID No: 2

EXAMPLE 7

Ac-D-Bhg-Orn-Asp-Ile-Ile-Trp; FAB-MS, M+1 951.2. Seq ID No: 3

EXAMPLE 8

Ac-D-Bhg-Glu-Asp-Ile-Ile-Trp; FAB-MS, M+Na 988.8. Seq ID No: 6

EXAMPLE 9

Ac-L-Oxn-Leu-Asp-Ile-Ile-Trp; FAB-MS, M+1 936.6. Seq ID No: 4

EXAMPLE 10

Ac-D-Oxn-Leu-Asp-Ile-Ile-Trp; FAM-MS, M+1 936.6. Seq ID No: 4

EXAMPLE 11

L-Txg-Leu-Asp-Ile-Ile-Trp; FAB-MS, M+1 913.1. Seq ID No: 2

EXAMPLE 12

Ac-L-Txg-Leu-Asp-Ile-Ile-Trp; FAB-MS, M+Na 977.2. Seq ID No: 2

EXAMPLE 13

D-Txg-Leu-Asp-Ile-Ile-Trp; FAB-MS, M+1 912.2. Seq ID No: 2

EXAMPLE 14

Ac-D-Bhg-Arg-ASp-Ile-Ile-Trp; FAB-MS, M+1 994.6. Seq ID No: 8

EXAMPLE 15

Ac-D-Bhg-Leu-N-MeAsp-Ile-Ile-Trp; M+1 964.0. Seq ID No: 15

EXAMPLE 16

Ac-D-Bhg-Leu-D-Asp-Ile-Ile-Trp; FAB-MS, M+1 950.4. Seq ID No: 2

EXAMPLE 17

Ac-D-Bhg-Leu-Asp-Phe-Ile-Trp; FAB-MS, M+Na 1006.5. Seq ID No: 31

EXAMPLE 18

Ac-D-Bhg-Arg-Asp-Ile-Ile-Trp(For); FAB-MS, M+1 1021.6. Seq ID No: 64

EXAMPLE 19

Ac-D-Bhg-Leu-Asp-Ile-N-MeIle-Trp; FAB-MS, M+1 963.6. Seq ID No: 20

EXAMPLE 20

Disodium salt of Ac-D-Bhg-Leu-Asp-Ile-Ile-Trp Seq ID No: 2

A saturated solution of sodium bicarbonate in water is prepared, diluted with water (1:10), chilled to 0° C., and 10 mL of the solution is added to approximately 50 mg of Ac-D-Bhg-Leu-Asp-Ile-Ile-Trp Seq ID No: 2 (Example 1) with stirring. The pH of the solution is greater than 9. After 10 minutes, the solution is passed through a C18 cartridge, washed with water (100 mL), and the absorbed peptide is eluted with methanol (50 mL), concentrated under reduced pressure, resuspended in water (50 mL), and lyophilized (three times) to give the title compound.

Ac-D-Bhg-Leu-Asp-Ile-Ile-Trp, disodium salt; FAB-MS, M+1 950.4, M+Na 972.1, M+2Na 994.3. Seq ID No: 2

EXAMPLE 21

Boc-Bhg

Bhg.HCl (1.70 g, 5.43 mmol) is suspended in 150 mL of p-dioxane: $H_2O$ (2:1) at room temperature. To the stirred solution is added 1.40 g (6.42 mmol) of di-tert butyldicarbonate. The pH of the solution is adjusted to >9.0 with 1N NaOH and maintained at between pH 9 and 10 with aliquot additions of 1N NaOH, until the pH is constant. The solution is concentrated under reduced pressure to approximately 75 mL, overlain with ethyl acetate (50 mL), and acidified to approximately pH 2.5 with 10% aqueous HCl. The organic layer is separated, washed successively with 10% aqueous HCl (2×50 mL), brine (2×50 mL), $H_2O$ (3×50 mL), and dried with $MgSO_4$. The solution is filtered, concentrated under reduced pressure, and the oil is recrystallized from ethyl acetate:heptane (1.82 g). The white solid is characterized by proton NMR, fast atom bombardment mass spectrometry (M+1=368), and elemental analysis.

---

We claim:

1. A compound of Formula I $$AA^1\text{-}AA^2\text{-}AA^3\text{-}AA^4\text{-}AA^5\text{-}AA^6 \qquad \text{Seq ID No: 1}$$

wherein $AA^1$ is

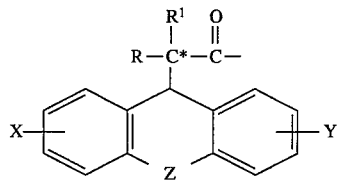

wherein R is hydrogen,
alkyl,
alkenyl,
alkynyl,
cycloalkyl,
cycloalkylalkyl,
aryl,
heteroaryl,
fluorenylmethyl,

wherein $R^2$ and $R^3$ are each the same or different and each is
hydrogen,
alkyl,
alkenyl,
alkynyl,
cycloalkyl,
cycloalkylalkyl,
aryl,
arylalkyl,
heteroaryl, or
fluorenylmethyl,

wherein $R^2$ is as defined above,
—$OR^2$, wherein $R^2$ is as defined above,

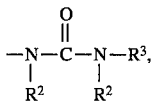

wherein $R^2$ and $R^3$ are as defined above,

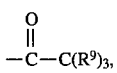

wherein $R^9$ is F, Cl, Br, or I,
—$CH_2$—$OR^2$, wherein $R^2$ is as defined above,

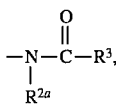

wherein $R^{2a}$ is hydrogen or alkyl and $R^3$ is as defined above,

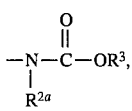

wherein $R^{2a}$ and $R^3$ are as defined above excluding $R^3$ is hydrogen, or

wherein $R^2$ is as defined above,
$R^1$ is hydrogen or alkyl,
Z is
—O—,

—S(O)$_m$—, wherein m is zero or an integer of 1 or 2,

wherein R$^2$ is as defined above,
—(CH$_2$)$_n$—, wherein n is zero or an integer of 1, 2, 3, or 4,
—(CH$_2$)$_n$—CH=CH—(CH$_2$)$_{n'}$—, wherein n and n' are each independently the same or different and each is as defined above for n,

wherein R$^1$ and R$^2$ are as defined above, or

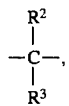

wherein R$^2$ and R$^3$ are each the same or different and each is as defined above, X and Y are the same and substituted at the same position on the aromatic ring and each may be 1, 2, 3, or 4 substituents selected from the group consisting of
hydrogen,
halogen,
alkyl,
—CO$_2$R$^2$, wherein R$^2$ is as defined above

wherein R$^2$ and R$^3$ are as defined above,

wherein R$^2$ and R$^3$ are as defined above, and
nitro or

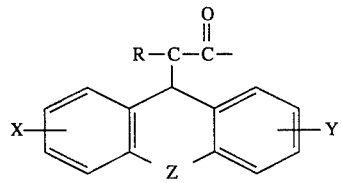

wherein R, Z, X, and Y are as defined above;
AA$^2$ is

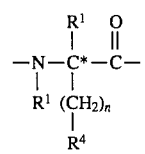

wherein R$^4$ is
hydrogen,
alkyl,
alkenyl,
alkynyl,
cycloalkyl,
aryl,
heteroaryl,

wherein R$^{2b}$ and R$^{3b}$ are each the same or different and each is
hydrogen,
alkyl,
cycloalkyl,
aryl, or
heteroaryl,
—OR$^{2b}$, wherein R$^{2b}$ is as defined above,

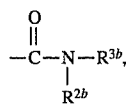

wherein R$^{2b}$ and R$^{3b}$ are each the same or different and each is as defined above for R$^{2b}$ and R$^{3b}$,

wherein R$^{2b}$ is as defined above,

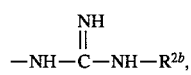

wherein R$^{2b}$ is as defined above, or

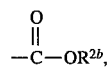

wherein R$^{2b}$ is as defined above, and
R$^1$ and n are as defined above, or AA$^2$ is absent;
AA$^3$ is

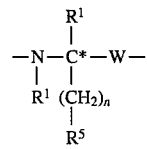

wherein W is

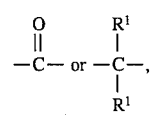

R$^5$ is
hydrogen,
alkyl,
aryl, heteroaryl,

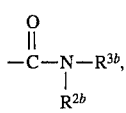

wherein $R^{2b}$ and $R^{3b}$ are each the same or different and each is as defined above,

wherein $R^{2b}$ is as defined above, or

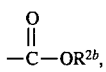

wherein $R^{2b}$ is as defined above, and
$R^1$ and n are as defined above, or $AA^3$ is absent;
$AA^4$ and $AA^5$ are each independently absent or each is independently

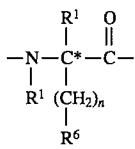

wherein $R^6$ is hydrogen,
alkyl,
alkenyl,
alkynyl,
cycloalkyl,
aryl, or
heteroaryl, and
$R^1$ and n are as defined above;
$AA^6$ is

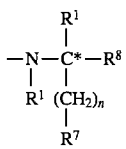

wherein $R^7$ is
aryl or
heteroaryl,
$R^8$ is

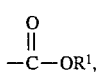

wherein $R^1$ is as defined above,
—$OR^1$, wherein $R^1$ is as defined above,

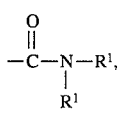

wherein $R^1$ is as defined above, or
—$CH_2$—$OR^1$, wherein $R^1$ is as defined above, and
$R^1$ and n are as defined above;
stereochemistry at C* in $AA^1$, $AA^2$, $AA^3$, $AA^4$, or $AA^5$ is D, L, or DL and stereochemistry at C* in $AA^6$ is L;

or a pharmaceutically acceptable salt thereof.

2. A compound according to claim 1, in which $AA^1$ is

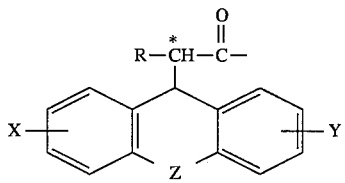

wherein R is

wherein $R^2$ and $R^3$ are each the same or different and each is
hydrogen,
alkyl,
alkenyl,
alkynyl,
cycloalkyl,
cycloalkylalkyl,
aryl,
arylalkyl,
heteroaryl, or
fluorenylmethyl,

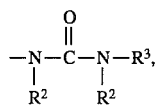

wherein $R^2$ and $R^3$ are as defined above,

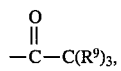

wherein $R^9$ is F, Cl, Br, or I,

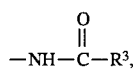

wherein $R^3$ is as defined above, or

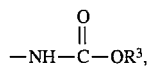

wherein $R^3$ is as defined above excluding $R^3$ is hydrogen;
Z is —O—,
—$S(O)_m$—, wherein m is zero or an integer of 1 or 2,

wherein $R^2$ is as defined above,
—$(CH_2)_n$—, wherein n is zero or an integer of 1, 2, 3, or 4,
—$(CH_2)_n$—CH=CH—$(CH_2)_{n'}$—, wherein n and n' are each independently the same or different and each is as defined above for n,

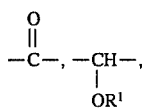

wherein $R^1$ is hydrogen or alkyl, or

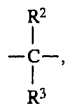

wherein $R^2$ and $R^3$ are each the same or different and each is as defined above and X and Y are the same and substituted at the same position on the aromatic ring and each substituent is selected from the group consisting of
hydrogen,
halogen, and
alkyl;

$AA^2$ is

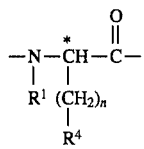

wherein $R^4$ is hydrogen,
alkyl,
alkenyl,
alkynyl,
cycloalkyl,
aryl,
heteroaryl,

wherein $R^{2b}$ and $R^{3b}$ are each the same or different and each is
hydrogen,
alkyl,
cycloalkyl,
aryl, or
heteroaryl,
—$OR^{2b}$, wherein $R^{2b}$ is as defined above,

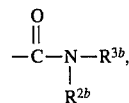

wherein $R^{2b}$ and $R^{3b}$ are each the same or different and each is as defined above for $R^{2b}$ and $R^{3b}$,

wherein $R^{2b}$ is as defined above,

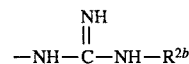

wherein $R^{2b}$ is as defined above, or

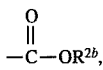

wherein $R^{2b}$ is as defined above, and $R^1$ and n are as defined above or $AA^2$ is absent;

$AA^3$ is

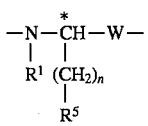

wherein W is

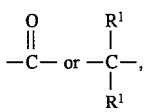

$R^5$ is aryl,
heteroaryl,

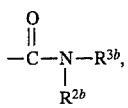

wherein $R^{2b}$ and $R^{3b}$ are each the same or different and each is as defined above,

wherein $R^{2b}$ is as defined above, or

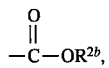

wherein $R^{2b}$ is as defined above, and $R^1$ and n are as defined above, or $AA^3$ is absent;

$AA^4$ and $AA^5$ are each independently absent or each is independently

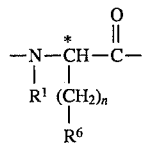

wherein $R^6$ is hydrogen
alkyl,
alkenyl,
alkynyl,
cycloalkyl,
aryl, or
heteroaryl, and $R^1$ and n are as defined above;

AA$^6$ is $$-\overset{|}{\underset{\underset{R^7}{|}}{\overset{|}{N}}}-\overset{*}{\underset{\underset{(CH_2)_n}{|}}{C}H}-CO_2H$$

wherein R$^7$ is aryl or
heteroaryl, and
R$^1$ and n are as defined above, or $$-\overset{|}{\underset{\underset{R^7}{|}}{\overset{|}{N}}}-\overset{*}{\underset{\underset{(CH_2)_n}{|}}{C}H}-\overset{O}{\overset{||}{C}}-\overset{|}{\underset{R^1}{N}}-R^1$$

wherein R$^7$, R$^1$, and n are as defined above;
stereochemistry at C*H in AA$^1$, AA$^2$, AA$^3$, AA$^4$, or AA$^5$ is D, L, or DL and stereochemistry at C*H in AA$^6$ is L;
or a pharmaceutically acceptable salt thereof.

3. A compound according to claim 2, in which AA$^1$ is $$R-\overset{*}{C}H-\overset{O}{\overset{||}{C}}-$$

(attached to diphenylmethane with X, Y, Z substituents)

wherein R is $$-\overset{|}{\underset{R^3}{N}}-R^2,$$

wherein R$^2$ and R$^3$ are each the same or different and each is
hydrogen,
alkyl,
aryl, or
fluorenylmethyl, $$-\overset{|}{\underset{R^2}{N}}-\overset{O}{\overset{||}{C}}-\overset{|}{\underset{R^2}{N}}-R^3,$$

wherein R$^2$ and R$^3$ are as defined above, $$-\overset{O}{\overset{||}{C}}-C(R^9)_3,$$

wherein R$^9$ is F, Cl, Br, or I, $$-NH-\overset{O}{\overset{||}{C}}-R^3,$$

wherein R$^3$ is as defined above, or $$-NH-\overset{O}{\overset{||}{C}}-OR^{10},$$

wherein R$^{10}$ is alkyl, aryl, arylalkyl, or fluorenylmethyl,

Z is

—O—,
—S—,
—NH—,
—(CH$_2$)$_n$, wherein n is zero or an integer of 1, 2, 3, or 4, or
—(CH$_2$)$_{n^a}$—CH=CH—(CH$_2$)$_{n^{1-a}}$—, wherein n$^a$ and n$^{a-1}$ are each independently the same or different and each is zero or an integer of 1 or 2 and X and Y are each the same and substituted at the same position on the aromatic ring and each substituent is selected from the group consisting of
hydrogen,
halogen, and
alkyl;

AA$^2$ is $$-\overset{|}{\underset{\underset{R^4}{|}}{\overset{|}{N}}}-\overset{*}{\underset{\underset{(CH_2)_n}{|}}{C}H}-\overset{O}{\overset{||}{C}}-,$$

wherein R$^{1'}$ is hydrogen or methyl,
R$^4$ is hydrogen,
alkyl,
aryl,
heteroaryl, $$-\overset{|}{\underset{R^{2b}}{N}}-R^{3b},$$

wherein R$^{2b}$ and R$^{3b}$ are each the same or different and each is hydrogen or alkyl, $$-\overset{O}{\overset{||}{C}}-\overset{|}{\underset{R^{2b}}{N}}-R^{3b},$$

wherein R$^{2b}$ and R$^{3b}$ are each the same or different and each is hydrogen or alkyl, $$-NH-\overset{NH}{\overset{||}{C}}-NH-R^{2b},$$

wherein R$^{2b}$ is as defined above, or $$-\overset{O}{\overset{||}{C}}-OR^{2b},$$

wherein is R$^{2b}$ is as defined above, and
n is zero or an integer of 1, 2, 3, or 4 or AA$^2$ is absent;

AA$^3$ is $$-\overset{|}{\underset{\underset{R^5}{|}}{\overset{|}{N}}}-\overset{*}{\underset{\underset{(CH_2)_n}{|}}{C}H}-W-,$$

wherein W is

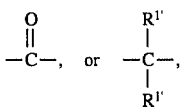

R⁵ is
aryl,
heteroaryl,

wherein $R^{3b}$ is hydrogen or alkyl,

wherein $R^{2b}$ is hydrogen or alkyl, or

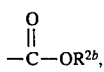

wherein $R^{2b}$ is hydrogen or alkyl, and
$R^{1'}$ and n are as defined above;
$AA^4$ and $AA^5$ are each independently

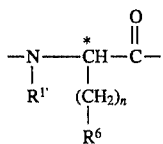

wherein $R^6$ is hydrogen,
alkyl,
cycloalkyl, or
aryl, and
$R^{1'}$ and n are as defined above;
$AA^6$ is

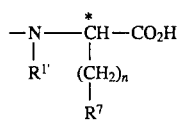

wherein $R^7$ is aryl or
heteroaryl, and
$R^{1'}$ and n are as defined above, or

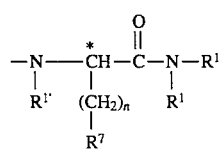

wherein $R^7$, $R^1$, $R^{1'}$, and n are as defined above;
stereochemistry at C*H in $AA^1$, $AA^2$, $AA^3$, $AA^4$, or $AA^5$ is
D, L, or DL and stereochemistry at C*H in $AA^6$ is L;
or a pharmaceutically acceptable salt thereof.

4. A compound according to claim 3 selected from the group consisting of:
L-Bhg-Leu-Asp-Ile-Ile-Trp; Seq ID No: 2
D-Bhg-Leu-Asp-Ile-Ile-Trp; Seq ID No: 2
Ac-L-Bhg-Leu-Asp-Ile-Ile-Trp; Seq ID No: 2
Ac-D-Bhg-Leu-Asp-Ile-Ile-Trp; Seq ID No: 2
Ac-D-Bhg-Orn-Asp-Ile-Ile-Trp; Seq ID No: 3
Ac-D-Bhg-Lys-Asp-Ile-Ile-Trp; Seq ID No: 4
Ac-D-Bhg-Asp-Asp-Ile-Ile-Trp; Seq ID No: 5
Ac-D-Bhg-Glu-Asp-Ile-Ile-Trp; Seq ID No: 6
Ac-D-Bhg-Phe-Asp-Ile-Ile-Trp; Seq ID No: 7
Ac-D-Bhg-Arg-Asp-Ile-Ile-Trp; Seq ID No: 8
Ac-D-Bhg-Asp-Ile-Ile-Trp; Seq ID No: 9
Fmoc-D-Bhg-Leu-Asp-Ile-Ile-Trp; Seq ID No: 2
Fmoc-D-Bhg-Orn-Asp-Ile-Ile-Trp; Seq ID No: 3
Fmoc-D-Bhg-Lys-Asp-Ile-Ile-Trp; Seq ID No: 4
Fmoc-D-Bhg-Asp-Asp-Ile-Ile-Trp; Seq ID No: 5
Fmoc-D-Bhg-Glu-Asp-Ile-Ile-Trp; Seq ID No: 6
Fmoc-D-Bhg-Phe-Asp-Ile-Ile-Trp; Seq ID No: 7
Fmoc-D-Bhg-Arg-Asp-Ile-Ile-Trp; Seq ID No: 8
Fmoc-D-Bhg-Asp-Ile-Ile-Trp; Seq ID No: 9
Ac-D-Bhg-Leu-Phe-Ile-Ile-Trp; Seq ID No: 10
Ac-D-Bhg-Leu-Asn-Ile-Ile-Trp; Seq ID No: 11
Ac-D-Bhg-Leu-Glu-Ile-Ile-Trp; Seq ID No: 12
Ac-D-Bhg-Leu-Gln-Ile-Ile-Trp; Seq ID No: 13
Ac-D-Bhg-Leu-Tyr-Ile-Ile-Trp; Seq ID No: 14
Ac-D-Bhg-Leu-1-Nal-Ile-Ile-Trp; Seq ID No: 15
Ac-D-Bhg-Leu-2-Nal-Ile-Ile-Trp; Seq ID No: 15
Ac-D-Bhg-Leu-Trp-Ile-Ile-Trp; Seq ID No: 16
Ac-D-Bhg-Leu-Asp-Val-Ile-Trp; Seq ID No: 17
Ac-D-Bhg-Leu-Asp-Ile-Val-Trp; Seq ID No: 18
Ac-D-Bhg-Leu-Asp-Chx-Ile-Trp; Seq ID No: 19
Ac-D-Bhg-Leu-Asp-Ile-Chx-Trp; Seq ID No: 20
Ac-D-Bhg-Arg-Asp-Ile-Chx-Trp; Seq ID No: 21
Ac-D-Bhg-Lys-Asp-Ile-Chx-Trp; Seq ID No: 22
Ac-D-Bhg-Orn-Asp-Ile-Chx-Trp; Seq ID No: 23
Ac-D-Bhg-Asp-Asp-Ile-Chx-Trp; Seq ID No: 24
Ac-D-Bhg-Glu-Asp-Ile-Chx-Trp; Seq ID No: 25
Fmoc-D-Bhg-Leu-Phe-Ile-Ile-Trp; Seq ID No: 10
Fmoc-D-Bhg-Leu-Asn-Ile-Ile-Trp; Seq ID No: 11
Fmoc-D-Bhg-Leu-Glu-Ile-Ile-Trp; Seq ID No: 12
Fmoc-D-Bhg-Leu-Gln-Ile-Ile-Trp; Seq ID No: 13
Fmoc-D-Bhg-Leu-Tyr-Ile-Ile-Trp; Seq ID No: 14
Fmoc-D-Bhg-Leu-Asp-Val-Ile-Trp; Seq ID No: 17
Fmoc-D-Bhg-Leu-Asp-Ile-Val-Trp; Seq ID No: 18
Fmoc-D-Bhg-Leu-Asp-Chx-Ile-Trp; Seq ID No: 19
Fmoc-D-Bhg-Arg-Asp-Chx-Ile-Trp; Seq ID No: 26
Fmoc-D-Bhg-Lys-Asp-Chx-Ile-Trp; Seq ID No: 27
Fmoc-D-Bhg-Orn-Asp-Chx-Ile-Trp; Seq ID No: 28
Fmoc-D-Bhg-Asp-Asp-Chx-Ile-Trp; Seq ID No: 29
Fmoc-D-Bhg-Glu-Asp-Chx-Ile-Trp; Seq ID No: 30
Fmoc-D-Bhg-Leu-Asp-Ile-Chx-Trp; Seq ID No: 20
Fmoc-D-Bhg-Arg-Asp-Ile-Chx-Trp; Seq ID No: 21
Fmoc-D-Bhg-Lys-Asp-Ile-Chx-Trp; Seq ID No: 22
Fmoc-D-Bhg-Orn-Asp-Ile-Chx-Trp; Seq ID No: 23
Fmoc-D-Bhg-Asp-Asp-Ile-Chx-Trp; Seq ID No: 24
Fmoc-D-Bhg-Glu-Asp-Ile-Chx-Trp; Seq ID No: 25
Ac-D-Bheg-Leu-Asp-Ile-Ile-Trp; Seq ID No: 2
Ac-D-Bheg-Orn-Asp-Ile-Ile-Trp; Seq ID No: 3
Ac-D-Bheg-Lys-Asp-Ile-Ile-Trp; Seq ID No: 4
Ac-D-Bheg-Asp-Asp-Ile-Ile-Trp; Seq ID No: 5
Ac-D-Bheg-Glu-Asp-Ile-Ile-Trp; Seq ID No: 6
Ac-D-Bheg-Phe-Asp-Ile-Ile-Trp; Seq ID No: 7
Ac-D-Bheg-Arg-Asp-Ile-Ile-Trp; Seq ID No: 8
Ac-D-Bheg-Asp-Ile-Ile-Trp; Seq ID No: 9
Fmoc-D-Bheg-Leu-Asp-Ile-Ile-Trp; Seq ID No: 2
Fmoc-D-Bheg-Orn-Asp-Ile-Ile-Trp; Seq ID No: 3
Fmoc-D-Bheg-Lys-Asp-Ile-Ile-Trp; Seq ID No: 4
Fmoc-D-Bheg-Asp-Asp-Ile-Ile-Trp; Seq ID No: 5
Fmoc-D-Bheg-Glu-Asp-Ile-Ile-Trp; Seq ID No: 6
Fmoc-D-Bheg-Phe-Asp-Ile-Ile-Trp; Seq ID No: 7
Fmoc-D-Bheg-Arg-Asp-Ile-Ile-Trp; Seq ID No: 8

Fmoc-D-Bheg-Asp-Ile-Ile-Trp; Seq ID No: 9
Ac-D-Bheg-Leu-Phe-Ile-Ile-Trp; Seq ID No: 10
Ac-D-Bheg-Leu-Asn-Ile-Ile-Trp; Seq ID No: 11
Ac-D-Bheg-Leu-Glu-Ile-Ile-Trp; Seq ID No: 12
Ac-D-Bheg-Leu-Gln-Ile-Ile-Trp; Seq ID No: 13
Ac-D-Bheg-Leu-Tyr-Ile-Ile-Trp; Seq ID No: 14
Ac-D-Bheg-Leu-1-Nal-Ile-Ile-Trp; Seq ID No: 15
Ac-D-Bheg-Leu-2-Nal-Ile-Ile-Trp; Seq ID No: 15
Ac-D-Bheg-Leu-Trp-Ile-Ile-Trp; Seq ID No: 16
Ac-D-Bheg-Leu-Asp-Val-Ile-Trp; Seq ID No: 17
Ac-D-Bheg-Leu-Asp-Ile-Val-Trp; Seq ID No: 18
Ac-D-Bheg-Leu-Asp-Chx-Ile-Trp; Seq ID No: 19
Ac-D-Bheg-Leu-Asp-Ile-Chx-Trp; Seq ID No: 20
Ac-D-Bheg-Arg-Asp-Ile-Chx-Trp; Seq ID No: 21
Ac-D-Bheg-Lys-Asp-Ile-Chx-Trp; Seq ID No: 22
Ac-D-Bheg-Orn-Asp-Ile-Chx-Trp; Seq ID No: 23
Ac-D-Bheg-Asp-Asp-Ile-Chx-Trp; Seq ID No: 24
Ac-D-Bheg-Glu-Asp-Ile-Chx-Trp; Seq ID No: 25
Fmoc-D-Bheg-Leu-Phe-Ile-Ile-Trp; Seq ID No: 10
Fmoc-D-Bheg-Leu-Asn-Ile-Ile-Trp; Seq ID No: 11
Fmoc-D-Bheg-Leu-Glu-Ile-Ile-Trp; Seq ID No: 12
Fmoc-D-Bheg-Leu-Gln-Ile-Ile-Trp; Seq ID No: 13
Fmoc-D-Bheg-Leu-Tyr-Ile-Ile-Trp; Seq ID No: 14
Fmoc-D-Bheg-Leu-Asp-Val-Ile-Trp; Seq ID No: 17
Fmoc-D-Bheg-Leu-Asp-Ile-Val-Trp; Seq ID No: 18
Fmoc-D-Bheg-Leu-Asp-Chx-Ile-Trp; Seq ID No: 19
Fmoc-D-Bheg-Arg-Asp-Chx-Ile-Trp; Seq ID No: 26
Fmoc-D-Bheg-Lys-Asp-Chx-Ile-Trp; Seq ID No: 27
Fmoc-D-Bheg-Orn-Asp-Chx-Ile-Trp; Seq ID No: 28
Fmoc-D-Bheg-Asp-Asp-Chx-Ile-Trp; Seq ID No: 29
Fmoc-D-Bheg-Glu-Asp-Chx-Ile-Trp; Seq ID No: 30
Fmoc-D-Bheg-Leu-Asp-Ile-Chx-Trp; Seq ID No: 20
Fmoc-D-Bheg-Arg-Asp-Ile-Chx-Trp; Seq ID No: 21
Fmoc-D-Bheg-Lys-Asp-Ile-Chx-Trp; Seq ID No: 22
Fmoc-D-Bheg-Orn-Asp-Ile-Chx-Trp; Seq ID No: 23
Fmoc-D-Bheg-Asp-Asp-Ile-Chx-Trp; Seq ID No: 24
Fmoc-D-Bheg-Glu-Asp-Ile-Chx-Trp; Seq ID No: 25
Ac-D-Txg-Leu-Asp-Ile-Ile-Trp; Seq ID No: 2
Ac-D-Txg-Orn-Asp-Ile-Ile-Trp; Seq ID No: 3
Ac-D-Txg-Lys-Asp-Ile-Ile-Trp; Seq ID No: 4
Ac-D-Txg-Asp-Asp-Ile-Ile-Trp; Seq ID No: 5
Ac-D-Txg-Glu-Asp-Ile-Ile-Trp; Seq ID No: 6
Ac-D-Txg-Phe-Asp-Ile-Ile-Trp; Seq ID No: 7
Ac-D-Txg-Arg-Asp-Ile-Ile-Trp; Seq ID No: 8
Ac-D-Txg-Asp-Ile-Ile-Trp; Seq ID No: 9
Fmoc-D-Txg-Leu-Asp-Ile-Ile-Trp; Seq ID No: 2
Fmoc-D-Txg-Orn-Asp-Ile-Ile-Trp; Seq ID No: 3
Fmoc-D-Txg-Lys-Asp-Ile-Ile-Trp; Seq ID No: 4
Fmoc-D-Txg-Asp-Asp-Ile-Ile-Trp; Seq ID No: 5
Fmoc-D-Txg-Glu-Asp-Ile-Ile-Trp; Seq ID No: 6
Fmoc-D-Txg-Phe-Asp-Ile-Ile-Trp; Seq ID No: 7
Fmoc-D-Txg-Arg-Asp-Ile-Ile-Trp; Seq ID No: 8
Fmoc-D-Txg-Asp-Ile-Ile-Trp; Seq ID No: 9
Ac-D-Txg-Leu-Phe-Ile-Ile-Trp; Seq ID No: 10
Ac-D-Txg-Leu-Asn-Ile-Ile-Trp; Seq ID No: 11
Ac-D-Txg-Leu-Glu-Ile-Ile-Trp; Seq ID No: 12
Ac-D-Txg-Leu-Gln-Ile-Ile-Trp; Seq ID No: 13
Ac-D-Txg-Leu-Tyr-Ile-Ile-Trp; Seq ID No: 14
Ac-D-Txg-Leu-1-Nal-Ile-Ile-Trp; Seq ID No: 15
Ac-D-Txg-Leu-2-Nal-Ile-Ile-Trp; Seq ID No: 15
Ac-D-Txg-Leu-Trp-Ile-Ile-Trp; Seq ID No: 16
Ac-D-Txg-Leu-Asp-Val-Ile-Trp; Seq ID No: 17
Ac-D-Txg-Leu-Asp-Ile-Val-Trp; Seq ID No: 18
Ac-D-Txg-Leu-Asp-Chx-Ile-Trp; Seq ID No: 19
Ac-D-Txg-Leu-Asp-Ile-Chx-Trp; Seq ID No: 20
Ac-D-Txg-Arg-Asp-Ile-Chx-Trp; Seq ID No: 21
Ac-D-Txg-Lys-Asp-Ile-Chx-Trp; Seq ID No: 22
Ac-D-Txg-Orn-Asp-Ile-Chx-Trp; Seq ID No: 23
Ac-D-Txg-Asp-Asp-Ile-Chx-Trp; Seq ID No: 24
Ac-D-Txg-Glu-Asp-Ile-Chx-Trp; Seq ID No: 25
Fmoc-D-Txg-Leu-Phe-Ile-Ile-Trp; Seq ID No: 10
Fmoc-D-Txg-Leu-Asn-Ile-Ile-Trp; Seq ID No: 11
Fmoc-D-Txg-Leu-Glu-Ile-Ile-Trp; Seq ID No: 12
Fmoc-D-Txg-Leu-Gln-Ile-Ile-Trp; Seq ID No: 13
Fmoc-D-Txg-Leu-Tyr-Ile-Ile-Trp; Seq ID No: 14
Fmoc-D-Txg-Leu-Asp-Val-Ile-Trp; Seq ID No: 17
Fmoc-D-Txg-Leu-Asp-Ile-Val-Trp; Seq ID No: 18
Fmoc-D-Txg-Leu-Asp-Chx-Ile-Trp; Seq ID No: 19
Fmoc-D-Txg-Arg-Asp-Chx-Ile-Trp; Seq ID No: 26
Fmoc-D-Txg-Lys-Asp-Chx-Ile-Trp; Seq ID No: 27
Fmoc-D-Txg-Orn-Asp-Chx-Ile-Trp; Seq ID No: 28
Fmoc-D-Txg-Asp-Asp-Chx-Ile-Trp; Seq ID No: 29
Fmoc-D-Txg-Glu-Asp-Chx-Ile-Trp; Seq ID No: 30
Fmoc-D-Txg-Leu-Asp-Ile-Chx-Trp; Seq ID No: 20
Fmoc-D-Txg-Arg-Asp-Ile-Chx-Trp; Seq ID No: 21
Fmoc-D-Txg-Lys-Asp-Ile-Chx-Trp; Seq ID No: 22
Fmoc-D-Txg-Orn-Asp-Ile-Chx-Trp; Seq ID No: 23
Fmoc-D-Txg-Asp-Asp-Ile-Chx-Trp; Seq ID No: 24
Fmoc-D-Txg-Glu-Asp-Ile-Chx-Trp; Seq ID No: 25
Et-D-Bhg-Leu-Asp-Ile-Ile-Trp; Seq ID No: 2
Bz-D-Bhg-Leu-Asp-Ile-Ile-Trp; Seq ID No: 2
Pya-D-Bhg-Leu-Asp-Ile-Ile-Trp; Seq ID No: 2
Cxl-D-Bhg-Leu-Asp-Ile-Ile-Trp; Seq ID No: 2
Ada-D-Bhg-Leu-Asp-Ile-Ile-Trp; Seq ID No: 2
Cxl(U)-D-Bhg-Leu-Asp-Ile-Ile-Trp; Seq ID No: 2
Me(U)-D-Bhg-Leu-Asp-Ile-Ile-Trp; Seq ID No: 2
tBu-D-Bhg-Leu-Asp-Ile-Ile-Trp; Seq ID No: 2
$CF_3CO$-D-Bhg-Leu-Asp-Ile-Ile-Trp; Seq ID No: 2
Et-D-Bheg-Leu-Asp-Ile-Ile-Trp; Seq ID No: 2
Bz-D-Bheg-Leu-Asp-Ile-Ile-Trp; Seq ID No: 2
Pya-D-Bheg-Leu-Asp-Ile-Ile-Trp; Seq ID No: 2
Cxl-D-Bheg-Leu-Asp-Ile-Ile-Trp; Seq ID No: 2
Ada-D-Bheg-Leu-Asp-Ile-Ile-Trp; Seq ID No: 2
Cxl(U)-D-Bheg-Leu-Asp-Ile-Ile-Trp; Seq ID No: 2
Me(U)-D-Bheg-Leu-Asp-Ile-Ile-Trp; Seq ID No: 2
tBu-D-Bheg-Leu-Asp-Ile-Ile-Trp; Seq ID No: 2
$CF_3CO$-D-Bheg-Leu-Asp-Ile-Ile-Trp; Seq ID No: 2
Ac-D-Bhg-Leu-Asp-Phe-Ile-Trp; Seq ID No: 31
Ac-D-Bhg-Orn-Asp-Phe-Ile-Trp; Seq ID No: 32
Ac-D-Bhg-Lys-Asp-Phe-Ile-Trp; Seq ID No: 33
Ac-D-Bhg-Asp-Asp-Phe-Ile-Trp; Seq ID No: 34
Ac-D-Bhg-Glu-Asp-Phe-Ile-Trp; Seq ID No: 35
Ac-D-Bhg-Phe-Asp-Phe-Ile-Trp; Seq ID No: 36
Ac-D-Bhg-Arg-Asp-Phe-Ile-Trp; Seq ID No: 37
Ac-D-Bheg-Leu-Asp-Phe-Ile-Trp; Seq ID No: 31
Ac-D-Bheg-Orn-Asp-Phe-Ile-Trp; Seq ID No: 32
Ac-D-Bheg-Lys-Asp-Phe-Ile-Trp; Seq ID No: 33
Ac-D-Bheg-Asp-Asp-Phe-Ile-Trp; Seq ID No: 34
Ac-D-Bheg-Glu-Asp-Phe-Ile-Trp; Seq ID No: 35
Ac-D-Bheg-Phe-Asp-Phe-Ile-Trp; Seq ID No: 36
Ac-D-Bheg-Arg-Asp-Phe-Ile-Trp; Seq ID No: 37
L-Bhg-Leu-Asp-Ile-N-MeIle-Trp; Seq ID No: 20
D-Bhg-Leu-Asp-Ile-N-MeIle-Trp; Seq ID No: 20
Ac-L-Bhg-Leu-Asp-Ile-N-MeIle-Trp; Seq ID No: 20
Ac-D-Bhg-Leu-Asp-Ile-N-MeIle-Trp; Seq ID No: 20
Ac-D-Bhg-Orn-Asp-Ile-N-MeIle-Trp; Seq ID No: 38
Ac-D-Bhg-Lys-Asp-Ile-N-MeIle-Trp; Seq ID No: 22
Ac-D-Bhg-Asp-Asp-Ile-N-MeIle-Trp; Seq ID No: 24
Ac-D-Bhg-Glu-Asp-Ile-N-MeIle-Trp; Seq ID No: 25
Ac-D-Bhg-Phe-Asp-Ile-N-MeIle-Trp; Seq ID No: 39
Ac-D-Bhg-Arg-Asp-Ile-N-MeIle-Trp; Seq ID No: 21
Ac-D-Bhg-Asp-Ile-N-MeIle-Trp; Seq ID No: 40
Fmoc-D-Bhg-Leu-Asp-Ile-N-MeIle-Trp; Seq ID No: 20
Fmoc-D-Bhg-Orn-Asp-Ile-N-MeIle-Trp; Seq ID No: 38

Fmoc-D-Bhg-Lys-Asp-Ile-N-MeIle-Trp; Seq ID No: 22
Fmoc-D-Bhg-Asp-Asp-Ile-N-MeIle-Trp; Seq ID No: 24
Fmoc-D-Bhg-Glu-Asp-Ile-N-MeIle-Trp; Seq ID No: 25
Fmoc-D-Bhg-Phe-Asp-Ile-N-MeIle-Trp; Seq ID No: 39
Fmoc-D-Bhg-Arg-Asp-Ile-N-MeIle-Trp; Seq ID No: 21
Fmoc-D-Bhg-Asp-Ile-N-MeIle-Trp; Seq ID No: 40
Ac-D-Bhg-Leu-Phe-Ile-N-MeIle-Trp; Seq ID No: 41
Ac-D-Bhg-Leu-Asn-Ile-N-MeIle-Trp; Seq ID No: 20
Ac-D-Bhg-Leu-Glu-Ile-N-MeIle-Trp; Seq ID No: 42
Ac-D-Bhg-Leu-Gln-Ile-N-MeIle-Trp; Seq ID No: 43
Ac-D-Bhg-Leu-Tyr-Ile-N-MeIle-Trp; Seq ID No: 44
Ac-D-Bhg-Leu-1-Nal-Ile-N-MeIle-Trp; Seq ID No: 45
Ac-D-Bhg-Leu-2-Nal-Ile-N-MeIle-Trp; Seq ID No: 45
Ac-D-Bhg-Leu-Trp-Ile-N-MeIle-Trp; Seq ID No: 46
Ac-D-Bhg-Leu-Asp-Val-N-MeIle-Trp; Seq ID No: 47
Ac-D-Bhg-Leu-Asp-Ile-N-MeVal-Trp; Seq ID No: 20
Ac-D-Bhg-Leu-Asp-Chx-N-MeIle-Trp; Seq ID No: 48
Ac-D-Bhg-Leu-Asp-Ile-N-MeChx-Trp; Seq ID No: 20
Ac-D-Bhg-Arg-Asp-Ile-N-MeChx-Trp; Seq ID No: 21
Ac-D-Bhg-Lys-Asp-Ile-N-MeChx-Trp; Seq ID No: 22
Ac-D-Bhg-Orn-Asp-Ile-N-MeChx-Trp; Seq ID No: 38
Ac-D-Bhg-Asp-Asp-Ile-N-MeChx-Trp; Seq ID No: 24
Ac-D-Bhg-Glu-Asp-Ile-N-MeChx-Trp; Seq ID No: 25
Fmoc-D-Bhg-Leu-Phe-Ile-N-MeIle-Trp; Seq ID No: 41
Fmoc-D-Bhg-Leu-Asn-Ile-N-MeIle-Trp; Seq ID No: 20
Fmoc-D-Bhg-Leu-Glu-Ile-N-MeIle-Trp; Seq ID No: 42
Fmoc-D-Bhg-Leu-Gln-Ile-N-MeIle-Trp; Seq ID No: 43
Fmoc-D-Bhg-Leu-Tyr-Ile-N-MeIle-Trp; Seq ID No: 44
Fmoc-D-Bhg-Leu-Asp-Val-N-MeIle-Trp; Seq ID No: 47
Fmoc-D-Bhg-Leu-Asp-Ile-N-MeVal-Trp; Seq ID No: 20
Fmoc-D-Bhg-Leu-Asp-Chx-N-MeIle-Trp; Seq ID No: 49
Fmoc-D-Bhg-Arg-Asp-Chx-N-MeIle-Trp; Seq ID No: 50
Fmoc-D-Bhg-Lys-Asp-Chx-N-MeIle-Trp; Seq ID No: 51
Fmoc-D-Bhg-Orn-Asp-Chx-N-MeIle-Trp; Seq ID No: 52
Fmoc-D-Bhg-Asp-Asp-Chx-N-MeIle-Trp; Seq ID No: 53
Fmoc-D-Bhg-Glu-Asp-Chx-N-MeIle-Trp; Seq ID No: 54
Fmoc-D-Bhg-Leu-Asp-Ile-N-MeChx-Trp; Seq ID No: 20
Fmoc-D-Bhg-Arg-Asp-Ile-N-MeChx-Trp; Seq ID No: 21
Fmoc-D-Bhg-Lys-Asp-Ile-N-MeChx-Trp; Seq ID No: 22
Fmoc-D-Bhg-Orn-Asp-Ile-N-MeChx-Trp; Seq ID No: 38
Fmoc-D-Bhg-Asp-Asp-Ile-N-MeChx-Trp; Seq ID No: 24
Fmoc-D-Bhg-Glu-Asp-Ile-N-MeChx-Trp; Seq ID No: 25
Ac-D-Bheg-Leu-Asp-Ile-N-MeIle-Trp; Seq ID No: 20
Ac-D-Bheg-Orn-Asp-Ile-N-MeIle-Trp; Seq ID No: 38
Ac-D-Bheg-Lys-Asp-Ile-N-MeIle-Trp; Seq ID No: 22
Ac-D-Bheg-Asp-Asp-Ile-N-MeIle-Trp; Seq ID No: 24
Ac-D-Bheg-Glu-Asp-Ile-N-MeIle-Trp; Seq ID No: 25
Ac-D-Bheg-Phe-Asp-Ile-N-MeIle-Trp; Seq ID No: 39
Ac-D-Bheg-Arg-Asp-Ile-N-MeIle-Trp; Seq ID No: 21
Fmoc-D-Bheg-Leu-D-Asp-Ile-N-MeIle-Trp; Seq ID No: 40
Fmoc-D-Bheg-Leu-Asp-Ile-N-MeIle-Trp; Seq ID No: 20
Fmoc-D-Bheg-Orn-Asp-Ile-N-MeIle-Trp; Seq ID No: 38
Fmoc-D-Bheg-Lys-Asp-Ile-N-MeIle-Trp; Seq ID No: 22
Fmoc-D-Bheg-Asp-Asp-Ile-N-MeIle-Trp; Seq ID No: 24
Fmoc-D-Bheg-Glu-Asp-Ile-N-MeIle-Trp; Seq ID No: 25
Fmoc-D-Bheg-Phe-Asp-Ile-N-MeIle-Trp; Seq ID No: 39
Fmoc-D-Bheg-Arg-Asp-Ile-N-MeIle-Trp; Seq ID No: 21
Fmoc-D-Bheg-Asp-Ile-N-MeIle-Trp; Seq ID No: 40
Ac-D-Bheg-Leu-Phe-Ile-N-MeIle-Trp; Seq ID No: 41
Ac-D-Bheg-Leu-Asn-Ile-N-MeIle-Trp; Seq ID No: 55
Ac-D-Bheg-Leu-Glu-Ile-N-MeIle-Trp; Seq ID No: 42
Ac-D-Bheg-Leu-Gln-Ile-N-MeIle-Trp; Seq ID No: 43
Ac-D-Bheg-Leu-Tyr-Ile-N-MeIle-Trp; Seq ID No: 44
Ac-D-Bheg-Leu-1-Nal-Ile-N-MeIle-Trp; Seq ID No: 45
Ac-D-Bheg-Leu-2-Nal-Ile-N-MeIle-Trp; Seq ID No: 45
Ac-D-Bheg-Leu-Trp-Ile-N-MeIle-Trp; Seq ID No: 46
Ac-D-Bheg-Leu-Asp-Val-N-MeIle-Trp; Seq ID No: 47
Ac-D-Bheg-Leu-Asp-Ile-N-MeVal-Trp; Seq ID No: 20
Ac-D-Bheg-Leu-Asp-Chx-N-MeIle-Trp; Seq ID No: 49
Ac-D-Bheg-Leu-Asp-Ile-N-MeChx-Trp; Seq ID No: 20
Ac-D-Bheg-Arg-Asp-Ile-N-MeChx-Trp; Seq ID No: 21
Ac-D-Bheg-Lys-Asp-Ile-N-MeChx-Trp; Seq ID No: 22
Ac-D-Bheg-Orn-Asp-Ile-N-MeChx-Trp; Seq ID No: 38
Ac-D-Bheg-Asp-Asp-Ile-N-MeChx-Trp; Seq ID No: 24
Ac-D-Bheg-Glu-Asp-Ile-N-MeChx-Trp; Seq ID No: 25
Fmoc-D-Bheg-Leu-Phe-Ile-N-MeIle-Trp; Seq ID No: 41
Fmoc-D-Bheg-Leu-Asn-Ile-N-MeIle-Trp; Seq ID No: 55
Fmoc-D-Bheg-Leu-Glu-Ile-N-MeIle-Trp; Seq ID No: 42
Fmoc-D-Bheg-Leu-Gln-Ile-N-MeIle-Trp; Seq ID No: 43
Fmoc-D-Bheg-Leu-Tyr-Ile-N-MeIle-Trp; Seq ID No: 44
Fmoc-D-Bheg-Leu-Asp-Val-N-MeIle-Trp; Seq ID No: 47
Fmoc-D-Bheg-Leu-Asp-Ile-N-MeVal-Trp; Seq ID No: 20
Fmoc-D-Bheg-Leu-Asp-Chx-N-MeIle-Trp; Seq ID No: 49
Fmoc-D-Bheg-Arg-Asp-Chx-N-MeIle-Trp; Seq ID No: 50
Fmoc-D-Bheg-Lys-Asp-Chx-N-MeIle-Trp; Seq ID No: 51
Fmoc-D-Bheg-Orn-Asp-Chx-N-MeIle-Trp; Seq ID No: 52
Fmoc-D-Bheg-Asp-Asp-Chx-N-MeIle-Trp; Seq ID No: 53
Fmoc-D-Bheg-Glu-Asp-Chx-N-MeIle-Trp; Seq ID No: 54
Fmoc-D-Bheg-Leu-Asp-Ile-N-MeChx-Trp; Seq ID No: 20
Fmoc-D-Bheg-Arg-Asp-Ile-N-MeChx-Trp; Seq ID No: 21
Fmoc-D-Bheg-Lys-Asp-Ile-N-MeChx-Trp; Seq ID No: 22
Fmoc-D-Bheg-Orn-Asp-Ile-N-MeChx-Trp; Seq ID No: 38
Fmoc-D-Bheg-Asp-Asp-Ile-N-MeChx-Trp; Seq ID No: 24
Fmoc-D-Bheg-Glu-Asp-Ile-N-MeChx-Trp; Seq ID No: 25
Fmoc-D-Bheg-Leu-D-Asp-Ile-Ile-Trp; Seq ID No: 2
Fmoc-D-Bheg-Leu-D-Asp-Ile-N-MeIle-Trp; Seq ID No: 20
Fmoc-D-Bhg-Leu-D-Asp-Ile-Ile-Trp; Seq ID No: 2
Fmoc-D-Bhg-Leu-D-Asp-Ile-N-MeIle-Trp; Seq ID No: 20
Ac-D-Txg-Leu-Asp-Ile-N-MeIle-Trp; Seq ID No: 20
Ac-D-Txg-Orn-Asp-Ile-N-MeIle-Trp; Seq ID No: 38
Ac-D-Txg-Lys-Asp-Ile-N-MeIle-Trp; Seq ID No: 22
Ac-D-Txg-Asp-Asp-Ile-N-MeIle-Trp; Seq ID No: 24
Ac-D-Txg-Glu-Asp-Ile-N-MeIle-Trp; Seq ID No: 25
Ac-D-Txg-Phe-Asp-Ile-N-MeIle-Trp; Seq ID No: 39
Ac-D-Txg-Arg-Asp-Ile-N-MeIle-Trp; Seq ID No: 21
Ac-D-Txg-Asp-Ile-N-MeIle-Trp; Seq ID No: 40
Fmoc-D-Txg-Leu-Asp-Ile-N-MeIle-Trp; Seq ID No: 20
Fmoc-D-Txg-Orn-Asp-Ile-N-MeIle-Trp; Seq ID No: 38
Fmoc-D-Txg-Lys-Asp-Ile-N-MeIle-Trp; Seq ID No: 22
Fmoc-D-Txg-Asp-Asp-Ile-N-MeIle-Trp; Seq ID No: 24
Fmoc-D-Txg-Glu-Asp-Ile-N-MeIle-Trp; Seq ID No: 25
Fmoc-D-Txg-Phe-Asp-Ile-N-MeIle-Trp; Seq ID No: 39
Fmoc-D-Txg-Arg-Asp-Ile-N-MeIle-Trp; Seq ID No: 21
Fmoc-D-Txg-Asp-Ile-N-MeIle-Trp; Seq ID No: 56
Ac-D-Txg-Leu-Phe-Ile-N-MeIle-Trp; Seq ID No: 41
Ac-D-Txg-Leu-Asn-Ile-N-MeIle-Trp; Seq ID No: 55
Ac-D-Txg-Leu-Glu-Ile-N-MeIle-Trp; Seq ID No: 42
Ac-D-Txg-Leu-Gln-Ile-N-MeIle-Trp; Seq ID No: 43
Ac-D-Txg-Leu-Tyr-Ile-N-MeIle-Trp; Seq ID No: 44
Ac-D-Txg-Leu-1-Nal-Ile-N-MeIle-Trp; Seq ID No: 45
Ac-D-Txg-Leu-2-Nal-Ile-N-MeIle-Trp; Seq ID No: 45
Ac-D-Txg-Leu-Trp-Ile-N-MeIle-Trp; Seq ID No: 46
Ac-D-Txg-Leu-Asp-Val-N-MeIle-Trp; Seq ID No: 47
Ac-D-Txg-Leu-Asp-Ile-N-MeVal-Trp; Seq ID No: 20
Ac-D-Txg-Leu-Asp-Chx-N-MeIle-Trp; Seq ID No: 49
Ac-D-Txg-Leu-Asp-Ile-N-MeChx-Trp; Seq ID No: 20
Ac-D-Txg-Arg-Asp-Ile-N-MeChx-Trp; Seq ID No: 21
Ac-D-Txg-Lys-Asp-Ile-N-MeChx-Trp; Seq ID No: 22
Ac-D-Txg-Orn-Asp-Ile-N-MeChx-Trp; Seq ID No: 38
Ac-D-Txg-Asp-Asp-Ile-N-MeChx-Trp; Seq ID No: 24
Ac-D-Txg-Glu-Asp-Ile-N-MeChx-Trp; Seq ID No: 25
Fmoc-D-Txg-Leu-Phe-Ile-N-MeIle-Trp; Seq ID No: 41
Fmoc-D-Txg-Leu-Asn-Ile-N-MeIle-Trp; Seq ID No: 55
Fmoc-D-Txg-Leu-Glu-Ile-N-MeIle-Trp; Seq ID No: 42

Fmoc-D-Txg-Leu-Gln-Ile-N-MeIle-Trp; Seq ID No: 43
Fmoc-D-Txg-Leu-Tyr-Ile-N-MeIle-Trp; Seq ID No: 44
Fmoc-D-Txg-Leu-Asp-Val-N-MeIle-Trp; Seq ID No: 47
Fmoc-D-Txg-Leu-Asp-Ile-N-MeVal-Trp; Seq ID No: 20
Fmoc-D-Txg-Leu-Asp-Chx-N-MeIle-Trp; Seq ID No: 49
Fmoc-D-Txg-Arg-Asp-Chx-N-MeIle-Trp; Seq ID No: 50
Fmoc-D-Txg-Lys-Asp-Chx-N-MeIle-Trp; Seq ID No: 51
Fmoc-D-Txg-Orn-Asp-Chx-N-MeIle-Trp; Seq ID No: 52
Fmoc-D-Txg-Asp-Asp-Chx-N-MeIle-Trp; Seq ID No: 53
Fmoc-D-Txg-Glu-Asp-Chx-N-MeIle-Trp; Seq ID No: 54
Fmoc-D-Txg-Leu-Asp-Ile-N-MeChx-Trp; Seq ID No: 20
Fmoc-D-Txg-Arg-Asp-Ile-N-MeChx-Trp; Seq ID No: 21
Fmoc-D-Txg-Lys-Asp-Ile-N-MeChx-Trp; Seq ID No: 22
Fmoc-D-Txg-Orn-Asp-Ile-N-MeChx-Trp; Seq ID No: 38
Fmoc-D-Txg-Asp-Asp-Ile-N-MeChx-Trp; Seq ID No: 24
Fmoc-D-Txg-Glu-Asp-Ile-N-MeChx-Trp; Seq ID No: 25
Et-D-Bhg-Leu-Asp-Ile-N-MeIle-Trp; Seq ID No: 20
Bz-D-Bhg-Leu-Asp-Ile-N-MeIle-Trp; Seq ID No: 20
Pya-D-Bhg-Leu-Asp-Ile-N-MeIle-Trp; Seq ID No: 20
Cxl-D-Bhg-Leu-Asp-Ile-N-MeIle-Trp; Seq ID No: 20
Ada-D-Bhg-Leu-Asp-Ile-N-MeIle-Trp; Seq ID No: 20
Cxl(U)-D-Bhg-Leu-Asp-Ile-N-MeIle-Trp; Seq ID No: 20
Me(U)-D-Bhg-Leu-Asp-Ile-N-MeIle-Trp; Seq ID No: 20
tBu-D-Bhg-Leu-Asp-Ile-N-MeIle-Trp; Seq ID No: 20
$CF_3CO$-D-Bhg-Leu-Asp-Ile-N-MeIle-Trp; Seq ID No: 20
Et-D-Bheg-Leu-Asp-Ile-N-MeIle-Trp; Seq ID No: 20
Bz-D-Bheg-Leu-Asp-Ile-N-MeIle-Trp; Seq ID No: 20
Pya-D-Bheg-Leu-Asp-Ile-N-MeIle-Trp; Seq ID No: 20
Cxl-D-Bheg-Leu-Asp-Ile-N-MeIle-Trp; Seq ID No: 20
Ada-D-Bheg-Leu-Asp-Ile-N-MeIle-Trp; Seq ID No: 20
Cxl(U)-D-Bheg-Leu-Asp-Ile-N-MeIle-Trp; Seq ID No: 20
Me(U)-D-Bheg-Leu-Asp-Ile-N-MeIle-Trp; Seq ID No: 20
tBu-D-Bheg-Leu-Asp-Ile-N-MeIle-Trp; Seq ID No: 20
$CF_3CO$-D-Bheg-Leu-Asp-Ile-N-MeIle-Trp; Seq ID No: 20
Ac-D-Bheg-Leu-D-Asp-Ile-Ile-Trp; Seq ID No: 20
Ac-D-Bheg-Leu-D-Asp-Ile-N-MeIle-Trp; Seq ID No: 20
Ac-D-Bhg-Leu-D-Asp-Ile-Ile-Trp; Seq ID No: 2
Ac-D-Bhg-Leu-D-Asp-Ile-N-MeIle-Trp; Seq ID No: 20
Ac-D-Bhg-Leu-Asp-Phe-N-MeIle-Trp; Seq ID No: 56
Ac-D-Bhg-Orn-Asp-Phe-N-MeIle-Trp; Seq ID No: 57
Ac-D-Bhg-Lys-Asp-Phe-N-MeIle-Trp; Seq ID No: 58
Ac-D-Bhg-Asp-Asp-Phe-N-MeIle-Trp; Seq ID No: 59
Ac-D-Bhg-Glu-Asp-Phe-N-MeIle-Trp; Seq ID No: 60
Ac-D-Bhg-Phe-Asp-Phe-N-MeIle-Trp; Seq ID No: 61
Ac-D-Bhg-Arg-Asp-Phe-N-MeIle-Trp; Seq ID No: 62
Ac-D-Bheg-Leu-Asp-Phe-N-MeIle-Trp; Seq ID No: 63
Ac-D-Bheg-Orn-Asp-Phe-N-MeIle-Trp; Seq ID No: 57
Ac-D-Bheg-Lys-Asp-Phe-N-MeIle-Trp; Seq ID No: 58
Ac-D-Bheg-Asp-Asp-Phe-N-MeIle-Trp; Seq ID No: 59
Ac-D-Bheg-Glu-Asp-Phe-N-MeIle-Trp; Seq ID No: 60
Ac-D-Bheg-Phe-Asp-Phe-N-MeIle-Trp; Seq ID No: 61
Ac-D-Bheg-Arg-Asp-Phe-N-MeIle-Trp; Seq ID No: 62
Ac-D-Bhg-Leu-N-MeAsp-Ile-Ile-Trp; Seq ID No: 15 and
Ac-D-Bhg-Arg-Asp-Ile-Ile-Tyr(CHO); Seq ID No: 64.

5. A pharmaceutical composition adapted for administration as an antagonist of endothelin comprising a therapeutically effective amount of a compound according to claim 1 in admixture with a pharmaceutically acceptable excipient, diluent, or carrier.

6. A pharmaceutical composition adapted for administration as an antihypertensive agent comprising a therapeutically effective amount of a compound according to claim 1 in admixture with a pharmaceutically acceptable excipient, diluent or carrier.

7. A pharmaceutical composition adapted for administration as an agent for treating metabolic and endocrine disorders comprising a therapeutically effective amount of a compound according to claim 1 in admixture with a pharmaceutically acceptable excipient, diluent or carrier.

8. A pharmaceutical composition adapted for administration as an agent for treating congestive heart failure and myocardial infarction comprising a therapeutically effective amount of a compound according to claim 1 in admixture with a pharmaceutically acceptable excipient, diluent or carrier.

9. A pharmaceutical composition adapted for administration as an agent for treating endotoxic shock comprising a therapeutically effective amount of a compound according to claim 1 in admixture with a pharmaceutically acceptable excipient, diluent or carrier.

10. A pharmaceutical composition adapted for administration as an agent for treating subarachnoid hemorrhage comprising a therapeutically effective amount of a compound according to claim 1 in admixture with a pharmaceutically acceptable excipient, diluent or carrier.

11. A pharmaceutical composition adapted for administration as an agent for treating arrhythmias comprising a therapeutically effective amount of a compound according to claim 1 in admixture with a pharmaceutically acceptable excipient, diluent or carrier.

12. A pharmaceutical composition adapted for administration as an agent for treating asthma comprising a therapeutically effective amount of a compound according to claim 1 in admixture with a pharmaceutically acceptable excipient, diluent or carrier.

13. A pharmaceutical composition adapted for administration as an agent for treating acute and chronic renal failure comprising a therapeutically effective amount of a compound according to claim 1 in admixture with a pharmaceutically acceptable excipient, diluent or carrier.

14. A pharmaceutical composition adapted for administration as an agent for treating preeclampsia comprising a therapeutically effective amount of a compound according to claim 1 in admixture with a pharmaceutically acceptable excipient, diluent or carrier.

15. A pharmaceutical composition adapted for administration as an agent for treating diabetes comprising a therapeutically effective amount of a compound according to claim 1 in admixture with a pharmaceutically acceptable excipient, diluent or carrier.

16. A method of treating neurological disorders comprising administering to a host suffering therefrom a therapeutically effective amount of a compound according to claim 1 in unit dosage form.

17. A pharmaceutical composition adapted for administration as an agent for treating neurological disorders comprising a therapeutically effective amount of a compound according to claim 1 in admixture with a pharmaceutically acceptable excipient, diluent, or carrier.

18. A method according to claim 16 wherein the neurological disorder is selected from the group consisting of: cerebral vasospasm stroke and head injury.

19. A pharmaceutical composition according to claim 17 wherein the agent for treating neurological disorders is selected from the group consisting of: cerebral vasospasm, stroke and head injury.

20. A pharmaceutical composition adapted for administration as an agent for treating pulmonary hypertension comprising a therapeutically effective amount of a compound according to claim 1 in admixture with a pharmaceutically acceptable excipient, diluent, or carrier.

21. A pharmaceutical composition adapted for administration as an agent for treating ischemic disease comprising a therapeutically effective amount of a compound according to claim 1 in admixture with a pharmaceutically acceptable excipient, diluent, or carrier.

22. A pharmaceutical composition adapted for administration as an agent for protecting against gastric mucosal damage or treating ischemic bowel disease comprising a therapeutically effective amount of a compound according to claim 1 in admixture with a pharmaceutically acceptable excipient, diluent, or carrier.

23. A pharmaceutical composition adapted for administration as an agent for treating atherosclerotic disorders including Raynaud's disease comprising a therapeutically effective amount of a compound according to claim 1 in admixture with a pharmaceutically acceptable excipient, diluent, or carrier.

24. A pharmaceutical composition adapted for administration as an agent for treating restenosis comprising a therapeutically effective amount of a compound according to claim 1 in admixture with a pharmaceutically acceptable excipient, diluent, or carrier.

25. A pharmaceutical composition adapted for administration as an agent for treating angina comprising a therapeutically effective amount of a compound according to claim 1 in admixture with a pharmaceutically acceptable excipient, diluent, or carrier.

26. A pharmaceutical composition adapted for administration as an agent for treating cancer comprising a therapeutically effective amount of a compound according to claim 1 in admixture with a pharmaceutically acceptable excipient, diluent, or carrier.

27. A pharmaceutical composition adapted for administration as an agent for treating hemorrhagic shock comprising a therapeutically effective amount of a compound according to claim 1 in admixture with a pharmaceutically acceptable excipient, diluent, or carrier.

* * * * *

UNITED STATES PATENT AND TRADEMARK OFFICE
CERTIFICATE OF CORRECTION

PATENT NO.   : 5,550,110  
DATED        : August 27, 1996  
INVENTOR(S)  : Wayne L. Cody, et al.

Page 1 of 1

It is certified that error appears in the above-identified patent and that said Letters Patent is hereby corrected as shown below:

Column 69,  
Delete line 50 and insert instead the structure as corrected

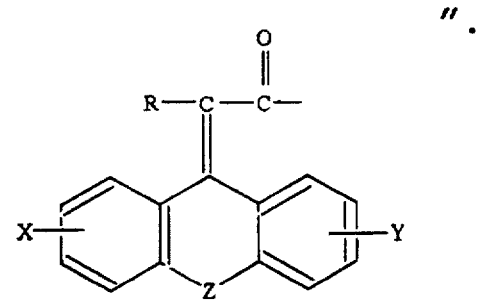

Column 76,  
Line 7 "$-(CH_2)_{na}-CH=CH-CH_{2\ n]\text{-}a}-$, should read "$-(CH_2)_{na}-CH=CH-CH_2)_{na\text{-}1}-$,"

Column 81, Line 50,  
"Fmoc—D—Bheg—Leu—D—Asp—Ile—N—MeIle—Trp—;"  
should read "Ac—D—Bheg—Asp—Ile—N—MeIle—Trp—;".

Column 84, Line 53,  
"cerebral vasospasm stroke and head injury" should read "cerebral vasospasm stroke and head injury".

Signed and Sealed this

Twenty-sixth Day of June, 2001

*Attest:*

*Attesting Officer*

NICHOLAS P. GODICI  
*Acting Director of the United States Patent and Trademark Office*